United States Patent
Kohli et al.

(10) Patent No.: US 11,484,365 B2
(45) Date of Patent: Nov. 1, 2022

(54) MEDICAL IMAGE GUIDANCE

(71) Applicant: InnerOptic Technology, Inc., Hillsborough, NC (US)

(72) Inventors: Luv Kohli, Durham, NC (US); Brian Heaney, Durham, NC (US); Kurtis Keller, Hillsborough, NC (US); Andrei State, Chapel Hill, NC (US)

(73) Assignee: InnerOptic Technology, Inc., Hillsborough, NC (US)

( * ) Notice: Subject to any disclaimer, the term of this patent is extended or adjusted under 35 U.S.C. 154(b) by 500 days.

(21) Appl. No.: 16/255,629

(22) Filed: Jan. 23, 2019

(65) Prior Publication Data

US 2019/0223958 A1   Jul. 25, 2019

(51) Int. Cl.
*A61B 34/20* (2016.01)
*A61B 8/08* (2006.01)
(Continued)

(52) U.S. Cl.
CPC ............ *A61B 34/20* (2016.02); *A61B 8/0841* (2013.01); *A61B 2017/3413* (2013.01);
(Continued)

(58) Field of Classification Search
CPC ..... A61B 34/20; A61B 8/0841; A61B 8/4427; A61B 8/5223; A61B 2017/3413;
(Continued)

(56) References Cited

U.S. PATENT DOCUMENTS 3,556,079 A   1/1971   Omizo
4,058,114 A   11/1977  Soldner
(Continued)

FOREIGN PATENT DOCUMENTS

EP   0 427 358       5/1991
JP   S63-290550 A   11/1988
(Continued)

OTHER PUBLICATIONS

U.S. Pat. No. 8,340,379 including its ongoing prosecution history, including without limitation Office Actions, Amendments, Remarks, and any other potentially relevant documents, Dec. 25, 2012, Razzaque et al.

(Continued)

*Primary Examiner* — Angela M Hoffa
*Assistant Examiner* — Younhee Choi
(74) *Attorney, Agent, or Firm* — Knobbe Martens Olson & Bear LLP

(57) ABSTRACT

A system and method for improved medical device navigation is disclosed. An example system can include a processor configured to determine an emplacement of a 2D medical image in a 3D virtual space, determine an emplacement of a virtual medical device in the 3D space, determine an intersection based on the emplacement of the 2D medical image and the emplacement of the virtual medical device, and/or determine a dynamic point-of-projection location for the virtual medical device based at least in part on the determined intersection. The processor can cause a display to display a rendering of the 2D medical image and a projection of the virtual medical device onto the 2D medical image from a perspective of the dynamic point-of-projection location. The display can be communicatively coupled to an imaging medical device. The viewing area can be parallel to a 2D region associated with the 2D medical image.

16 Claims, 26 Drawing Sheets

(51) Int. Cl.
  *A61B 17/34* (2006.01)
  *A61B 34/10* (2016.01)
  *A61B 90/00* (2016.01)
  *A61B 90/50* (2016.01)

(52) U.S. Cl.
  CPC ... *A61B 2034/102* (2016.02); *A61B 2034/107* (2016.02); *A61B 2034/2048* (2016.02); *A61B 2034/2051* (2016.02); *A61B 2034/2055* (2016.02); *A61B 2034/2065* (2016.02); *A61B 2090/364* (2016.02); *A61B 2090/372* (2016.02); *A61B 2090/373* (2016.02); *A61B 2090/378* (2016.02); *A61B 2090/3925* (2016.02); *A61B 2090/3983* (2016.02); *A61B 2090/502* (2016.02)

(58) Field of Classification Search
  CPC .... A61B 2034/2048; A61B 2034/2051; A61B 2034/102; A61B 2034/2055; A61B 2034/2065; A61B 2034/107; A61B 2090/372; A61B 2090/3983; A61B 2090/502; A61B 2090/3925; A61B 2090/378; A61B 2090/364; A61B 2090/373
  See application file for complete search history.

(56) References Cited

U.S. PATENT DOCUMENTS

| | | |
|---|---|---|
| RE30,397 E | 9/1980 | King |
| 4,249,539 A | 2/1981 | Vilkomerson et al. |
| 4,294,544 A | 10/1981 | Altschuler et al. |
| 4,390,025 A | 6/1983 | Takemura et al. |
| 4,407,294 A | 10/1983 | Vilkomerso |
| 4,431,006 A | 2/1984 | Trimmer et al. |
| 4,567,896 A | 2/1986 | Barnea et al. |
| 4,583,538 A | 4/1986 | Onik et al. |
| 4,620,546 A | 11/1986 | Aida et al. |
| 4,671,292 A | 6/1987 | Matzuk |
| 4,839,836 A | 6/1989 | Fonsalas |
| 4,862,873 A | 9/1989 | Yajima et al. |
| 4,884,219 A | 11/1989 | Waldren |
| 4,899,756 A | 2/1990 | Sonek |
| 4,911,173 A | 3/1990 | Terwillige |
| 4,945,305 A | 7/1990 | Blood |
| 5,076,279 A | 12/1991 | Arenson et al. |
| 5,078,140 A | 1/1992 | Kwoh |
| 5,078,142 A | 1/1992 | Siczek et al. |
| 5,095,910 A | 3/1992 | Powers |
| 5,109,276 A | 4/1992 | Nudelman et al. |
| 5,156,144 A | 10/1992 | Iwasaki et al. |
| 5,158,088 A | 10/1992 | Nelson et al. |
| 5,161,536 A | 11/1992 | Vikomerson et al. |
| 5,193,120 A | 3/1993 | Gamache et al. |
| 5,209,235 A | 5/1993 | Brisken et al. |
| 5,249,581 A | 10/1993 | Horbal et al. |
| 5,251,127 A | 10/1993 | Raab |
| 5,261,404 A | 11/1993 | Mick et al. |
| 5,265,610 A | 11/1993 | Darrow et al. |
| 5,271,400 A | 12/1993 | Dumoulin et al. |
| 5,307,153 A | 4/1994 | Maruyama et al. |
| 5,309,913 A | 5/1994 | Kormos et al. |
| 5,323,002 A | 6/1994 | Sampsell et al. |
| 5,371,543 A | 12/1994 | Anderson |
| 5,383,454 A | 1/1995 | Bucholz |
| 5,394,875 A | 3/1995 | Lewis et al. |
| 5,411,026 A | 5/1995 | Carol |
| 5,433,198 A | 7/1995 | Desai |
| 5,433,739 A | 7/1995 | Sluijter |
| 5,443,489 A | 8/1995 | Ben-Haim |
| 5,446,798 A | 8/1995 | Morita et al. |
| 5,447,154 A | 9/1995 | Cinquin et al. |
| 5,452,024 A | 9/1995 | Sampsell |
| 5,457,493 A | 10/1995 | Leddy et al. |
| 5,474,073 A | 12/1995 | Schwartz et al. |
| 5,476,096 A | 12/1995 | Olstad et al. |
| 5,483,961 A | 1/1996 | Kelly et al. |
| 5,488,431 A | 1/1996 | Gove et al. |
| 5,489,952 A | 2/1996 | Gove et al. |
| 5,491,510 A | 2/1996 | Gove |
| 5,494,039 A | 2/1996 | Onik et al. |
| 5,503,152 A | 4/1996 | Oakley et al. |
| 5,505,204 A | 4/1996 | Picot et al. |
| 5,515,856 A | 5/1996 | Olstad et al. |
| 5,517,990 A | 5/1996 | Kalfas et al. |
| 5,526,051 A | 6/1996 | Gove et al. |
| 5,526,812 A | 6/1996 | Dumoulin et al. |
| 5,529,070 A | 6/1996 | Augustine et al. |
| 5,531,227 A | 7/1996 | Schneider |
| 5,532,997 A | 7/1996 | Pauli |
| 5,541,723 A | 7/1996 | Tanaka |
| 5,558,091 A | 9/1996 | Acker et al. |
| 5,568,811 A | 10/1996 | Olstad |
| 5,570,135 A | 10/1996 | Gove et al. |
| 5,579,026 A | 11/1996 | Tabata |
| 5,581,271 A | 12/1996 | Kraemer |
| 5,588,948 A | 12/1996 | Takahashi et al. |
| 5,608,468 A | 3/1997 | Gove et al. |
| 5,608,849 A | 3/1997 | King, Jr. |
| 5,611,345 A | 3/1997 | Hibbeln |
| 5,611,353 A | 3/1997 | Dance et al. |
| 5,612,753 A | 3/1997 | Poradish et al. |
| 5,625,408 A | 4/1997 | Matsugu et al. |
| 5,628,327 A | 5/1997 | Unger et al. |
| 5,629,794 A | 5/1997 | Magel et al. |
| 5,630,027 A | 5/1997 | Venkateswar et al. |
| 5,647,361 A | 7/1997 | Damadian |
| 5,647,373 A | 7/1997 | Paltieli et al. |
| 5,660,185 A | 8/1997 | Shmulewitz et al. |
| 5,662,111 A | 9/1997 | Cosman |
| 5,699,444 A | 12/1997 | Palm |
| 5,701,898 A | 12/1997 | Adam et al. |
| 5,701,900 A | 12/1997 | Shehada et al. |
| 5,726,670 A | 3/1998 | Tabata et al. |
| 5,728,044 A | 3/1998 | Shan |
| 5,758,650 A | 6/1998 | Miller et al. |
| 5,766,135 A | 6/1998 | Terwilliger |
| 5,784,098 A | 7/1998 | Shoji et al. |
| 5,792,147 A | 8/1998 | Evans et al. |
| 5,793,701 A | 8/1998 | Wright et al. |
| 5,797,849 A | 8/1998 | Vesely et al. |
| 5,806,521 A | 9/1998 | Morimoto et al. |
| 5,807,395 A | 9/1998 | Mulier et al. |
| 5,810,008 A | 9/1998 | Dekel et al. |
| 5,817,022 A | 10/1998 | Vesely |
| 5,820,554 A | 10/1998 | Davis et al. |
| 5,820,561 A | 10/1998 | Olstad et al. |
| 5,829,439 A | 11/1998 | Yokosawa et al. |
| 5,829,444 A | 11/1998 | Ferre et al. |
| 5,851,183 A | 12/1998 | Bodiolz |
| 5,870,136 A | 2/1999 | Fuchs et al. |
| 5,891,034 A | 4/1999 | Bucholz |
| 5,920,395 A | 7/1999 | Schulz |
| 5,961,527 A | 10/1999 | Whitmore, III et al. |
| 5,967,980 A | 10/1999 | Ferre et al. |
| 5,967,991 A | 10/1999 | Gardineer et al. |
| 5,991,085 A | 11/1999 | Rallison et al. |
| 6,016,439 A | 1/2000 | Acker |
| 6,019,724 A | 2/2000 | Gronningsaeter et al. |
| 6,048,312 A | 4/2000 | Ishrak et al. |
| 6,064,749 A | 5/2000 | Hirota et al. |
| 6,091,546 A | 7/2000 | Spitzer |
| 6,095,982 A | 8/2000 | Richards-Kortum et al. |
| 6,099,471 A | 8/2000 | Torp et al. |
| 6,108,130 A | 8/2000 | Raj |
| 6,122,538 A | 9/2000 | Sliwa, Jr. et al. |
| 6,122,541 A | 9/2000 | Cosman et al. |
| 6,160,666 A | 12/2000 | Rallison et al. |
| 6,167,296 A | 12/2000 | Shahidi |
| 6,181,371 B1 | 1/2001 | Maguire, Jr. |
| RE37,088 E | 3/2001 | Olstad et al. |
| 6,216,029 B1 | 4/2001 | Paltieli |

(56) References Cited

U.S. PATENT DOCUMENTS

| | | |
|---|---|---|
| 6,241,725 B1 | 6/2001 | Cosman |
| 6,245,017 B1 | 6/2001 | Hashimoto et al. |
| 6,246,784 B1 | 6/2001 | Summers et al. |
| 6,246,898 B1 | 6/2001 | Vesely et al. |
| 6,248,101 B1 | 6/2001 | Witmore, III et al. |
| 6,261,234 B1 | 7/2001 | Lin |
| 6,341,016 B1 | 1/2002 | Malione |
| 6,348,058 B1 | 2/2002 | Melken et al. |
| 6,350,238 B1 | 2/2002 | Olstad et al. |
| 6,352,507 B1 | 3/2002 | Torp et al. |
| 6,379,302 B1 | 4/2002 | Kessman et al. |
| 6,385,475 B1 | 5/2002 | Cinquin et al. |
| 6,442,417 B1 | 8/2002 | Shahidi et al. |
| 6,447,450 B1 | 9/2002 | Olsdat |
| 6,456,868 B2 | 9/2002 | Saito et al. |
| 6,470,207 B1 | 10/2002 | Simon et al. |
| 6,471,366 B1 | 10/2002 | Hughson et al. |
| 6,477,400 B1 | 11/2002 | Barrick |
| 6,478,793 B1 | 11/2002 | Cosman et al. |
| 6,503,195 B1 | 1/2003 | Keller et al. |
| 6,511,418 B2 | 1/2003 | Shahidi et al. |
| 6,517,485 B2 | 2/2003 | Torp et al. |
| 6,518,939 B1 | 2/2003 | Kikuchi |
| 6,527,443 B1 | 3/2003 | Vilsmeier |
| 6,529,758 B2 | 3/2003 | Shahidi |
| 6,537,217 B1 | 3/2003 | Bjaerum et al. |
| 6,545,706 B1 | 4/2003 | Edwards et al. |
| 6,546,279 B1 | 4/2003 | Bova et al. |
| 6,547,777 B2 | 4/2003 | Di Resta et al. |
| 6,551,325 B2 | 4/2003 | Neubauer et al. |
| 6,570,566 B1 | 5/2003 | Yoshigahara |
| 6,575,969 B1 | 6/2003 | Rittman, III et al. |
| 6,579,240 B2 | 6/2003 | Bjaerum et al. |
| 6,587,711 B1 | 7/2003 | Alfano et al. |
| 6,591,130 B2 | 7/2003 | Shahidi |
| 6,592,522 B2 | 7/2003 | Bjaerum et al. |
| 6,594,517 B1 | 7/2003 | Nevo |
| 6,597,818 B2 | 7/2003 | Kumar et al. |
| 6,604,404 B2 | 8/2003 | Paltieli et al. |
| 6,616,610 B2 | 9/2003 | Steininger et al. |
| 6,626,832 B1 | 9/2003 | Paltieli et al. |
| 6,652,462 B2 | 11/2003 | Bjaerum et al. |
| 6,669,635 B2 | 12/2003 | Kessman et al. |
| 6,676,599 B2 | 1/2004 | Torp et al. |
| 6,689,067 B2 | 2/2004 | Sauer et al. |
| 6,695,786 B2 | 2/2004 | Wang et al. |
| 6,711,429 B1 | 3/2004 | Gilboa et al. |
| 6,725,082 B2 | 4/2004 | Sati et al. |
| 6,733,458 B1 * | 5/2004 | Steins ............... A61B 8/0833 600/461 |
| 6,764,449 B2 | 7/2004 | Lee et al. |
| 6,766,184 B2 | 7/2004 | Utzinger et al. |
| 6,768,496 B2 | 7/2004 | Bieger et al. |
| 6,775,404 B1 | 8/2004 | Pagoulatos et al. |
| 6,782,287 B2 | 8/2004 | Grzeszczuk et al. |
| 6,783,524 B2 | 8/2004 | Anderson et al. |
| 6,827,723 B2 | 12/2004 | Carson |
| 6,863,655 B2 | 3/2005 | Bjaerum et al. |
| 6,873,867 B2 | 3/2005 | Vilsmeier |
| 6,875,179 B2 | 4/2005 | Ferguson et al. |
| 6,881,214 B2 | 4/2005 | Cosman et al. |
| 6,895,268 B1 | 5/2005 | Rahn et al. |
| 6,915,150 B2 | 7/2005 | Cinquin et al. |
| 6,917,827 B2 | 7/2005 | Kienzle, III |
| 6,923,817 B2 | 8/2005 | Carson et al. |
| 6,936,048 B2 | 8/2005 | Hurst |
| 6,947,783 B2 | 9/2005 | Immerz |
| 6,968,224 B2 | 11/2005 | Kessman et al. |
| 6,978,167 B2 | 12/2005 | Dekel et al. |
| 7,008,373 B2 | 3/2006 | Stoianovici et al. |
| 7,033,360 B2 | 4/2006 | Cinquin et al. |
| 7,072,707 B2 | 7/2006 | Galloway, Jr. et al. |
| 7,077,807 B2 | 7/2006 | Torp et al. |
| 7,093,012 B2 | 8/2006 | Oltad et al. |
| 7,110,013 B2 | 9/2006 | Ebersole et al. |
| 7,171,255 B2 | 1/2007 | Holupka et al. |
| 7,209,776 B2 | 4/2007 | Leitner |
| 7,245,746 B2 | 7/2007 | Bjaerum et al. |
| 7,248,232 B1 | 7/2007 | Yamazaki et al. |
| 7,261,694 B2 | 8/2007 | Torp et al. |
| 7,313,430 B2 | 12/2007 | Urquhart et al. |
| 7,331,932 B2 | 2/2008 | Leitner |
| 7,351,205 B2 | 4/2008 | Szczech et al. |
| 7,379,769 B2 | 5/2008 | Piron et al. |
| 7,385,708 B2 | 6/2008 | Ackerman et al. |
| 7,392,076 B2 | 6/2008 | Moctezuma de la Barrera |
| 7,398,116 B2 | 7/2008 | Edwards |
| 7,466,303 B2 | 12/2008 | Yi et al. |
| 7,480,533 B2 | 1/2009 | Cosman et al. |
| 7,505,809 B2 | 3/2009 | Strommer et al. |
| 7,588,541 B2 | 9/2009 | Floyd et al. |
| 7,596,267 B2 | 9/2009 | Accomazzi et al. |
| 7,652,259 B2 | 1/2010 | Kimchy et al. |
| 7,662,128 B2 | 2/2010 | Salcudean et al. |
| 7,678,052 B2 | 3/2010 | Torp et al. |
| 7,728,868 B2 | 6/2010 | Razzaque et al. |
| 7,747,305 B2 | 6/2010 | Dean et al. |
| 7,797,032 B2 | 9/2010 | Martinelli et al. |
| 7,798,965 B2 | 9/2010 | Torp et al. |
| 7,833,168 B2 | 11/2010 | Taylor et al. |
| 7,833,221 B2 | 11/2010 | Voegele et al. |
| 7,846,103 B2 | 12/2010 | Cannon, Jr. et al. |
| 7,876,942 B2 | 1/2011 | Gilboa |
| 7,889,905 B2 | 2/2011 | Higgins et al. |
| 7,912,849 B2 | 3/2011 | Ohrn et al. |
| 7,920,909 B2 | 4/2011 | Lyon et al. |
| 7,962,193 B2 | 6/2011 | Edwards et al. |
| 7,976,469 B2 | 7/2011 | Bonde et al. |
| 8,023,712 B2 | 9/2011 | Ikuma et al. |
| 8,038,631 B1 | 10/2011 | Sanghvi et al. |
| 8,041,413 B2 | 10/2011 | Barbagli et al. |
| 8,050,736 B2 | 11/2011 | Piron et al. |
| 8,052,636 B2 | 11/2011 | Moll et al. |
| 8,066,644 B2 | 11/2011 | Sarkar et al. |
| 8,073,528 B2 | 12/2011 | Zhao et al. |
| 8,086,298 B2 | 12/2011 | Whitmore, III et al. |
| 8,135,669 B2 | 3/2012 | Olstad et al. |
| 8,137,281 B2 | 3/2012 | Huang et al. |
| 8,147,408 B2 | 4/2012 | Bunce et al. |
| 8,152,724 B2 | 4/2012 | Ridley et al. |
| 8,167,805 B2 | 5/2012 | Emery et al. |
| 8,216,149 B2 | 7/2012 | Oonuki et al. |
| 8,221,322 B2 | 7/2012 | Wang et al. |
| 8,228,028 B2 | 7/2012 | Schneider |
| 8,257,264 B2 | 9/2012 | Park et al. |
| 8,296,797 B2 | 10/2012 | Olstad et al. |
| 10,026,191 B2 | 7/2018 | Accomando et al. |
| 2001/0007919 A1 | 7/2001 | Shahidi |
| 2001/0016804 A1 | 8/2001 | Cunningham et al. |
| 2001/0031920 A1 | 10/2001 | Kaufman et al. |
| 2001/0041838 A1 | 11/2001 | Holupka et al. |
| 2001/0045979 A1 | 11/2001 | Matsumoto et al. |
| 2002/0010384 A1 | 1/2002 | Shahidi et al. |
| 2002/0032772 A1 | 3/2002 | Olstad et al. |
| 2002/0049375 A1 | 4/2002 | Strommer et al. |
| 2002/0077540 A1 | 6/2002 | Kienzie, III |
| 2002/0077543 A1 | 6/2002 | Grzeszczuk et al. |
| 2002/0103431 A1 | 8/2002 | Toker et al. |
| 2002/0105484 A1 | 8/2002 | Navab et al. |
| 2002/0135673 A1 | 9/2002 | Favalora et al. |
| 2002/0138008 A1 | 9/2002 | Tsujita et al. |
| 2002/0140814 A1 | 10/2002 | Cohen-Solal et al. |
| 2002/0156375 A1 | 10/2002 | Kessmam et al. |
| 2002/0198451 A1 | 12/2002 | Carson |
| 2003/0032878 A1 | 2/2003 | Shahidi |
| 2003/0040743 A1 | 2/2003 | Cosman et al. |
| 2003/0073901 A1 | 4/2003 | Simon et al. |
| 2003/0135119 A1 | 7/2003 | Lee et al. |
| 2003/0163142 A1 | 8/2003 | Paltieli et al. |
| 2003/0164172 A1 | 9/2003 | Chumas et al. |
| 2003/0231789 A1 | 12/2003 | Willis et al. |
| 2003/0233123 A1 | 12/2003 | Kindlein et al. |
| 2004/0034313 A1 | 2/2004 | Leitner |
| 2004/0078036 A1 | 4/2004 | Keidar |

(56) References Cited

U.S. PATENT DOCUMENTS

| | | |
|---|---|---|
| 2004/0095507 A1 | 5/2004 | Bishop et al. |
| 2004/0116810 A1 | 6/2004 | Olstad |
| 2004/0147920 A1 | 7/2004 | Keidar |
| 2004/0152970 A1 | 8/2004 | Hunter et al. |
| 2004/0181144 A1 | 9/2004 | Cinquin et al. |
| 2004/0215071 A1 | 10/2004 | Frank et al. |
| 2004/0238732 A1 | 12/2004 | State et al. |
| 2004/0243146 A1 | 12/2004 | Chesbrough et al. |
| 2004/0243148 A1 | 12/2004 | Wasielewski |
| 2004/0249281 A1 | 12/2004 | Olstad |
| 2004/0249282 A1 | 12/2004 | Olstad |
| 2004/0254454 A1 | 12/2004 | Kockro |
| 2005/0010098 A1 | 1/2005 | Frigstad et al. |
| 2005/0033160 A1 | 2/2005 | Yamagata et al. |
| 2005/0085717 A1 | 4/2005 | Shahidi |
| 2005/0085718 A1 | 4/2005 | Shahidi |
| 2005/0090733 A1 | 4/2005 | Van Der Lugt et al. |
| 2005/0090742 A1 | 4/2005 | Mine et al. |
| 2005/0107679 A1 | 5/2005 | Geiger et al. |
| 2005/0111733 A1 | 5/2005 | Fors et al. |
| 2005/0159641 A1 | 7/2005 | Kanai |
| 2005/0182316 A1 | 8/2005 | Burdette et al. |
| 2005/0192564 A1 | 9/2005 | Cosman et al. |
| 2005/0219552 A1 | 10/2005 | Ackerman et al. |
| 2005/0222574 A1 | 10/2005 | Giordano et al. |
| 2005/0231532 A1 | 10/2005 | Suzuki et al. |
| 2005/0240094 A1 | 10/2005 | Pichon et al. |
| 2005/0251148 A1 | 11/2005 | Friedrich |
| 2006/0004275 A1 | 1/2006 | Vija et al. |
| 2006/0020204 A1 | 1/2006 | Serra et al. |
| 2006/0036162 A1 | 2/2006 | Shahidi et al. |
| 2006/0052792 A1 | 3/2006 | Boettiger et al. |
| 2006/0058609 A1 | 3/2006 | Olstad |
| 2006/0058610 A1 | 3/2006 | Olstad |
| 2006/0058674 A1 | 3/2006 | Olstad |
| 2006/0058675 A1 | 3/2006 | Olstad |
| 2006/0100505 A1 | 5/2006 | Viswanathan |
| 2006/0122495 A1 | 6/2006 | Kienzle |
| 2006/0135866 A1* | 6/2006 | Namii .................... A61B 90/36 600/407 |
| 2006/0184040 A1 | 8/2006 | Keller et al. |
| 2006/0193504 A1 | 8/2006 | Saigo et al. |
| 2006/0229594 A1 | 10/2006 | Francischelli et al. |
| 2006/0235290 A1 | 10/2006 | Gabriel et al. |
| 2006/0235538 A1 | 10/2006 | Rochetin et al. |
| 2006/0241450 A1 | 10/2006 | Da Silva et al. |
| 2006/0253030 A1 | 11/2006 | Altmann et al. |
| 2006/0253032 A1 | 11/2006 | Altmann et al. |
| 2006/0271056 A1 | 11/2006 | Terrill-Grisoni et al. |
| 2006/0282023 A1 | 12/2006 | Leitner |
| 2006/0293643 A1 | 12/2006 | Wallace et al. |
| 2007/0002582 A1 | 1/2007 | Burwell et al. |
| 2007/0016035 A1 | 1/2007 | Hashimoto |
| 2007/0024617 A1 | 2/2007 | Poole |
| 2007/0032906 A1 | 2/2007 | Sutherland et al. |
| 2007/0073155 A1 | 3/2007 | Park et al. |
| 2007/0073455 A1 | 3/2007 | Oyobe et al. |
| 2007/0078346 A1 | 4/2007 | Park et al. |
| 2007/0167699 A1 | 7/2007 | Lathuiliere et al. |
| 2007/0167701 A1 | 7/2007 | Sherman |
| 2007/0167705 A1 | 7/2007 | Chiang et al. |
| 2007/0167771 A1 | 7/2007 | Olstad |
| 2007/0167801 A1 | 7/2007 | Webler et al. |
| 2007/0225553 A1 | 9/2007 | Shahidi |
| 2007/0239281 A1 | 10/2007 | Gotte et al. |
| 2007/0244488 A1 | 10/2007 | Metzger et al. |
| 2007/0255136 A1 | 11/2007 | Kristofferson et al. |
| 2007/0270718 A1 | 11/2007 | Rochetin et al. |
| 2007/0276234 A1 | 11/2007 | Shahidi |
| 2007/0291000 A1 | 12/2007 | Liang et al. |
| 2008/0004481 A1 | 1/2008 | Bax et al. |
| 2008/0004516 A1 | 1/2008 | DiSilvestro et al. |
| 2008/0030578 A1 | 2/2008 | Razzaque et al. |
| 2008/0039723 A1 | 2/2008 | Suri et al. |
| 2008/0051910 A1 | 2/2008 | Kammerzell et al. |
| 2008/0091106 A1 | 4/2008 | Kim et al. |
| 2008/0114235 A1 | 5/2008 | Unai et al. |
| 2008/0146939 A1 | 6/2008 | McMorrow et al. |
| 2008/0161824 A1 | 7/2008 | McMillen |
| 2008/0183080 A1 | 7/2008 | Abraham |
| 2008/0200794 A1 | 8/2008 | Teichman et al. |
| 2008/0208031 A1 | 8/2008 | Kurpad et al. |
| 2008/0208081 A1 | 8/2008 | Murphy et al. |
| 2008/0214932 A1 | 9/2008 | Mollard et al. |
| 2008/0232679 A1 | 9/2008 | Hahn et al. |
| 2008/0287794 A1 | 11/2008 | Li et al. |
| 2008/0287805 A1 | 11/2008 | Li |
| 2008/0287837 A1 | 11/2008 | Makin et al. |
| 2009/0024030 A1 | 1/2009 | Lachaine et al. |
| 2009/0036902 A1 | 2/2009 | DeMaio et al. |
| 2009/0105597 A1 | 4/2009 | Abraham |
| 2009/0118613 A1 | 5/2009 | Krugman et al. |
| 2009/0118724 A1 | 5/2009 | Zvuloni et al. |
| 2009/0131783 A1 | 5/2009 | Jenkins et al. |
| 2009/0137907 A1 | 5/2009 | Takimoto et al. |
| 2009/0196480 A1 | 8/2009 | Nields et al. |
| 2009/0234369 A1 | 9/2009 | Bax et al. |
| 2009/0312629 A1 | 12/2009 | Razzaque et al. |
| 2010/0152570 A1 | 6/2010 | Navab |
| 2010/0185087 A1 | 7/2010 | Nields et al. |
| 2010/0198045 A1 | 8/2010 | Razzaque et al. |
| 2010/0198402 A1 | 8/2010 | Greer et al. |
| 2010/0208963 A1 | 8/2010 | Kruecker et al. |
| 2010/0268072 A1 | 10/2010 | Hall et al. |
| 2010/0268085 A1 | 10/2010 | Kruecker et al. |
| 2010/0296718 A1 | 11/2010 | Ostrovsky-Berman et al. |
| 2010/0298705 A1 | 11/2010 | Pelissier et al. |
| 2010/0305448 A1 | 12/2010 | Dagonnau et al. |
| 2010/0312121 A1 | 12/2010 | Guan |
| 2010/0331252 A1 | 12/2010 | Hamrick |
| 2011/0043612 A1 | 2/2011 | Keller et al. |
| 2011/0046483 A1 | 2/2011 | Fuchs et al. |
| 2011/0057930 A1 | 3/2011 | Keller |
| 2011/0082351 A1 | 4/2011 | Razzaque et al. |
| 2011/0201915 A1 | 8/2011 | Gogin et al. |
| 2011/0201976 A1 | 8/2011 | Sanghvi et al. |
| 2011/0208055 A1 | 8/2011 | Dalal et al. |
| 2011/0230351 A1 | 9/2011 | Fischer et al. |
| 2011/0237947 A1 | 9/2011 | Boctor et al. |
| 2011/0238043 A1 | 9/2011 | Kleven |
| 2011/0251483 A1 | 10/2011 | Razzaque et al. |
| 2011/0274324 A1 | 11/2011 | Clements et al. |
| 2011/0282188 A1 | 11/2011 | Burnside et al. |
| 2011/0288412 A1 | 11/2011 | Deckman et al. |
| 2011/0295108 A1 | 12/2011 | Cox et al. |
| 2011/0301451 A1 | 12/2011 | Rohling |
| 2012/0035473 A1 | 2/2012 | Sanghvi et al. |
| 2012/0059260 A1 | 3/2012 | Robinson |
| 2012/0071759 A1 | 3/2012 | Hagy et al. |
| 2012/0078094 A1 | 3/2012 | Nishina et al. |
| 2012/0108955 A1 | 5/2012 | Razzaque et al. |
| 2012/0138658 A1 | 6/2012 | Ullrich et al. |
| 2012/0143029 A1 | 6/2012 | Silverstein et al. |
| 2012/0143055 A1 | 6/2012 | Ng et al. |
| 2012/0165679 A1 | 6/2012 | Orome et al. |
| 2012/0215096 A1 | 8/2012 | Gilboa |
| 2012/0230559 A1 | 9/2012 | Itai |
| 2012/0237105 A1 | 9/2012 | Mielekamp |
| 2012/0259210 A1 | 10/2012 | Harhen et al. |
| 2013/0030286 A1 | 1/2013 | Alouani et al. |
| 2013/0044930 A1 | 2/2013 | Li et al. |
| 2013/0079770 A1 | 3/2013 | Kyle, Jr. et al. |
| 2013/0090646 A1 | 4/2013 | Moss et al. |
| 2013/0096497 A1 | 4/2013 | Duindam et al. |
| 2013/0132374 A1 | 5/2013 | Olstad et al. |
| 2013/0144165 A1 | 6/2013 | Ebbini et al. |
| 2013/0151533 A1 | 6/2013 | Udupa et al. |
| 2013/0178745 A1 | 7/2013 | Kyle et al. |
| 2013/0218024 A1 | 8/2013 | Boctor et al. |
| 2013/0249787 A1 | 9/2013 | Morimoto |
| 2014/0051987 A1 | 2/2014 | Kowshik et al. |
| 2014/0058387 A1 | 2/2014 | Kruecker et al. |
| 2014/0078138 A1 | 3/2014 | Martin et al. |
| 2014/0201669 A1 | 7/2014 | Liu et al. |

(56) References Cited

U.S. PATENT DOCUMENTS

| | | | |
|---|---|---|---|
| 2014/0275760 A1 | 9/2014 | Lee et al. | |
| 2014/0275997 A1 | 9/2014 | Chopra et al. | |
| 2014/0350390 A1 | 11/2014 | Kudavelly et al. | |
| 2015/0235373 A1* | 8/2015 | Kato .................... | H04N 13/144 348/51 |
| 2015/0238259 A1 | 8/2015 | Albeck et al. | |
| 2015/0257847 A1 | 9/2015 | Higgins et al. | |
| 2016/0196694 A1 | 7/2016 | Lindeman | |
| 2016/0354152 A1* | 12/2016 | Beck ...................... | A61B 34/20 |
| 2017/0099479 A1 | 4/2017 | Browd et al. | |
| 2017/0348067 A1 | 12/2017 | Krimsky | |

FOREIGN PATENT DOCUMENTS

| | | |
|---|---|---|
| JP | H07-116164 A | 5/1995 |
| JP | 2005-058584 | 3/2005 |
| JP | 2005-323669 | 11/2005 |
| JP | 2009-517177 | 4/2009 |
| WO | WO 96/005768 | 2/1996 |
| WO | WO 97/015249 | 5/1997 |
| WO | WO 97/017014 | 5/1997 |
| WO | WO 97/029682 | 8/1997 |
| WO | WO 99/26534 | 6/1999 |
| WO | WO 01/039683 | 6/2001 |
| WO | WO 03/032837 | 4/2003 |
| WO | WO 03/034705 | 4/2003 |
| WO | WO 03/105289 | 12/2003 |
| WO | WO 05/010711 | 2/2005 |
| WO | WO 07/019216 | 2/2007 |
| WO | WO 07/067323 A2 | 6/2007 |
| WO | WO 08/017051 A2 | 2/2008 |
| WO | WO 09/063423 | 5/2009 |
| WO | WO 09/094646 | 7/2009 |
| WO | WO 10/057315 | 5/2010 |
| WO | WO 10/096419 A2 | 8/2010 |
| WO | WO 11/014687 A2 | 2/2011 |
| WO | WO 12/169990 | 12/2012 |
| WO | WO 13/116240 | 8/2013 |
| WO | WO 18/080844 | 5/2018 |

OTHER PUBLICATIONS

U.S. Pat. No. 8,350,902 including its ongoing prosecution history, including without limitation Office Actions, Amendments, Remarks, and any other potentially relevant documents, Jan. 8, 2013, Razzaque et al.

U.S. Pat. No. 8,482,606 including its ongoing prosecution history, including without limitation Office Actions, Amendments, Remarks, and any other potentially relevant documents, Jul. 9, 2013, Razzaque et al.

U.S. Pat. No. 8,554,307 including its ongoing prosecution history, including without limitation Office Actions, Amendments, Remarks, and any other potentially relevant documents, Oct. 8, 2013, Razzaque et al.

U.S. Pat. No. 8,585,598 including its ongoing prosecution history, including without limitation Office Actions, Amendments, Remarks, and any other potentially relevant documents, Nov. 19, 2013, Razzaque et al.

U.S. Pat. No. 8,641,621 including its ongoing prosecution history, including without limitation Office Actions, Amendments, Remarks, and any other potentially relevant documents, Feb. 4, 2014, Razzaque et al.

U.S. Pat. No. 8,670,816 including its ongoing prosecution history, including without limitation Office Actions, Amendments, Remarks, and any other potentially relevant documents, Mar. 11, 2014, Green et al.

U.S. Pat. No. 8,690,776 including its ongoing prosecution history, including without limitation Office Actions, Amendments, Remarks, and any other potentially relevant documents, Apr. 8, 2014, Razzaque et al.

U.S. Pat. No. 8,831,310 including its ongoing prosecution history, including without limitation Office Actions, Amendments, Remarks, and any other potentially relevant documents, Sep. 9, 2014, Razzaque et al.

U.S. Pat. No. 9,107,698 including its ongoing prosecution history, including without limitation Office Actions, Amendments, Remarks, and any other potentially relevant documents, Aug. 18, 2015, Razzaque et al.

U.S. Pat. No. 9,265,572 including its ongoing prosecution history, including without limitation Office Actions, Amendments, Remarks, and any other potentially relevant documents, Feb. 23, 2016, Fuchs et al.

U.S. Pat. No. 9,282,947 including its ongoing prosecution history, including without limitation Office Actions, Amendments, Remarks, and any other potentially relevant documents, Mar. 15, 2016, Razzaque et al.

U.S. Pat. No. 9,364,294 including its ongoing prosecution history, including without limitation Office Actions, Amendments, Remarks, and any other potentially relevant documents, Jun. 14, 2016, Razzaque et al.

U.S. Pat. No. 9,398,936 including its ongoing prosecution history, including without limitation Office Actions, Amendments, Remarks, and any other potentially relevant documents, Jul. 26, 2016, Razzaque et al.

U.S. Pat. No. 9,675,319 including its ongoing prosecution history, including without limitation Office Actions, Amendments, Remarks, and any other potentially relevant documents, Jun. 13, 2017, Razzaque et al.

U.S. Pat. No. 9,659,345 including its ongoing prosecution history, including without limitation Office Actions, Amendments, Remarks, and any other potentially relevant documents, May 23, 2017, Razzaque et al.

U.S. Pat. No. 9,901,406 including its ongoing prosecution history, including without limitation Office Actions, Amendments, Remarks, and any other potentially relevant documents, Feb. 27, 2018, State et al.

U.S. Pat. No. 9,949,700 including its ongoing prosecution history, including without limitation Office Actions, Amendments, Remarks, and any other potentially relevant documents, Apr. 24, 2018, Razzaque et al.

U.S. Pat. No. 10,127,629 including its ongoing prosecution history, including without limitation Office Actions, Amendments, Remarks, and any other potentially relevant documents, Nov. 13, 2018, Razzaque et al.

U.S. Pat. No. 10,136,951 including its ongoing prosecution history, including without limitation Office Actions, Amendments, Remarks, and any other potentially relevant documents, Nov. 27, 2018, Razzaque et al.

U.S. Pat. No. 10,188,467 including its ongoing prosecution history, including without limitation Office Actions, Amendments, Remarks, and any other potentially relevant documents, Jan. 29, 2019, Razzaque et al.

U.S. Pat. No. 10,278,778 including its ongoing prosecution history, including without limitation Office Actions, Amendments, Remarks, and any other potentially relevant documents, May 7, 2019, State et al.

U.S. Pat. No. 10,314,559 including its ongoing prosecution history, including without limitation Office Actions, Amendments, Remarks, and any other potentially relevant documents, Jun. 11, 2019, Razzaque et al.

U.S. Pat. No. 10,398,513 including its ongoing prosecution history, including without limitation Office Actions, Amendments, Remarks, and any other potentially relevant documents, Sep. 3, 2019, Razzaque et al.

U.S. Pat. No. 10,433,814 including its ongoing prosecution history, including without limitation Office Actions, Amendments, Remarks, and any other potentially relevant documents, Oct. 8, 2019, Razzaque et al.

U.S. Pat. No. 10,733,700 including its ongoing prosecution history, including without limitation Office Actions, Amendments, Remarks, and any other potentially relevant documents, Aug. 4, 2020, Keller et al.

(56) References Cited

OTHER PUBLICATIONS

U.S. Pat. No. 10,772,686 including its ongoing prosecution history, including without limitation Office Actions, Amendments, Remarks, and any other potentially relevant documents, Sep. 15, 2020, State et al.
U.S. Pat. No. 10,820,944 including its ongoing prosecution history, including without limitation Office Actions, Amendments, Remarks, and any other potentially relevant documents, Nov. 3, 2020, State et al.
U.S. Pat. No. 10,820,946 including its ongoing prosecution history, including without limitation Office Actions, Amendments, Remarks, and any other potentially relevant documents, Nov. 3, 2020, Heaney et al.
U.S. Pat. No. 11,103,200 including its ongoing prosecution history, including without limitation Office Actions, Amendments, Remarks, and any other potentially relevant documents, Aug. 31, 2021, Kohli et al.
U.S. Appl. No. 11/828,826 including its ongoing prosecution history, including without limitation Office Actions, Amendments, Remarks, and any other potentially relevant documents, filed Jul. 26, 2007, Keller et al.
U.S. Appl. No. 15/068,323 including its ongoing prosecution history, including without limitation Office Actions, Amendments, Remarks, and any other potentially relevant documents, filed Mar. 11, 2016, Razzaque et al.
U.S. Appl. No. 17/446,417 including its ongoing prosecution history, including without limitation Office Actions, Amendments, Remarks, and any other potentially relevant documents, filed Aug. 30, 2021, Kohli et al.
2010/0045783 including its ongoing prosecution history, including without limitation Office Actions, Amendments, Remarks, and any other potentially relevant documents, Feb. 25, 2010, State et al.
2014/0180074 including its ongoing prosecution history, including without limitation Office Actions, Amendments, Remarks, and any other potentially relevant documents, Jun. 26, 2014, Green.
2014/0275810 including its ongoing prosecution history, including without limitation Office Actions, Amendments, Remarks, and any other potentially relevant documents, Sep. 18, 2014, Keller et al.
2016/0166334 including its ongoing prosecution history, including without limitation Office Actions, Amendments, Remarks, and any other potentially relevant documents, Jun. 16, 2016, Razzaque.
2016/0270862 including its ongoing prosecution history, including without limitation Office Actions, Amendments, Remarks, and any other potentially relevant documents, Sep. 22, 2016, Fuchs et al.
2018/0289344 including its ongoing prosecution history, including without limitation Office Actions, Amendments, Remarks, and any other potentially relevant documents, Oct. 11, 2018, Green et al.
2019/0021681 including its ongoing prosecution history, including without limitation Office Actions, Amendments, Remarks, and any other potentially relevant documents, Jan. 24, 2019, Kohli.
2019/0060001 including its ongoing prosecution history, including without limitation Office Actions, Amendments, Remarks, and any other potentially relevant documents, Feb. 28, 2019, Kohli et al.
2019/0167354 including its ongoing prosecution history, including without limitation Office Actions, Amendments, Remarks, and any other potentially relevant documents, Jun. 6, 2019, Heaney et al.
2019/0247130 including its ongoing prosecution history, including without limitation Office Actions, Amendments, Remarks, and any other potentially relevant documents, Aug. 15, 2019, State.
2020/0046315 including its ongoing prosecution history, including without limitation Office Actions, Amendments, Remarks, and any other potentially relevant documents, Feb. 13, 2020, State.
2020/0138402 including its ongoing prosecution history, including without limitation Office Actions, Amendments, Remarks, and any other potentially relevant documents, May 7, 2020, Kohli.
2021/0027418 including its ongoing prosecution history, including without limitation Office Actions, Amendments, Remarks, and any other potentially relevant documents, Jan. 28, 2021, Keller.
2021/0113273 including its ongoing prosecution history, including without limitation Office Actions, Amendments, Remarks, and any other potentially relevant documents, Apr. 22, 2021, State.
2021/0161600 including its ongoing prosecution history, including without limitation Office Actions, Amendments, Remarks, and any other potentially relevant documents, Jun. 3, 2021, Heaney.
2021/0161601 including its ongoing prosecution history, including without limitation Office Actions, Amendments, Remarks, and any other potentially relevant documents, Jun. 3, 2021, State.
"3D Laparoscope Technology," http://www.inneroptic.com/tech_3DL.htm, copyright 2007 InnerOptic Technology, Inc. printed Sep. 19, 2007, 2 pages.
"AIM 3D Needle Placement Software from InnerOptic", Medgadget, Sep. 21, 2012.
AIM Section 5: 510k Summary, submitted by InnerOptic Technology, Inc., in 5 pages, submission date May 17, 2012.
"Cancer Facts & Figures 2004," www.cancer.org/downloads/STT/CAFF_finalPWSecured.pdf, copyright 2004 American Cancer Society, Inc., printed Sep. 19, 2007, 60 pages.
Cancer Prevention & Early Detection Facts & Figures 2004; National Center for Tobacco-Free Kids; 2004; American Cancer Society; USA.
"David Laserscanner <-Latest News <-Institute for Robotics and Process Control <-Te . . . ," http://www/rob.cs.tu-bs.de/en/news/david, printed Sep. 19, 2007, 1 page.
"InnerOptic's AIM System Receives Da 510(K) Clearance", InnerOptic Technology, Inc., Sep. 18, 2012.
"Laser scanned 3d model Final" video, still image of video attached, http://www.youtube.com/watch?v+DaLglgmoUf8, copyright 2007 YouTube, LLC, printed Sep. 19, 2007, 2 pages.
"Olympus Endoscopic Ultrasound System," www.olympusamerica.com/msg_section/download_brochures/135_b_gfum130.pdf, printed Sep. 20, 2007, 20 pages.
"Point Grey Research Inc.—Imaging Products—Triclops SDK Samples," http://www.ptgrey.com/products/triclopsSDK/samples.asp, copyright 2007 Point Grey Research Inc., printed Sep. 19, 2007, 1 page.
"Robbins, Mike—Computer Vision Research—Stereo Depth Perception," http://www.compumike.com/vision/stereodepth. php, copyright 2007 Michael F. Robbins, printed Sep. 19, 2007, 3 pages.
"RUE, Registered Ultrasound-Endoscope," copyright 2007 InnerOptic Technology, Inc., 2 pages.
Advertisement, "Inspeck 3DC 3D Capturor," Inspeck 3DC 3D Capturor (www.inspeck.com), 1998.
Advertisement, "Virtual 3D High Speed Non-Contact Surface Perception," Virtual 3-D Technologies Corporation (www.virtual3dtech.com)., Dec. 21, 1998.
Advertisements, "Virtuoso," Visual Interface, Inc. (www.visint.com), Dec. 21, 1998.
Akka, "Automatic Software Control of Display Parameters for Stereoscopic Graphics Images," SPIE vol. 1669: Stereoscopic Displays and Applications III, pp. 31-38 (1992).
Ali et al., "Near Infrared Spectroscopy and Imaging to Probe Differences in Water Content in Normal and Cancer Human Prostate Tissues," Technology in Cancer Research & Treatment; Oct. 2004; 3(5):491-497; Adenine Press.
Aylward et al., Analysis of the Parameter Space of a Metric for Registering 3D Vascular Images, in W. Niessen and M. Viergever (Eds.): MICCAI 2001, LNCS 2208, pp. 932-939, 2001.
Aylward et al., Registration and Analysis of Vascular Images, International Journal of Computer Vision 55(2/3), 123-138, 2003.
Aylward, et al., Intra-Operative 3D Ultrasound Augmentation, Proceedings of the IEEE International Symposium on Biomedical Imaging, Washington, Jul. 2002.
Azuma et al., "Improving Static and Dynamic Registration in an Optical See-Through HMD," Paper Presented at Siggraph '94 Annual Conference in Orlando, FL, 17 pages (1994).
Azuma, "A Survey of Augmented Reality," Presence: Teleoperators and Virtual Environments 6, 4:1-48 (Aug. 1997).
Badler et al., "Simulating Humans: Computer Graphics, Animation, and Control," Oxford University Press (1993).
Bajura, Michael et al., "Merging Virtual Objects with the Real World: Seeing Ultrasound Imagery within the Patient," Computer

(56) References Cited

OTHER PUBLICATIONS

Graphics, Proceedings of Siggraph 1992, vol. 26(2), pp. 203-210, available from www.cs.unc.edu/~fuchs/publications/MergVirtObjs92.pdf, printed Sep. 20, 2007, 8 pages.

Benavides et al., "Multispectral digital colposcopy for in vivo detection of cervical cancer," Optics Express; May 19, 2003; 11(10) Optical Society of America; USA.

Beraldin, J.A. et al., "Optimized Position Sensors for Flying-Spot Active Triangulation Systems," Proceedings of the Fourth International Conference on a 3-D Digital Imaging and Modeling (3DIM), Banff, Alberta, Canada, Oct. 6-10, 2003, pp. 334-341, NRC 47083, copyright 2003 National Research Council of Canada, http://iit-iti.nrc-cnrc.gc.ca/iit-publications-iti/docs/NRC-47083.pdf, printed Sep. 19, 2007, 9 pages.

Billinghurst, M. et al., Research Directions in Handheld AR; Int. J. of Virtual Reality 5(2),51-58 (2006).

Blais, F., "Review of 20 Years of Range Sensor Development," Journal of Electronic Imaging, 13(1):231-240, Jan. 2004, NRC 46531, copyright 2004 National Research Council of Canada, http://iit-iti.nrc-cnrc.gc.ca/iit-publications-iti/docs/NRC-46531.pdf, printed Sep. 19, 2007, 14 pages.

Bouguet, Jean-Yves, "Camera Calibration Toolbox for Matlab," www.vision.caltech.edu/bouguetj/calib_doc, printed Sep. 20, 2007, 5 pages.

Buxton et al.; "Colposcopically directed punch biopsy: a potentially misleading investigation," British Journal of Obstetrics and Gynecology; Dec. 1991; 98:1273-1276.

Caines, Judy S. et al. Stereotaxic Needle Core Biopsy of Breast Lesions Using a Regular Mammographic Table with an Adaptable Stereotaxic Device, American Journal of Roentgenology, vol. 163, No. 2, Aug. 1994, pp. 317-321. Downloaded from www.ajrorline.org on Jul. 10, 2013.

Cantor et al., "Cost-Effectiveness Analysis of Diagnosis and Management of Cervical Squamous Intraepithelial Lesions," Diagnostic Strategies for SILs; Feb. 1998; 91(2):270-277.

Catalano et al. "Multiphase helical CT findings after percutaneous ablation procedures for hepatocellular carcinoma." Abdom. Imaging, 25(6),2000, pp. 607-614.

Chiriboga et al., "Infrared Spectroscopy of Human Tissue. IV. Detection of Dysplastic and Neoplastic Changes of Human Cervical Tissue Via Infrared Microscopy," Cellular and Molecular Biology; 1998; 44(1): 219-229.

Crawford, David E. et al., "Computer Modeling of Prostate Biopsy: Tumor Size and Location—Not Clinical Significance—Determine Cancer Detection," Journal of Urology, Apr. 1998, vol. 159(4), pp. 1260-1264, 5 pages.

Deering, Michael "High Resolution Virtual Reality." Proceedings of Siggraph '92, Computer Graphics, 26(2), 1992, pp. 195-202.

Depiero et al., "3-D Computer Vision Using Structured Light: Design, Calibration and Implementation Issues," The University of Tennessee, pp. 1-46, (1996).

Dodd, G.D. et al. "Minimally invasive treatment of malignant hepatic tumors: at the threshold of a major breakthrough." Radiographies 20(1),2000, pp. 9-27.

Drascic et al., "Perceptual Issues in Augmented Reality," SPIE vol. 2653: Stereoscopic Displays and Virtual Reality Systems III, pp. 123-134 (Feb. 1996).

Dumoulin, C.L. et al., Real-Time Position Monitoring of Invasive Devices Using Magnetic Resonance, Magnetic Resonance in Medicine, vol. 29, Issue 3, Mar. 1993, pp. 411-415.

Edwards et al., Video See-Through Design for Merging of Real and Virtual Environments, VRAIS '93, pp. 1-11 (1993).

Fahey et al., "Meta-analysis of Pap Test Accuracy; American Journal of Epidemiology," 1995 141(7):680-689; The John Hopkins University School of Hyqiene and Public Health; USA.

Foxlin et al., "An Inertial Head-Orientation Tracker with Automatic Drift Compensation for Use with HMD's," Proceedings of the 1994 Virtual Reality Software and Technology Conference, Aug. 23-26, 1994, Singapore, pp. 159-173 (1994).

Fronheiser et al., Real-Time 3D Color Doppler for Guidance of Vibrating Interventional Devices, IEEE Ultrasonics Symposium, pp. 149-152 (2004).

Fuchs, Henry et al. "Augmented Reality Visualization for Laparoscopic Surgery," Proceedings of Medical Image Computing and Computer-Assisted Intervention (MICCAI) 1998, pp. 934-943, available from www.cs.unc.edu/~fuchs/publications /AugRealVis_LaparoSurg98.pdf, printed Sep. 20, 2007, 10 pages.

Fuchs, et al.: "Optimizing a Head-Tracked Stereo Display System to Guide Hepatic Tumor Ablation," Departments of Computer Sciences and Radiology, and School of Medicine, University of North Carolina at Chapel Hill; InnerOptic Technology, Inc. 2008.

Fuchs, et al.: "Virtual Environments Technology To Aid Needle Biopsies of the Breast," Health Care in the Information Age, Ch. 6, pp. 60-61, Presented in San Diego, Jan. 17-20, 1996, published by IOS Press and Ohmsha Feb. 1996.

Fuhrmann A. et al., Comprehensive calibration and registration procedures for augmented reality; Proc. Eurographics Workshop on Virtual Environments 2001,219-228 (2001).

Garrett, William F. et al., "Real-Time Incremental Visualization of Dynamic Ultrasound vols. Using Parallel BSP Trees," Proceedings of IEEE Visualization 1996, pp. 235-240, available from www.cs.unc.edu/~andrei/pubs/1996_VIS_dualBSP_Mac.pdf, printed Sep. 20, 2007, 7 pages.

Georgakoudi et al., "Trimodal spectroscopy for the detection and characterization of cervical precancers in vivo," American Journal of Obstetrics and Gynecology; Mar. 2002; 186(3):374-382; USA.

StereoMirror Technology Webpage, http://www.planar.com/products/flatpanel_monitors/stereoscopic/ (Printed Dec. 29, 2011).

Herline et al., Surface Registration for Use in Interactive, Image-Guided Liver Surgery, Computer Aided Surgery 5:11-17 (2000).

Holloway, R.; Registration Error Analysis for Augmented Reality; Presence: Teleoperators and Virtual Environments 6(4), 413-432 (1997).

Hornung et al., "Quantitative near-infrared spectroscopy of cervical dysplasia in vivo," Human Reproduction; 1999; 14(11):2908-2916; European Society of Human Reproduction and Embryology.

Howard, M.D., et al.: "An Electronic Device for Needle Placement during Sonographically Guided Percutaneous Intervention", Radiology 2001; 218:905-911.

InnerAim Brochure; 3D Visualization Software for Simpler, Safer, more Precise Aiming, Published no earlier than Apr. 1, 2010.

InVision System Brochure; A "GPS" for Real-Time 3D Needle Visualization & Guidance, Published no earlier than Mar. 1, 2008.

InVision User Manual; Professional Instructions for Use, Published no earlier than Dec. 1, 2008.

Jacobs, Marco C. et al., "Managing Latency in Complex Augmented Reality Systems," ACM Siggraph Proceedings of the Symposium of Interactive 3D Graphics 1997, pp. 49-54, available from www.es.unc.edu/~us/Latency//ManagingRelativeLatency.html, printed Sep. 20, 2007, 12 pages.

Jolesz, Ferenc A, M.D., et al. MRI-Guided Laser-Induced Interstitial Thermotherapy: Basic Principles, SPIE Institute on Laser-Induced Interstitial Thermotherapy (L1TT), Jun. 22-23, 1995, Berlin, Germany.

Kadi, A Majeed, et al., Design and Simulation of an Articulated Surgical Arm for Guiding Sterotactic Neurosurgery, SPIE vol. 1708 Applications of Artificial Intelligence X: Machine Vision and Robotics (1992). Downloaded from: http://proceedings.spiedigitallibrary.org/ on Jul. 11, 2013.

Kanbara et al., "A Stereoscopic Video See-through Augmented Reality System Based on Real-time Vision-Based Registration," Nara Institute of Science and Technology, pp. 1-8 (2000).

Kato, Amami, et al., A frameless, armless navigational system for computer-assisted neurosurgery, Journal of Neurosurgery, vol. 74, No. 5, May 1991, pp. 845-849.

Keller et al., "What is it in Head Mounted Displays (MDs) that really make them all so terrible?," pp. 1-8 (1998).

Lass, Amir, "Assessment of Ovarian Reserve," Human Reproduction, 2004, vol. 19(3), pp. 467-469, available from http://humrep.oxfordjournals.orgcgi/reprint/19/3/467, printed Sep. 20, 2007, 3 pages.

(56) References Cited

OTHER PUBLICATIONS

Lee, et al., "Modeling Real Objects Using Video See-Through Augmented Reality," Proceedings of the Second International Symposium on Mixed Reality, ISMR 2001, pp. 19-26 (Mar. 14-15, 2001).
Lee et al., "Modeling Real Objects Using Video See-Through Augmented Reality," Presence, 11(2):144-157 (Apr. 2002).
Leven et al., DaVinci Canvas: A Telerobotic Surgical System with Integrated, Robot-Assisted, Laparoscopic Ultrasound Capability, in J. Duncan and G. Gerig (Eds.): MICCAI 2005, LNCS 3749, pp. 811-818, 2005.
Levy, et al., An Internet-Connected, Patient Specific, Deformable Brain Atlas Integrated into a Surgical Navigation System, Journal of Digital Imaging, vol. 10, No. 3. Suppl. 1 (Aug. 1997): pp. 231-237.
Lindeman, A Low-Cost, Low-latency Approach to Dynamic Immersion in Occlusive Head-Mounted Displays, University of Canterbury, WPI,—Poster from IEEE VR 2016, Mar. 19-23, 2016.
Lipton, "Foundations of the Steroscopic Cinema A Study in Depth," Van Nostrad Reinhold Company, pp. 1-319 (1982).
Livingston, Mark A. et al., "Magnetic Tracker Calibration for Improved Augmented Reality Registration," Presence: Teleoperators and Virtual Environments, 1997, vol. 6(5), pp. 532-546, available from www.cs.unc.edu/~andrei/pubs/1997_Presence_calibr.pdf, printed Sep. 20, 2007, 14 pages.
Matsunaga et al., "The Effect of the Ratio Difference of Overlapped Areas of Stereoscopic Images on each Eye in a Teleoperalion," Stereoscopic Displays and Virtual Reality Systems VII, Proceedings of SPIE, 3957:236-243 (2000).
Meehan, Michael et al., "Effect of Latency on Presence in Stressful Virtual Environment," Proceedings of IEEE Virtual Reality 2003, pp. 141-148, available from http://www.cs.unc.edu/~eve/pubs.html, printed Sep. 20, 2007, 8 pages.
Milgram et al., "Adaptation Effects in Stereo due to Online Changes in Camera Configuration," SPIE vol. 1669-13, Stereoscopic Displays and Applications III, 17 pages (1992).
Mitchell et al., "Colposcopy for the Diagnosis of Squamous Intraepithelial lesions: A metaanalysis," Obstetrics and Gynecology; Apr. 1998; 91(4):626-631.
Nakamoto et al., 3D Ultrasound System Using a Magneto-optic Hybrid Tracker for Augmented Reality Visualization in Laparoscopic Liver Surgery, in T. Dohi and R. Kikinis (Eds.): MICCAI 2002, LNCS 2489, pp. 148-155, 2002.
Nordstrom et al., "Identification of Cervical Intraepithelial Neoplasia (CIN) Using UV-Excited Fluorescence and Diffuse-Reflectance Tissue Spectroscopy," Lasers in Surgery and Medicine; 2001; 29; pp. 118-127; Wiley-Liss, Inc.
Ohbuchi et al. "An Incremental Volume Rendering Algorithm for Interactive 3D Ultrasound Imaging", UNC-CH Computer Science Technical Report TR91-003, (1991).
Ohbuchi et al., "Incremental Volume Reconstruction and Rendering for 3D Ultrasound Imaging," Visualization in Biomedical Computing, SPIE Proceedings, pp. 312-323, (Oct. 13, 1992).
Ohbuchi, "Incremental Acquisition and Visualization of 3D Ultrasound Images," Ph.D. Dissertation, UNC-CH Computer Science Technical Report TR95-023, (1993).
Ohnesorge, Lauren K., "InnerOptic technology wins FDA approval", Triangle Business Journal, Sep. 19, 2012.
Pogue, Brian W. et al., "Analysis of acetic acid-induced whitening of high-grade squamous intraepitheliallesions," Journal of Biomedical Optics; Oct. 2001; 6(4):397-403.
Press Release: Pathfinder and InnerOptic Announce Technology Integration to Enhance Visualization and Outcomes in Liver Surgery, Published Mar. 6, 2013.
Raij, A.B., et al., Comparing Interpersonal Interactions with a Virtual Human to Those with a Real Human; IEEE Transactions on Visualization and Computer Graphics 13(3), 443-457 (2007).
Raz et al, Real-Time Magnetic Resonance Imaging-Guided Focal Laser Therapy in Patients with Low-Risk Prostate Cancer, European Urology 58, pp. 173-177. Mar. 12, 2010.
Robinett et al., "A Computational Model for the Stereoscopic Optics of a Head-Mounted Display," SPIE vol. 1457, Stereoscopic Displays and Applications II, pp. 140-160 (1991).
Rolland et al., Towards Quantifying Depth and Size Perception in Virtual Environments, Presence: Teleoperators and Virtual Environments, Winter 1995, vol. 4, Issue 1, pp. 1-21 and 24-49.
Rosenthal, Michael et al., "Augmented Reality Guidance for Needle Biopsies: An Initial Randomized, Controlled Trial in Phantoms," Proceedings of Medical Image Analysis, Sep. 2002, vol. 6(3), pp. 313-320, available from www.cs.unc.edu/~fuchs/publications/AugRealGuida_NeedleBiop02.pdf, printed Sep. 20, 2007, 8 pages.
Rosenthal, Michael et al., "Augmented Reality Guidance for Needle Biopsies: A Randomized, Controlled Trial in Phantoms," Proceedings of MICCAI 2001, eds. W. Niessen and M. Viergever, Lecture Notes in Computer Science, 2001, vol. 2208, pp. 240-248, available from www.cs.unc.edu/~us/AugmentedRealityAssistance.pdf, printed Sep. 20, 2007, 9 pages.
Screenshots from video produced by the University of North Carolina, produced circa 1992.
"Sony Introduces Head-Mounted Display for Endoscopic Surgery" (Jul. 23, 2013), retrieved Sep. 27, 2016, 5 pages, available at http://www.medgaget.com/2013/07/sony-introduces-head-mounted-display-for-endoscopic-surgery.html.
"Sony Introduces 'head-mount image processing unit' for endoscopic image display" (Jul. 23, 2013), retrieved Sep. 27, 2016, 14 pages, available at http://www.sony.net/SonyInfo/News/Press/201307/13-085E/index.html.
State et al., "Case Study: Observing a Volume Rendered Fetus within a Pregnant Patient," Proceedings of IEEE Visualization 1994, pp. 364-368, available from www.cs.unc.edu/~fuchs/publications/cs-ObservVolRendFetus94.pdf, printed Sep. 20, 2007, 5 pages.
State et al., "Interactive Volume Visualization on a Heterogeneous Message-Passing Multicomputer," Proceedings of 1995 Symposium on Interactive 3D Graphics, 1995, pp. 69-74, 208, available from www.cs.unc.edu/~andrei/pubs/1995_I3D_vol2_Mac.pdf, printed Sep. 20, 2007.
State et al., "Simulation-Based Design and Rapid Prototyping of a Parallax-Free, Orthoscopic Video See-Through Head-Mounted Display," Proceedings of International Symposium on Mixed and Augmented Reality (ISMAR) 2005, available from www.cs.unc.edu/~andrei/pubs/2005_ISMAR_VSTHMD_design.pdf, printed Sep. 20, 2007, 4 pages.
State et al., "Stereo Imagery from the UNC Augmented Reality System for Breast Biopsy Guidance" Proc. Medicine Meets Virtual Reality (MMVR) 2003 (Newport Beach, CA, Jan. 22-25, 2003).
State et al., "Superior Augmented Reality Registration by Integrating Landmark Tracking and Magnetic Tracking," ACM Siggraph Computer Graphics, Proceedings of Siggraph 1996, 10 pages (Aug. 1996).
State et al., "Technologies for Augmented Reality Systems: Realizing Ultrasound-Guided Needle Biopsies," Proc. Siggraph 96 (New Orleans, LA, Aug. 4-9, 1996). In Computer Graphics Proceedings, Annual Conference Series, 1996, ACM Siggraph, pp. 439-446.
State, Andrei "Exact Eye Contact with Virtual Humans." Proc. IEEE International Workshop on Human Computer Interaction 2007 (Rio de Janeiro, Brazil, Oct. 20, 2007), pp. 138-145.
State, et al.: Contextually Enhanced 3D Visualization for Multi-Born Tumor Ablation Guidance, Departments of Computer Science and Radiology, and School of Medicine, University of North Carolina at Chapel Hill; InnerOptic Technology, Inc. 2008, Chapel Hill, NC, pp. 70-77.
Symons et al., "What are You Looking at? Acuity for Triadic Eye Gaze," J. Gen. Psychology 131(4), pp. 451-469 (2004).
Takacs et al., "The Virtual Human Interface: A Photorealistic Digital Human," IEEE Computer Graphics and Applications 23(5), pp. 38-45 (2003).
Takagi et al., "Development of a Stereo Video See-through HMD for AR Systems," IEEE, pp. 68-77 (2000).
Takayama et al., "Virtual Human with Regard to Physical Contact and Eye Contact," Entertaining Computing 2005, LNCS, vol. 3711, pp. 268-278 (2005).
Ultraguide 1000 System, Ultraguide, www.ultraguideinc.com, 1998.

(56) References Cited

OTHER PUBLICATIONS

Van Staveren et al., "Light Scattering in Intralipid-10% in the wavelength range of 400-1100 nm," Applied Optics; Nov. 1991; 30(31):4507-4514.
Viola et al., "Alignment by Maximization of Mutual Information," International Journal of Computer Vision, vol. 24, No. 2, pp. 137-154 (1997).
Viola, Paul A., Alignment by Maximization of Mutual Information, Ph.D. Dissertation, MIT-Artificial Intelligence Laboratory Technical Report No. 1548 (Jun. 1995), 156 pages.
Ware et al., "Dynamic Adjustment of Stereo Display Parameters," IEEE Transactions on Systems, Many and Cybernetics, 28(1):1-19 (1998).
Watson et al., "Using Texture Maps to Correct for Optical Distortion in Head-Mounted Displays," Proceedings of the Virtual Reality Annual Symposium '95, IEEE, pp. 1-7 (1995).
Welch, Hybrid Self-Tracker: An Inertial/Optical Hybrid Three-Dimensional Tracking System, University of North Carolina Chapel Hill Department of Computer Science, TR 95-048 (1995).
Yinghui et al., Real-Time Deformation Using Modal Analysis on Graphics Hardware, Graphite 2006, Kuala Lumpur, Malaysia, Nov. 29-Dec. 2, 2006.
Zitnick et al., "Multi-Base Stereo Using Surface Extraction," Visual Interface Inc., (Nov. 24, 1996).

\* cited by examiner

MEDICAL IMAGE GUIDANCE

CROSS-REFERENCE TO RELATED APPLICATIONS

The present application claims priority benefit to U.S. Provisional Application No. 62/620,903, entitled "Guidance For Vascular Access," filed Jan. 23, 2018, U.S. Provisional Application No. 62/790,379, entitled "Guidance For Vascular Access," filed Jan. 9, 2019, U.S. Provisional Application No. 62/733,887, entitled "Probe-Aligned Ultrasound Display To Assist Medical Device Navigation," filed Sep. 20, 2018, and U.S. Provisional Application No. 62/655,976, entitled "Enhanced Visualizations For Medical Device Guidance," filed Apr. 11, 2018, each of which is hereby incorporated herein by reference in its entirety.

BACKGROUND

Various systems are available to aid a healthcare provider to guide a medical device in a patient or to provide a user viewing an object with additional information. The systems can provide image guidance cues to aid the healthcare provider or user and can also provide additional information for the user's benefit.

DETAILED DESCRIPTION

Figure 1A:
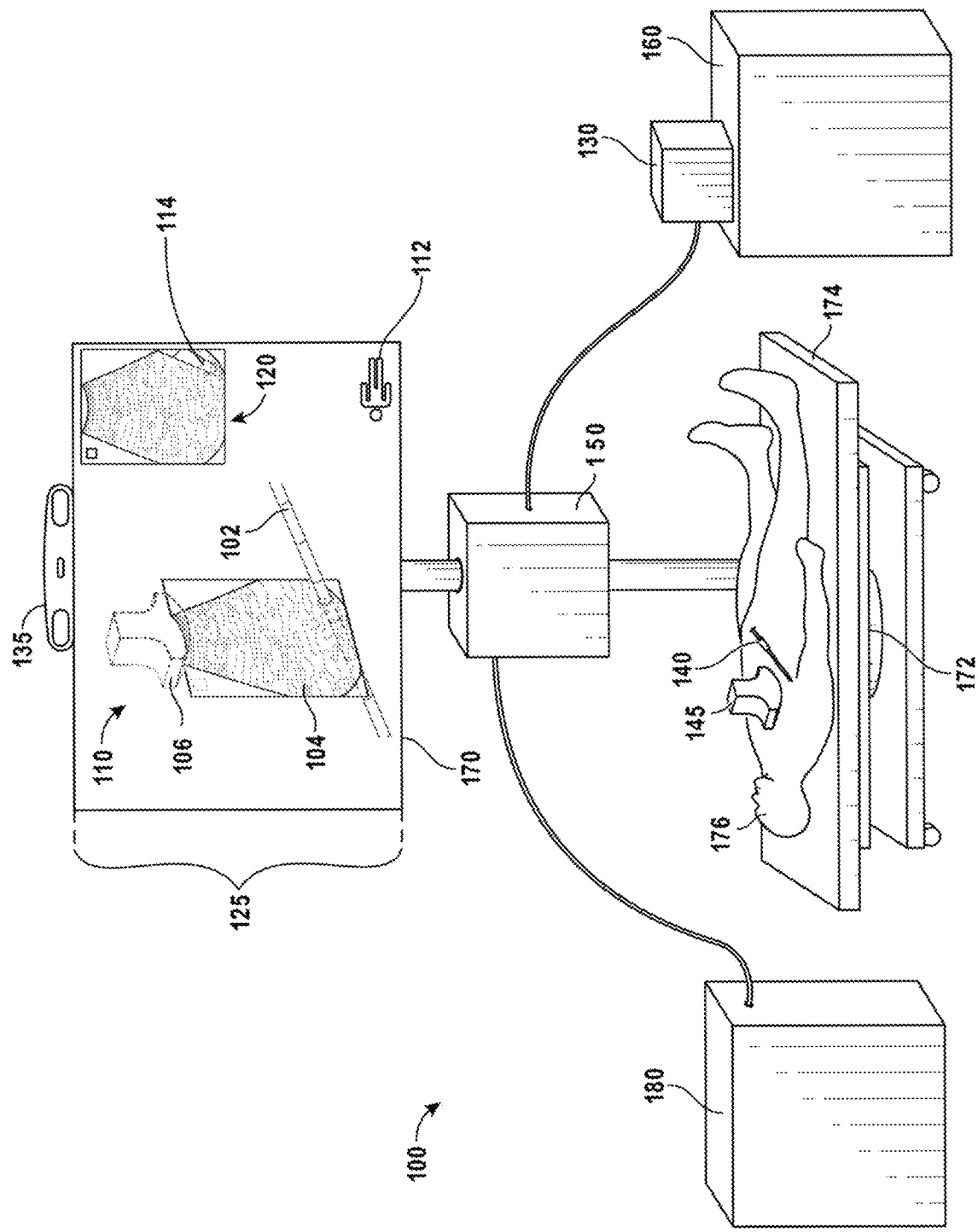
FIG. 1A is a diagram illustrating an embodiment of an image guidance system 100 for image management.

During image-guided medical procedures, displaying image guidance data can aid a healthcare provider in the guidance task. For example, displaying a display object (non-limiting examples: a virtual medical device, a medical image, an affected region of a medical device, or portions thereof) that resembles a physical (non-virtual) device or corresponds to image data captured by a physical device can help healthcare providers associate a virtual scene with the real world and can provide familiar guidance information to the healthcare provider. As another example, displaying image guidance cues (non-limiting examples: trajectory indicators, intersection indicators, or tissue representations) can further aid in the visual guidance of the medical procedure and improve patient care.

During these image-guided procedures, it can be important that the spatial relationships between display objects or other image guidance data is clear and unambiguous so that the healthcare provider can intuitively understand these relationships and safely perform the medical procedures. Misinterpreting the spatial relationships between the image guidance data, or between the healthcare provider and the image guidance data, can potentially lead to patient harm. Nonetheless, it can be common for the healthcare provider to misinterpret or misunderstand the spatial relationships. Systems and methods disclosed herein can facilitate an improved understanding of the spatial relationships during an image-guided medical procedure.

Implementations disclosed herein provide systems, methods, and apparatus for displaying medical images (such as, but not limited to ultrasound, CT, and/or MRI images) for facilitating medical device insertion into tissue by an operator. Certain embodiments pertain to a free-hand medical device guidance system. The system can provide the healthcare provider with manual control over a medical device, while making the spatial relationships between image guidance data (non-limiting examples: display objects, image guidance cues) more intuitive via a visual display. Using this visual feedback, the operator can adjust the medical device's position, orientation, trajectory, or the like. Certain of the contemplated embodiments can be used in conjunction with systems described in greater detail in U.S. patent application Ser. No. 13/014,587, filed Jan. 26, 2011, entitled "Systems, Methods, Apparatuses, and Computer-Readable Media For Image Management In Image-Guided Medical Procedures," U.S. patent application Ser. No. 13/753,274, filed Jan. 29, 2013, entitled "Multiple Medical Device Guidance" (the '274 Application), U.S. patent application Ser. No. 14/212,933, filed Mar. 14, 2014, entitled "Medical Device Guidance," U.S. patent application Ser. No. 14/872,930, filed Oct. 1, 2015, entitled "Affected Region Display Associated With A Medical Device" (the '930 Application), U.S. patent application Ser. No. 15/199,630, filed Jun. 30, 2016, entitled "Loupe Display," U.S. patent application Ser. No. 15/199,711, filed Jun. 30, 2016, entitled "Medical Device Approaches," U.S. patent application Ser. No. 15/415,398, filed Jun. 30, 2016, entitled "Medical Device Navigation Using A Virtual 3D Space," or U.S. patent application Ser. No. 16/052,289, filed Aug. 1, 2018, entitled "Selective Transparency To Assist Medical Device Navigation," each of which is hereby incorporated by reference in its entirety for all purposes.

Medical interventions typically involve using an instrument to insert into, ablate, resect, cauterize, staple, seal, or otherwise manipulate arteries, veins, soft tissue or organs. In general, a healthcare provider must take great care to minimize blood loss and minimize damage to ancillary tissue while performing these tissue-altering interventions. This is even more difficult with minimally invasive surgeries, such as laparoscopic, endoscopic, and robotic surgeries. In some cases, a healthcare provider may use ultrasound to image the internal structures of tissue or an organ before ablating, stapling, transecting, resecting, sealing, grasping, or inserting a medical device into the patient, which can help the healthcare provider avoid critical structures such as blood vessels. However, even with ultrasound imaging, there is a significant possibility of inadvertent damage to surrounding tissue and blood vessels during these procedures. This can be because it is not obvious in the externally displayed medical image where a given internal structure is located relative to the medical device.

The disclosed system can aid a healthcare provider in guiding one or more medical devices through or around tissue of the patient and/or in placing the medical devices. The system can be used to aid in ablating, stapling, transecting, resecting, sealing, grasping and/or inserting a medical device into tissue. In some implementations, the system can be used for treatment of tumors, fibroids, cysts, damaged blood vessels, or other damages to internal structures of a patient. In some implementations, the system can be used for guiding an introducer needle into a vein or an artery. The system can be used during open surgery, laparoscopic surgery, endoscopic procedures, robotic surgeries, biopsies, and/or interventional radiology procedures.

The system can be used in conjunction with data from modalities such as live intraoperative ultrasound, pre-operative computerized tomography (CT), a CT scan, magnetic resonance imaging (MRI), open-magnet MRI, optical coherence tomography ("OCT"), positron emission tomography (PET) scans, fluoroscopy, ultrasound, any cross-sectional medical imaging modality or other preoperative or intraoperative 2D or 3D anatomical imaging data. In addition, the system can use a variety of techniques to determine the position and/or orientation of one or more medical devices. For example, the system can use the NDI Aurora magnetic system, NDI Polaris optical system, etc. In some embodiments, a position sensor can be embedded inside or affixed to each medical device, for example, at the tip, along the shaft, and/or on the handle. Tracking sensors can be built into the medical devices or attached after manufacturing, as described in greater detail in U.S. application Ser. No. 14/212,184, filed Mar. 14, 2014, entitled "Sensor Mount," which is hereby incorporated herein in its entirety.

A medical device can be tracked using one or more of a variety of tracking technologies including, but not limited to, electromagnetic, optical (e.g., retroreflective marker-based, AR marker-based, camera- or depth-camera-based, passive or active markers, SLAM, etc.), mechanical, ultrasound, acoustic, or other tracking technologies. In some cases, each medical device can be associated with one or more tracking sensors, which can continually, or repeatedly, report position and/or orientation, or a single tracking sensor can be used for all the medical devices. In some embodiments, where one tracking sensor is used, the healthcare provider can attach the tracking sensor to the particular medical device that she is intentionally repositioning, and then, once she has placed that medical device, she can remove the tracking sensor and attach it to the next medical device she is repositioning. In some embodiments, the medical devices can be manipulated by the healthcare provider. In certain embodiments, the system can be used with a robotic manipulator, where the robot controls the medical devices. In some embodiments, visually-detectable fiducials can be used to determine or correct position and/or orientation for one or more of the medical devices.

In some embodiments, the handles of medical devices can have push-button switches, to allow the healthcare provider to select a medical device, indicate a tissue target, etc. The handle can also have an indicator light to indicate to the healthcare provider which medical device is selected. Finally, the handle can have an encoder to detect how much how much of an active therapeutic area (e.g. electrode length in some ablative devices) has been exposed by the healthcare provider, and report this information to the guidance system and therapeutic generator.

Image Guidance Systems

FIG. 1A is a diagram illustrating an embodiment of an image guidance system 100 for image management in image-guided medical procedures. As illustrated, the system 100 can include, but is not limited to, a position sensing unit 130, a first medical device 140, a second medical device 145, an image guidance unit 150, an imaging unit 160, a display 170, a surgical or therapeutic system 180, a stand 172, or a surgical table 174. Any of the position sensing unit 130, image guidance unit 150, first medical device 140, second medical device 145, imaging unit 160, display 170, or surgical system 180 can be communicatively coupled to each other, including one-to-one, one-to-many, and many-to-many relationships. It will be understood that the system 100 can include more or fewer elements, such as more or fewer medical devices.

The position sensing unit 130 can be configured to track one or more medical devices, such as the first medical device 140 or the second medical device 145, within a tracking area and can be used to determine an emplacement or pose of the one or more medical devices. The term emplacement as used herein is a broad term and may refer to, without limitation, position and/or orientation or any other appropriate location information. Similarly, the term pose as used herein is a broad term encompassing its plain and ordinary meaning and may refer to, without limitation, position and/or orientation or any other appropriate location information. In some cases, one or more reference room coordinate systems (for example, as described herein with reference to FIG. 1B), can be tracked by the position sensing unit 130, and an emplacement of one or more medical devices, such as the first medical device 140 or the second medical device 145, can be determined with respect to the reference room coordinate system. The position sensing unit 130 can provide emplacement data to the image guidance unit 150.

The position sensing unit 130 can be implemented using one or more of various techniques. For example, a tracking sensor can be mounted, affixed, or coupled in or on one or more medical devices, such as the first medical device 140 or the second medical device 145, and the position sensing unit 130 can track the tracking sensors. In addition or alternatively, a position sensing unit 130 can be implemented as a tracking sensor, and can be attached or affixed to one or more medical devices, such as the first medical device 140 or the second medical device 145. The position sensing unit 130 can include one or more sensing devices (such as the HiBall tracking system, a GPS device, or a signal emitting device) that allow for tracking of the emplacement of a tracking sensor. The term tracking sensor (also referred to as an emplacement sensor), as used herein, is a broad term encompassing its plain and ordinary meaning and includes without limitation all types of magnetic coils or other magnetic field sensing devices for use with magnetic trackers, mechanical trackers, ultrasonic trackers, potentiometers, linear encoders, IMUs, fiducials or other optically detectable markers for use with optical trackers, such as those discussed herein. For example, FIG. 1A illustrates an example optical tracking unit 135, mounted on the display 170.

The position sensing unit 130 can include a magnetic tracker and tracking sensors can be mounted in or on, or coupled to medical devices, such as the first medical device 140 or the second medical device 145. The position sensing unit 130 can include an electromagnetic measurement system (for example, an NDI Aurora system) that uses sensor coils for tracking units attached to one or more medical devices, such as the first medical device 140 or the second medical device 145.

In some implementations, the tracking sensors can be implemented using optical position sensing devices, such as the HiBall tracking system, and the position sensing unit 130 can form part of the HiBall tracking system. For example, the position sensing unit 130 can include an optical 3D tracking system using fiducials. One or more visually-detectable fiducials can be coupled to or otherwise associated with one or more medical devices, such as the first medical device 140 or the second medical device 145. Such optical 3D tracking systems can include the NDI Polaris Spectra, Vicra, Certus, PhaseSpace IMPULSE, Vicon MX, InterSense IS-900, NaturalPoint OptiTrack, Polhemus Fast-Trak, IsoTrak, or Claron MicronTracker2. In addition or alternatively, the system can utilize one or more retroreflective marker-based, AR marker-based, passive or active markers, camera- or depth-camera-based marker (or markerless) tracking systems or algorithms such as ArUco, AR Toolkit, Vuforia, Wikitude, SLAM, or the like.

Tracking sensors can additionally or alternatively include a GPS device or signal emitting device that allows for tracking of the emplacement of the tracking sensor. In some embodiments, a signal emitting device might include a radio-frequency identifier (RFID). In such embodiments, the position sensing unit 130 can use the GPS coordinates of the tracking sensors or can, for example, triangulate the radio frequency signal being emitted by the RFID associated with tracking sensors. The tracking systems can include one or more 3D mice.

In some implementations, the position sensing unit 130 can include an inertial 3D tracking system that includes a compass, accelerometer, tilt sensor, or gyroscope, such as the InterSense InertiaCube or a Nintendo Wii controller. For example, the first medical device 140 or the second medical device 145 can include or have coupled thereto one or more accelerometers, which can be used to estimate movement, position, or location of the medical device. In some embodiments, the position sensing unit 130 can be an Ascension Flock of Birds, Nest of Birds, driveBAY, medSAFE, trakSTAR, miniBIRD, MotionSTAR, pciBIRD, or Calypso 2D Localization System and tracking sensors attached to the medical devices can be magnetic tracking coils.

The position sensing unit 130 can be located in various locations, such as on, beside, above, or below the table 174 or patient 176. For example, in embodiments where the position sensing unit 130 is a magnetic tracker, the position sensing unit 130 can be mounted on or below the table 174. Such an arrangement can be useful when the tracking volume of the position sensing unit 130 is dependent on the location of the position sensing unit 130, as with many magnetic trackers.

Although illustrated in FIG. 1A as a needle, the first medical device 140 can include any invasive medical device for entering a part of the patient 176. For example, the first medical device 140 can include, but is not limited to, a grasper, a stapler, a vessel sealer, an electrocautery device, a resecting device, a transecting device, a scalpel, a biopsy needle, an ablation needle, a surgical needle, an introducer needle, a nerve-block needle, another needle, a catheter, a stent, a laparoscope or laparoscopic camera, implantable hardware, an ultrasound probe (for example, laparoscopic ultrasound probes that enter the patient, Transesophageal echocardiography (TEE), or an ultrasound transducer on the tip of a catheter, needle, or other medical device), or another invasive instrument. In addition or alternatively, the first medical device 140 can include any non-invasive medical device such as, but not limited to, an ultrasound transducer, ultrasound probe, or other external imaging device.

Although illustrated in FIG. 1A as an ultrasound device, the second medical device 145 can include any invasive or non-invasive medical device, such as described above with respect to the first medical device. For example, the second medical device 145 can include an imaging device that provides or aids in the selection of medical images for display. As described herein, in some implementations, the second medical device 145 can include a display, such as an integrated display or a display coupled thereto. Similarly, in some implementations, the first medical device 140 can include a display, such as an integrated display or a display coupled thereto.

The image guidance unit 150 can be used to produce images 125 that are displayed on the display 170. For example, the image guidance unit 150 can receive, process, or combine emplacement data from the position sensing unit 130, information about or from multiple surgical systems 180, information about or from medical devices, such as the first medical device 140, the second medical device 145, or additional medical devices not shown, or other data and can cause the display 170 to display image guidance data, as described herein. As described herein, it will be understood that the same or different images 125, or portions thereof, can be displayed on another display, such as a display that is integrated with or coupled to a medical device. In some embodiments, the other display can display a different perspective of the 3D scene than the display 170.

A healthcare provider can use the image guidance data on display 170 to guide a procedure and improve patient care. As described herein, image guidance data can include display objects or image guidance cues. It will be understood that a display object as used herein is a broad term encompassing, but not limited to, one or more portions of a virtual medical device (e.g., virtual transducer 106, virtual medical needle 102, etc.), one or more portions of an affected region of a medical device, or one or more portions of a medical image (e.g., medical image 104). Embodiments of examples affected regions are described in U.S. patent application Ser. No. 14/872,930, which was previously incorporated by reference. As described herein, a medical image 104 can include or be associated with medical imaging data obtained from a medical device, such as from the first medical device 140, the second medical device 145, or another medical device. For example, a medical image 104 can include data from modalities such as a CT scan, MRI, open-magnet MRI, optical coherence tomography ("OCT"), positron emission tomography ("PET") scans, fluoroscopy, ultrasound, or other preoperative or intraoperative 2D or 3D anatomical imaging data. Further, it will be understood that image guidance cues as used herein is a broad term encompassing, but not limited to, trajectory indicators, intersection indicators, plane indicators, or tissue representations.

Different data of the image guidance data, for example different display objects or image guidance cues, can be displayed concurrently or simultaneously. Reference to displaying image guidance data "concurrently" or "simultaneously" is to be interpreted broadly and may refer to displaying objects in such a way that to a human observer the objects are visible at the same time.

The system can include imaging unit 160, which can be an imaging unit that is in addition to or alternative to image guidance unit 150. For example, imaging unit 160 can be used to produce images that are displayed on a display 170. For example, the imaging unit 160 can receive or process medical imaging data received from an imaging device, which can be the first medical device 140, the second medical device 145, or another medical device. In some embodiments, the imaging unit 160 is an ultrasound machine and the second display is a display associated with the ultrasound machine 160 that displays medical images obtained by the ultrasound machine 160. In some cases, the second medical device 145 can be implemented as a movable imaging device, such as an ultrasound transducer or ultrasound probe. In such examples, the second medical device 145 can be in communication or otherwise connected, via a wireless or wired connection, to the image guidance unit 150 or the imaging unit 160. In some cases, the second medical device 145 can be used by a healthcare provider to select portions of a medical image to show on the display 170 as part of image 125. In some implementations, the position sensing unit 130 is part of the image guidance unit 150 or the imaging unit 160, while in other implementations, the position sensing unit 130 is separate from the image guidance unit 150 or the imaging unit 160.

In the illustrated embodiment, the images 125 include a 2D scene 120 and a 3D scene 110. In the 3D scene 110, at least some image guidance data can be displayed in a 3D space. For example, the illustrated 3D scene 110 includes a medical image 104 (sometimes referred to as medical image slice), a first virtual medical device 102 corresponding to the first medical device 140, a second virtual medical device 106 corresponding to the second medical device 145, and a patient orientation indicator 112. Different, additional, or fewer image guidance data can be displayed in the 3D scene 110.

In the 2D scene 120, some or all of the image guidance data can be displayed as 2D objects. As described herein, in some embodiments, the 2D scene 120 includes a 2D projection of at least a portion of the 3D scene onto a viewplane. In the illustrated example, 2D scene 120 includes a 2D projection of the virtual medical needle 102 (generally referred to a 2D needle 114) onto the 2D plane of the medical image 104. The 2D viewing area can include different or additional image guidance data, as desired, such as one or more image guidance cues. It will be understood that any combination of the image guidance data can be displayed in the 2D view or 3D view as desired. Furthermore, it will be understood that the 2D scene 120 can include 3D objects or the 3D scene 110 can include 2D objects.

The images 125 can be produced on the display 170 by the image guidance unit 150. The display 170 or screen can be implemented using a TV, computer screen, head-mounted display, projector, a stereoscopic display, a display integrated into a medical device (such as the first medical device 140 or the second medical device 145), or a display of a mobile device, such as a phone, laptop, or tablet.

As an example, if the first medical device 140 includes a needle and the second medical device 145 includes an ultrasound probe, then images 125 produced on display 170 can include images, or video, from or corresponding to the ultrasound probe, combined with display objects or image guidance cues. As another example, if the first medical device 140 includes an ultrasound probe 140 and the second medical device 145 includes a laparoscopic camera 145, then images 125 produced on display 170 can include the video from the laparoscopic camera combined with ultrasound data superimposed on the laparoscopic image. The system can additionally or alternatively process or display collected data, such as preoperative CT scans, X-Rays, MRIs, laser scanned 3D surfaces etc.

As noted above, images 125 can be generated based on live, intraoperative, or real-time data obtained using medical device 145, which can be coupled to imaging unit 160. The term real-time as used herein is a broad term and has its ordinary and customary meaning, including without limitation instantaneously or nearly instantaneously. The use of the term real-time can also mean that actions are performed or data is obtained with the intention to be used immediately, upon the next cycle of a system or control loop, or any other appropriate meaning. Additionally, as used herein, real-time data can be data that is obtained at a frequency that would allow a healthcare provider to meaningfully interact with the data during surgery. For example, in some embodiments, real-time data can be a medical image of a patient that is updated one time per second. In some embodiments, real-time data can be ultrasound data that is updated multiple times per second.

In some embodiments, the display 170 displays 3D images to a healthcare provider, such as a physician. Stereoscopic 3D displays separate the imagery shown to each of the healthcare provider's eyes. This can be accomplished by a stereoscopic display, a lenticular auto-stereoscopic display, a head-mounted display, or any other appropriate type of display. The display 170 can be an alternating row or alternating column display. Example alternating row displays include the Miracube G240S, as well as Zalman Trimon Monitors. Alternating column displays include devices manufactured by Sharp, as well as many "auto-stereoscopic" displays (for example, Philips). In some embodiments, Sony Panasonic 3D passive displays and LG, Samsung, or Vizio 3D TVs can be used as well. Display 170 can also be a cathode ray tube. Cathode Ray Tube (CRT) based devices, can use temporal sequencing, showing imagery for the left and right eye in temporal sequential alternation. This method can also be used for projection-based devices, as well as by liquid crystal display (LCD) devices, light emitting diode (LED) devices, or organic LED (OLED) devices.

In certain embodiments, the display 170 can be a head-mounted display worn by the healthcare provider in order to receive 3D images from the image guidance unit 150. In such embodiments, a separate display, such as the pictured display 170, can be omitted. The 3D graphics can be produced using underlying data models, stored in the image guidance unit 150 and projected onto one or more 2D planes in order to create left and right eye images for a head mount, lenticular, or other 3D display. The underlying 3D model can be updated based on the relative emplacements of the various medical devices, such as the first medical device 140 or the second medical device 145, as determined by the position sensing unit(s) 130, or based on new data associated with medical devices. For example, if the second medical device 145 is an ultrasound probe, then the underlying data model can be updated to reflect a most recent medical image. If the first medical device 140 is a stapler, then the underlying model can be updated to reflect any changes related to the jaws, such as information regarding the likely affected anatomy region or angles of the jaws or transecting knife. Any appropriate 3D graphics processing can be used for rendering including processing based on OpenGL, Direct3D, Java 3D, etc. Whole, partial, or modified 3D graphics packages can also be used, such packages including 3DS Max, SolidWorks, Maya, Form Z, Cybermotion 3D, VTK, Slicer, or any others. In some embodiments, various parts of the needed rendering can occur on traditional or specialized graphics hardware. The rendering can occur on the general CPU, on programmable hardware, on a separate processor, be distributed over multiple processors, over multiple dedicated graphics cards, or using any other appropriate combination of hardware.

Images 125 can be produced based on intraoperative or real-time data obtained using the first medical device 140, which can be coupled to a surgical system 180. In the illustrated embodiment of FIG. 1A, the surgical system 180 is shown as coupled to image guidance unit 150. The coupling between the first surgical system 180 and the image guidance unit 150 may not be present in all embodiments. In some embodiments, the coupling between the first surgical system 180 and image guidance unit 150 can be included where information about the first medical device 140 available to first surgical system 180 is useful for the processing performed by image guidance unit 150. For example, in some embodiments, it can be useful to send one or more operating parameters of the first medical device 140 to the image guidance unit 150 so that the image guidance unit 150 can show, highlight, outline or otherwise present an affected region of tissue which is located around a therapy delivery area of the medical device. In some embodiments, the surgical system 180 is not coupled to the image guidance unit 150. Example embodiments including images and graphics that can be displayed are included below.

One or more components, units, devices, or elements of various embodiments can be packaged or distributed as part of a kit. For example, in one embodiment, a medical device, one or more tracking units, 3D viewing glasses, or a portion of an ultrasound wand can form a kit. Other embodiments can have different elements or combinations of elements grouped or packaged together. Kits can be combined or distributed separately from or with the other portions of the system.

Although two medical devices are shown in FIG. 1A, it will be understood that additional or fewer medical devices can be included in the system 100. For example, additional or fewer medical devices can be tracked and associated data can be provided to the image guidance unit 150.

There are numerous other possible embodiments of system 100. For example, many of the depicted components can be joined together to form a single component and can be implemented in a single computer or machine. Further, additional position sensing units can be used in conjunction with position sensing unit 130 to track all relevant medical devices 140 and 145, as discussed in more detail below. Additional imaging units 160 can be included, and combined imaging data from the multiple imaging units 160 can be processed by image guidance unit 150 and shown on display 170. Additionally, two or more surgical systems 180 can also be included. Additionally, one will readily recognize that there are numerous other examples of image guidance systems which can use, incorporate, support, or provide for the techniques, methods, processes, and systems described herein.

Coordinate Systems

Figure 1B:
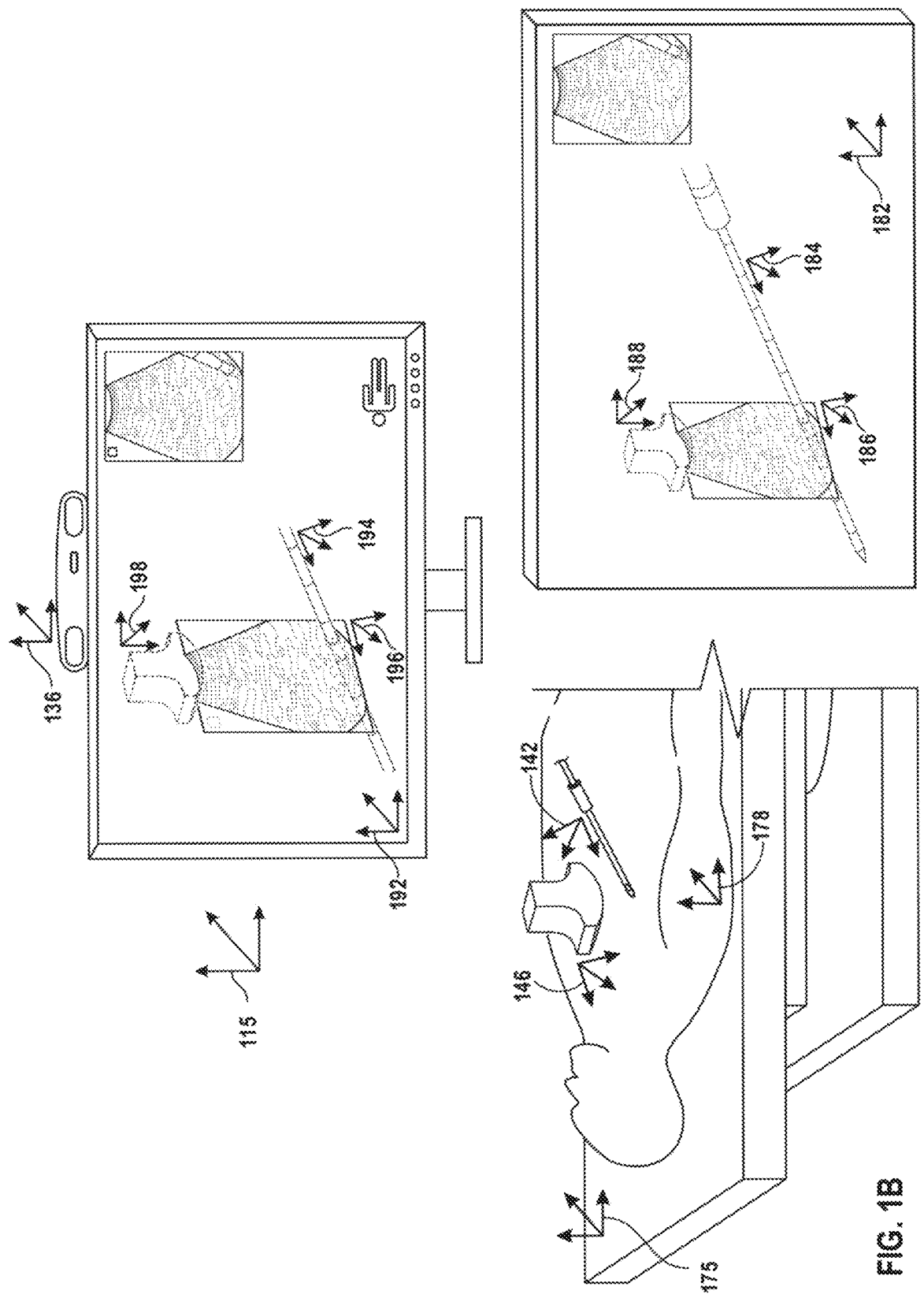
FIG. 1B is a diagram illustrating embodiments of coordinate systems that can be used by the system.

FIG. 1B is a diagram illustrating embodiments of coordinate systems that can be used by the system 100. The system 100 can utilize one or more coordinate systems to track and display the various image guidance data on the display 170. In some cases, one or more coordinate systems can be associated with real objects. For example, with reference to FIGS. 1A and 1B, the coordinate systems can include a table 174 coordinate system 175, a first medical device 140 coordinate system 142, a second medical device 145 coordinate system 146, a patient 176 coordinate system 178, or a room coordinate system 115. In some cases, one or more coordinate systems can be associated with virtual or other objects. For example, the coordinate systems can include a 3D scene coordinate system 182, a first virtual medical device coordinate system 184, a second virtual medical device coordinate system 188, or a medical image coordinate system 186. In addition or alternatively, the coordinate systems can include a display coordinate system 192, or corresponding display coordinate systems 194, 196, or 198 for the first virtual medical device, the medical image, or the second virtual medical device.

As an example, the position sensing unit 130 can determine an emplacement of one or more real objects (for example, the first medical device 140, the second medical device 145, or the like) relative to one or more of the coordinate systems. For example, in some embodiments, an emplacement can be determined relative to the table coordinate system 175, which can be used by a magnetic tracker (not shown) tracking objects within a magnetic field volume, or to the optical tracker 135 coordinate system 136, which can be used by an optical tracker 135 to track one or more objects. As another example, a relative emplacement of a display object can be determined with respect to a different display object or a plane, such as an image plane.

In some cases, multiple coordinate systems can be utilized together. For example, a magnetic position sensing coordinate system 175 can be used in conjunction with magnetic tracker tracking sensor coils within a position sensing region that are coupled to medical devices and an optical position sensing coordinate system 136 can be used in conjunction with an optical tracker 135 tracking a fiducial coupled to a head-mounted display (HMD) or a healthcare provider, or to an optical tracker analyzing an image captured by an image sensor. It will be understood that any combination of the tracker systems or coordinate systems can be used as desired. For example, the position sensing unit 130 can utilize the same coordinate system to track the tracking sensors associated with each of the one or more medical devices or tracking sensors associated with a healthcare provider or HMD. Alternatively, a coordinate system, such as coordinate systems 142 and 146, can be used for each tracking sensor, or any combination thereof.

Room coordinate system 115 can be used to determine the emplacement of objects within a room, such as an operating room. For example, the room coordinate system 115 can be used to determine or identify the relative emplacement of the position sensing unit 130, medical devices 140, 145, tracking sensors, healthcare provider, display 170, etc. relative to each other within a room.

A 3D scene coordinate system 182, which may also be referred to as a 3D volume or scene graph coordinate system, can be used to determine the emplacement of display objects within a virtual 3D scene. In some cases, the 3D scene coordinate system 182 can identify the relative emplacement of virtual objects within the 3D scene. In certain embodiments, the virtual objects can correspond to real objects, such as to medical devices 140, 145 or to computer-generated objects, such as such as trajectory cues. In certain embodiments, display objects can correspond to real objects, virtual objects, or computer generated objects. In addition or alternatively, the 3D scene coordinate system 182 can be used to determine an emplacement of, register an emplacement of, or model one, multiple, or all of the objects in the room, such as the patient, the operating table, the healthcare provider, the display, or the like. In some cases, the display 170 can display a subset of the data associated with the 3D scene coordinate system 182. In some cases, one or more portions of the image guidance data can have an associated coordinate system.

A display coordinate system 192 can be used to determine the emplacement of display objects for display on the display 170. For example, the display coordinate system 192 can be used to determine the emplacement of virtual medical devices, medical images, image guidance cues, or the like, within a display 170. In some embodiments, the display coordinate system 192 can be used to determine how the objects within the 3D scene are to be displayed on the display. For example, the display coordinate system 192 can be used to determine a point-of-view location, or eye point, relative to the 3D scene (or 3D volume coordinate system 182) or scene graph for viewing the contents of the 3D scene. As mentioned above, multiple display coordinate systems 192 can be used. For example, left-eye, right-eye, or center-eye (i.e., a location halfway between the left and right eyes) display coordinate systems can be used to display different perspectives of the display objects within a 3D scene, such as when a 3D display or a head-mounted display (HMD) is being used.

A medical image coordinate system 196 can be used in conjunction with medical images used or processed by the system. As described previously, the medical images can be ultrasound images, CT image, MRI, images, etc. The images can be different sizes or shapes. For example, one ultrasound system can output an image having one size and shape while a different ultrasound system can output an image having a different size or shape. Similarly, CT, MRI, and ultrasound images may have different sizes and shapes. Accordingly, the medical image coordinate system 196 can be used to identify the particular size and shape of the medical image being used or processed by the system 100.

It will be understood that fewer, more, or different coordinate systems can be used as desired. For example, in some embodiments, the 3D scene coordinate system 182 can be omitted or combined with display coordinate system 192 or the table coordinate system 175. The coordinate systems for the tracking sensors, medical devices, or virtual medical devices can be used to identify the dimensions of the sensor/device/display object and relationship of the sensor/device/display object to another sensor/device/display object or other coordinate systems. For example, a medical device coordinate system (or virtual medical device coordinate system) can identify the dimensions of a corresponding medical device or virtual medical device, as well as the emplacement of a tracking sensor relative to the medical device (or vice versa). Similarly, a medical imaging device coordinate system can identify the dimensions of the corresponding medical imaging device (or virtual medical imaging device) or an emplacement of a medical image relative to the medical imaging device (non-limiting example: the emplacement of an ultrasound image relative to the corresponding ultrasound transducer), or vice versa. The system 100 can use various coordinate systems to determine the emplacement of a portion or the entire object with respect to each other and with respect to the other coordinate systems.

The system 100 can use the various coordinate systems to determine emplacement of objects relative to each other or determine how to display the display objects on a display, such as the display 170.

As a non-limiting example, the second medical device 145 can include an ultrasound transducer. To display a virtual rendering 106 of an ultrasound transducer 145 and a medical image 104 on the display 170, the system 100 can determine the emplacement of a magnetic tracking sensor coupled to the ultrasound transducer within a magnetic position sensing coordinate system 175. Using a magnetic tracking sensor coordinate system 175, the system 100 can determine the location of each portion of the magnetic tracking sensor within the magnetic position sensing coordinate system 175. The system 100 can also determine the emplacement of the ultrasound transducer within the magnetic position sensing coordinate system by mapping the coordinate system 146 to the magnetic tracking sensor coordinate system 175 (or vice versa).

In some cases, the system 100 can map the medical image 104 corresponding to the second medical device 145 to the magnetic position sensing coordinate system 175 by mapping a medical image coordinate system to the coordinate system 146 or the magnetic tracking sensor coordinate system 175.

To display the virtual ultrasound transducer 106 and medical image 104, the system 100 can map the various objects from the magnetic position sensing coordinate system 175 to a room coordinate system 115, which can identify the relative emplacement of the coordinate system 175 to a display 170. The system can then map data to the 3D scene coordinate system 182 or the display coordinate system 192. For 3D viewing, the system 100 can map the objects to multiple display coordinate systems 192, such as left-eye or right-eye coordinate systems.

With continued reference to the non-limiting example, the system 100 can determine an emplacement of an optical tracking sensor corresponding to a healthcare provider within an optical position sensing coordinate system 136. The emplacement of the optical tracking sensor within the optical position sensing coordinate system 136 can be mapped to the room coordinate system 115, the 3D scene coordinate system 182, or the display coordinate systems 192 for display. In this way the system 100 can determine the emplacement of the second medical device 145 and medical image 104 relative to the healthcare provider or display the virtual ultrasound transducer 106 or the medical image 104 within the 3D scene relative to the determined emplacement of a healthcare provider.

To display the virtual ultrasound transducer 106 and medical image 104, the system 100 can map the various objects from the magnetic position sensing coordinate system 175 to a room coordinate system 115, which can identify the relative emplacement of the coordinate system 175 to a display 170. The system can then map data to the 3D scene coordinate system 182 or the display coordinate system 192. For 3D viewing, the system 100 can map the objects to multiple display coordinate systems, such as left-eye or right-eye coordinate systems.

Although the non-limiting examples have been described as mapping the various objects and coordinate systems, to a coordinate system 175, the room coordinate system 115, the 3D scene coordinate system 184, or to display coordinate systems 192, it will be understood that one or more of the objects or coordinate systems can be mapped directly or indirectly to any other coordinate system. For example, the medical image 104 can be mapped directly to a left-eye display coordinate system, etc. Thus, any of the real or virtual objects described herein may be represented, detected, or imaged in any coordinate system, and conversion between the various coordinate systems can be performed in components of the system such as image guidance unit 150, position sensing unit 130, an HMD, or other components.

Furthermore, it will be understood that once the system 100 determines an emplacement of a medical device in one coordinate system, such as a coordinate system 175, the system 100 can determine the emplacement of a corresponding virtual medical device in a different coordinate system, such as the 3D scene coordinate system 182 or the display coordinate system 192, by mapping the coordinates of the first coordinate system to the coordinates of the second coordinate system, or vice versa. Accordingly, references made herein to determining an emplacement of the medical device can also refer to determining an emplacement of a virtual medical device corresponding to the medical device, or vice versa. Similarly, references made herein to determining an emplacement of a display object (non-limiting example: medical image) relative to the medical device can also refer to determining the emplacement of the display object relative to a corresponding virtual medical device.

Image Guidance Environment

Various embodiments herein provide image guidance that can help the healthcare provider better understand the scene and relative emplacements or poses of object in the scene, thereby providing improved image guidance.

Figure 2:
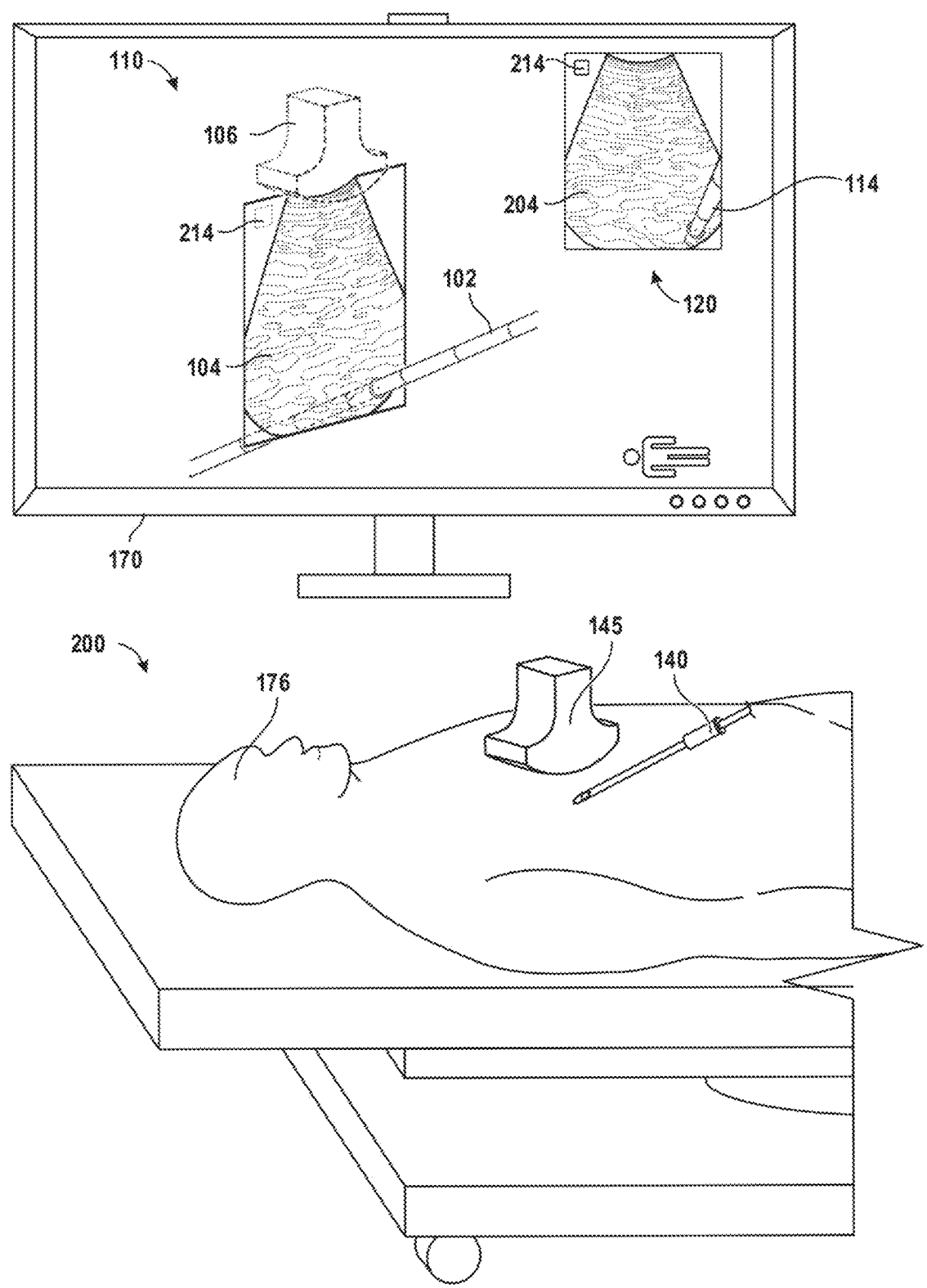
FIG. 2 illustrates an embodiment of an environment for a medical device procedure.

FIG. 2 illustrates an embodiment of an environment 200 for a medical device procedure. As illustrated, the environment 200 includes a patient 176, a first medical device 140, a second medical device 145, and a display 170. The display 170 displays an example 3D scene 110 and an example 2D scene 120.

The 3D scene 110 includes image guidance data such as the virtual medical needle 102, the virtual ultrasound transducer 106, and the medical image 104 displayed in a 3D scene. As described herein, the image guidance data can correspond to one or more real-world objects. For example, the virtual medical needle 102 can correspond to the first medical device 140, the virtual ultrasound transducer 106 can correspond to the second medical device 145, and the medical image 104 can correspond to image data associated with the second medical device 145.

The 3D scene 110 can be displayed on the display 170 as if the viewer of the display is viewing the 3D scene 110 from a particular point-of-view location or vantage point. For example, the display 170 can act as a window from which the 3D scene 110 can be viewed, and the point-of-view location can refer to the location of the window relative to the 3D scene 110. In some embodiments, as described in greater detail in U.S. patent application Ser. No. 14/212,933, which was previously incorporated herein by reference, the point-of-view location can be a fixed location (such as centered in front of the display 170), a predetermined distance/angle from the display 170, or a location configured by the healthcare provider. In some cases, the point-of-view location can be dynamic. For example, point-of-view location can be based at least in part on an emplacement of a real-world object, such as a medical device, a tracking sensor, or a head-mounted display. In some cases, the point-of-view location can be based on an actual, expected, or desired location of a healthcare provider. For example, a system can track a healthcare provider in real-time and determine the point-of-view location based at least in part on the tracked location of the healthcare provider.

One or more of the display objects in the 3D scene 110 can be implemented as a virtual medical device (sometimes referred to as an avatar). For example, a virtual medical device displayed in display 170 can resemble the real medical device to which it corresponds. Some models of medical devices have markings such as bands around the shaft to indicate distance along the shaft. Healthcare providers performing medical device procedures are often familiar with these markings and can use them to help understand the spatial relationship between the medical device and anatomy. The make and model of a medical device can be known to the image guidance system 100, and a virtual medical device displayed in display 170 can resemble the real medical device to which it corresponds. For example, the virtual medical device 102 can resemble the real medical device 140. Similarly, the virtual medical device 106 can resemble the real medical device 145. Accordingly, it will be understood that the terms medical device and virtual medical device can sometimes be used interchangeably, as they can generally relate to the same object. That is, the medical device relates to the object in the real world and virtual medical device relates to a representation of the object, such as an avatar, in virtual space.

By displaying a virtual medical device that resembles a real medical device, the system can advantageously aid healthcare providers in associating the image guidance data with the real world. Furthermore, the more the healthcare provider is familiar with the guidance information, the more he or she is aided in the guidance task. For example, the healthcare provider can see the familiar markings on the medical device 102 being displayed on the display 170 and therefore be familiar with the distance and relative placement of the displayed medical device 102 with respect to other data, such as tissue seen in the medical image 104. This knowledge of relative placement of items being displayed can help the healthcare provider move a real medical device into place.

The features of the real medical device that can be rendered in the 3D scene 110 can include, but are not limited to, the overall shape (for example, diameter, angles, cross sectional shape, curvature, etc.), color, distance markers, angle of the jaws, visuals or echogenic fiducial markers, the state of deployable elements such as tines, paddles, anchors, resection loops, stiffening or steerable sleeves, temperature, radiation, light or magnetic field sensors, lens, waveguides, fluid transfer channels, and the like. The type of medical device being used can be an input into the image guidance system 100. For example, it can be a user input to the system or can be determined by the system. For instance, the medical device type can be detected by a camera or other device, can be received as data from an attached medical device, such as surgical system 180 in FIG. 1, or the information can be received in any other appropriate manner. Alternatively, the type of medical device can be can be a system default.

As another example, consider the physical markings that can be on the instruments themselves. These markings can help orient a healthcare provider during use of the instrument. In some embodiments, the image guidance unit can represent these markings in the images displayed in the display. For example, certain ultrasound transducers are built with an orientation mark (for example, a small bump) on one side of the transducing array. That mark can also be shown in the medical image on the scanner's display, to help the healthcare provider understand where the scanned anatomical structures shown on screen are located under the transducer, inside the patient.

As described herein, the image guidance data can be displayed in the 3D scene 110, with the display 170 acting as a window into virtual 3D space. The emplacement of a virtual medical device within the 3D scene 110 can match or correspond to the emplacement of a corresponding real medical device. For example, if the first medical device 140 is moved to the right with respect to a point-of-view location, the virtual medical device 102 can also move to the right in the display 170. Similarly, if the first medical device 140 is rotated or oriented such that its tip is pointing away from the point-of-view location, the virtual medical device 102 can likewise show the change in orientation. For example, the display 170 can show the tip of the virtual medical device 102 in the background and the other end of the virtual medical device 102 in the foreground, such that the tip of the virtual medical device 102 is pointing into the display 170. Similarly, emplacement of the second virtual medical device 106 or the medical image 104 within the 3D scene 110 can match or correspond to the emplacement of the second real medical device 145.

Once tracked and displayed, a healthcare provider is able to see image guidance data on display 170 that will allow her to know the relative pose, location, or emplacement of the tracked instrument(s) with respect to one another or with respect to imaging data and will be able to see, on display 170, the features of the instrument rendered in the scene.

With continued reference to FIG. 2, in some embodiments, the display 170 can display a 2D scene 120 in addition to or alternatively to the 3D scene 110. As described herein, the 2D scene 120 can include 2D projection of at least a portion of the 3D scene 110 onto a 2D plane. In the illustrated embodiment, the 2D scene 120 includes a 2D medical image and a 2D needle 114, which In some cases, the 2D scene 120 can be similar to what a healthcare provider is accustomed to seeing with traditional medical displays, such as ultrasound displays. This can be useful by presenting to the healthcare provider the imaging to which she is accustomed and allows a healthcare provider to see the medical data regardless of the then-current emplacement of the imaging device with respect to the healthcare provider.

In the illustrated embodiment, the 2D scene 120 is depicted in the upper right corner of the display 170. However, it can be placed in any location. For example, the guidance system 100 can automatically or continually choose a corner in which to render the 2D scene 120, for example, based on the position of the display objects in the 3D scene 110. For example, in FIG. 2, the needle 140 can be held in the healthcare provider's right hand and the needle's shaft can be to the right of the 3D view of the medical image. In this example, the 2D view 202 of the medical image is in the upper right corner of display 170 so that it does not cover any of the 3D features of the 3D scene 110 and the 3D scene 110 does not cover any of the features of the 2D scene. However, in some cases, to prevent the 2D scene 120 from covering or overlapping with the 3D scene 110, the system can automatically move the 2D scene 120 to a corner or position that would not otherwise be occupied by graphics or data.

The system can attempt to avoid having the 2D scene 120 quickly move among corners of the display in order to avoid overlapping with graphics and data in the display. For example, a function f can be used to determine which corner is most suitable for the 2D scene 120 to be drawn in. The inputs to f can include the locations, in the screen coordinate system, of the displayed medical device tip, the corners of the 3D scene 110, etc. In some embodiments, f s output for any given point in time is independent of f's output in the previous frames, which can cause the medical image to move among corners of the display rapidly. In some embodiments, the image guidance system will filter f's output over time. For example, the output of a filter g, for any given frame, could be the corner, which has been output by f the most number of times over the last n frames, possibly weighting the most recent values for f most heavily. The output of the filter g can be used to determine in which corner of display 170 to display the 2D scene 120 and the temporal filtering provided by g can allow the 2D scene 120 display to jump less frequently, moving more smoothly among the corners of the display 170.

In some embodiments, virtual information or image guidance cues can be overlaid on the 2D scene 120 or the 3D scene 110. For example, the 2D scene 120 or the 3D scene 110 can include an orientation indicator 214. In some embodiments, the orientation indicator 214 is a symbolic 3D representation of an orientation of the medical image 214. An example of this orientation indicator 214 is displayed in FIG. 2, where a small rectilinear volume 214 is shown in the 3D scene 110 and the 2D scene 120. In some embodiments, the orientation indicator 214 corresponds to a feature, such as a physical marking, of the ultrasound probe. In some embodiments, the orientation indicator 214 is displayed to provide assistance in associating the 3D scene 110 and the 2D scene 120.

It will be understood that the medical image 104 can correspond to image data received from an imaging device, such as an ultrasound transducer. In some embodiments, the image data can correspond to a cross-section of tissue having a certain thickness. In some instances, the imaging device can compact the image data, or treat the image data as 2D data, such that there is no perceived thickness. In certain embodiments, when the medical image 104 is displayed in the 3D scene 110, the system can treat the medical image 104 as a 2D or quasi 2D object. In such embodiments, the system can cause the medical image 104 to have little to no perceptible thickness. Accordingly, in certain embodiments, when the medical image 104 is oriented orthogonally or perpendicularly with respect to a point-of-view location, the system can cause the display to display nothing or a line having a relatively small thickness, such as a few pixels, etc. In some cases, the number of pixels used to display the relatively small thickness of the medical image 104 can be a function of the size of the display 170. For example, more pixels can be used for a larger display and fewer pixels can be used for a smaller display, etc.

Furthermore, it will be understood that other image guidance cues can be generated and displayed on the display as described in greater detail in the '274 Application, previously incorporated herein by reference. For example, the system 100 can generate or display graphical indicators that help indicate the spatial relationship between a medical device and a medical image plane (for example, graphical image plane indicators) or other plane (for example, graphical plane indicators), indicators to indicate the relative positions of the medical device(s) and medical image(s), features of interest, annotations, plane indicators, plane intersection indicators, other graphical indicators, approximate medical device location indicators, etc. As described in greater detail above and in the '274 Application, the various image guidance cues can be generated based at least in part on the emplacement information of the medical devices used with the system 100.

Medical Device with Communicatively Coupled Display

Figure 3C:
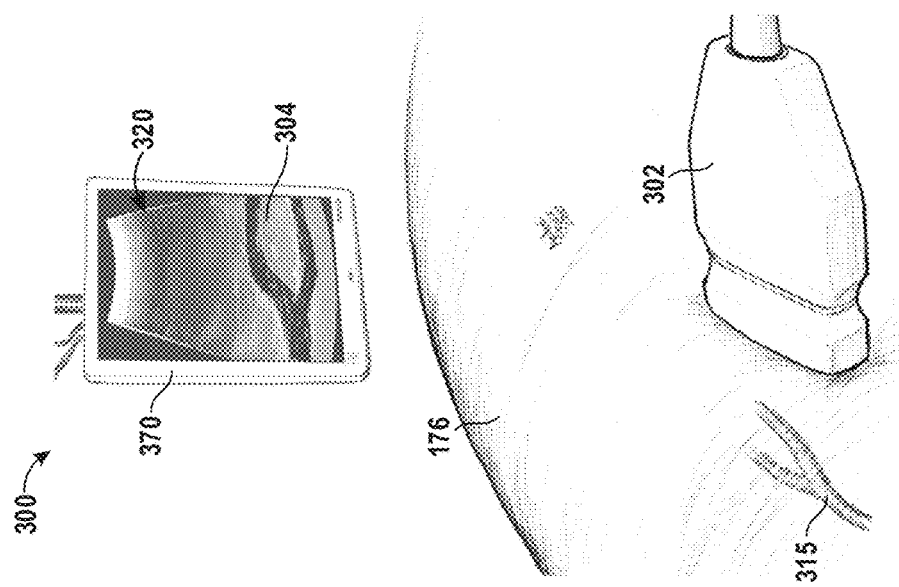
FIGS. 3A-3C illustrate an example environment for a medical device procedure.
Figure 3B:
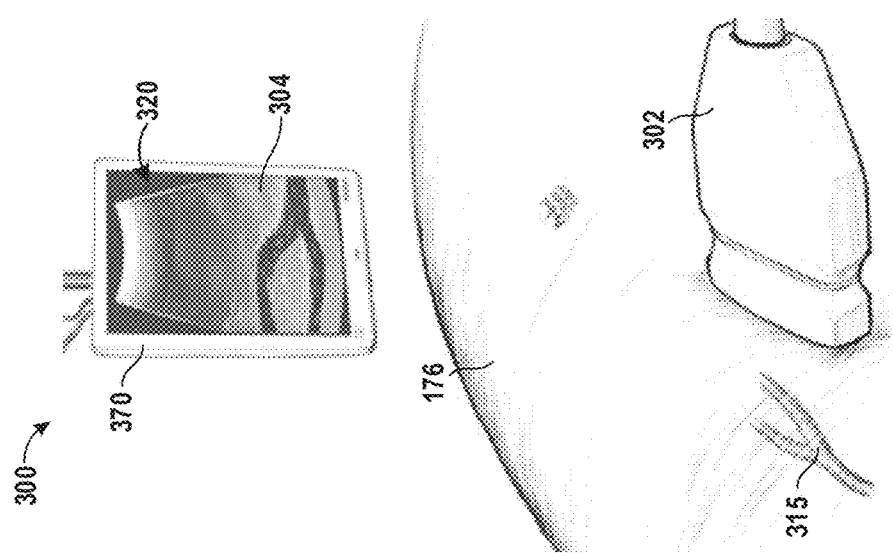
Figure 3A:
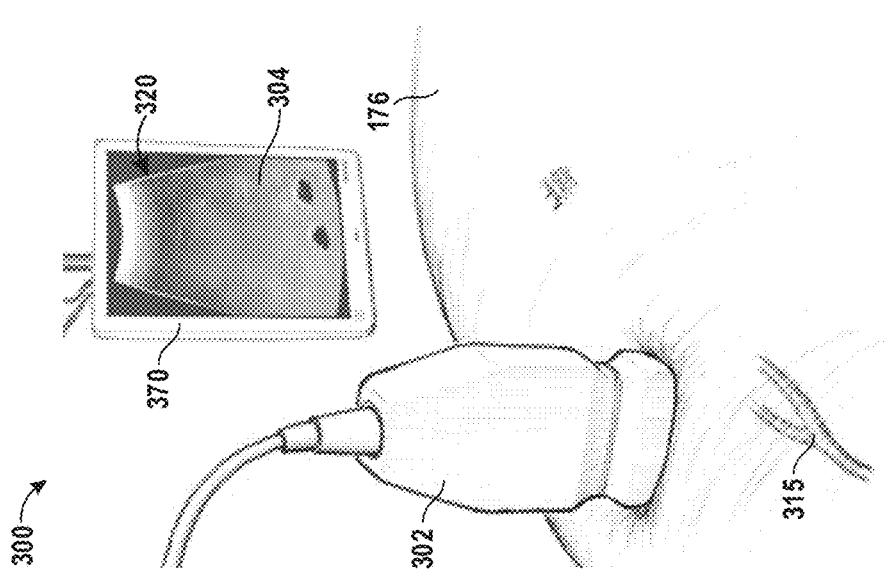

FIGS. 3A-3C illustrate an example environment 300 for a medical device procedure. The environment 300 includes a medical imaging device 302 that is imaging tissue of a patient 176 and further includes a display 370 that displays a 2D scene 320 that includes a medical image 304. In each of FIGS. 3A-3C, the medical imaging device 302 is oriented/positioned to image at least a portion of the internal anatomy 315. The medical imaging device 302 can be an embodiment of the first medical device 140 or the second medical device 145 of FIGS. 1A-2; the 2D scene 320 can be an embodiment of the 2D scene 120 of FIGS. 1A-2; the medical image 304 can be an embodiment of the medical image 104 of FIGS. 1A-2; or the display 370 can be an embodiment of the display 170 of FIGS. 1A-2. Furthermore, it will be understood that the internal anatomy 315 is shown for illustrative purposes only and is not generally viewable due to its location beneath the skin of the patient 176.

In the illustrated environment 300, the medical imaging device 302 is implemented as an ultrasound transducer. In some implementations, the medical imaging device 302 can be controlled by a processor (not shown) to image a region of tissue of the patient 176. For example, a processor in communication with the medical imaging device 302 can cause the medical imaging device 302 to emit sounds waves into a region of tissue and receive image data corresponding to echoes of the sound waves after the sound waves are emitted into the region of tissue. A processor in communication with the medical imaging device 302 can process the image data to determine the medical image 304, and the processor can cause the medical image 304, or a portion thereof, to be displayed on the display 370. In some embodiments, the medical image 304 can be a slice of a 3D medical image.

The content of the 2D scene 320 on the display 370 is different for each of FIGS. 3A-3C. This is due, at least in part, to the pose of the medical imaging device 302 when it images the tissue. For example, FIG. 3A illustrates the medical imaging device 302 located above the internal anatomy 315. It follows that the medical image 304 of FIG. 3A shows an ultrasound slice of the internal anatomy 315 corresponding to a vertical cross-section of the internal anatomy 315. FIGS. 3B and 3C illustrate the medical imaging device 302 located to the side of the internal anatomy 315. It follows that the medical image 320 of FIGS. 3B and 3C shows an ultrasound slice of the internal anatomy 315 corresponding to a lateral cross-section.

In each of the examples of FIGS. 3A-3B, the display 370 (and, as a result, the medical image 304) remains in an arbitrarily fixed pose during the image-guided procedure. Thus, as the medical provider moves the medical imaging device 302 during the procedure, the medical provider must mentally manipulate the medical image 304 to understand which part of the patient is shown and from which perspective it is shown. For example, assume the medical provider moves the medical imaging device 302 from its pose in FIG. 3A to its pose in FIG. 3B. As the medical imaging device 302 moves, the medical image 304 updates to show the presently imaged region of tissue. However, to understand the spatial relationship between the medical image 304 and the imaged region, the medical provider must mentally adjust the pose of the medical image 304 to match the pose of the tissue scanning geometry of the medical imaging device 302. This mental manipulation requirement can lead to a misunderstanding of the spatial relationships between the medical image 304 and the medical provider's medical tools, which can potentially lead to patient harm.

Furthermore, even if the medical provider successfully performs the required mental manipulation, the spatial relationships of the imaged tissue and the medical tools may remain ambiguous. For example, although the medical imaging device 302 appears to have the same pose in both FIGS. 3B and 3C, the medical image 120 of FIG. 3B is horizontally flipped as compared to the medical image 120 of FIG. 3C. This flipping of the medical image 120 can occur as a result of any of various circumstances, such as the medical device 145 being rotated 180 degrees around an axis that includes the scanning plane. As another example, many ultrasound transducers have an option to flip the scanning plane. As a result, the medical provider can unintentionally adjust the scanning plane such that her mental manipulations are inaccurate.

To address these or other problems, in some embodiments, the display 370 can be communicatively coupled to the medical imaging device 302. As a result, the pose of the display 370 (and thus the medical image 304) can match or correspond to the pose of the medical imaging device 302, which can reduce or remove the requirement that the medical provider mentally manipulate the medical image 304 to perform the procedure, thereby improving the medical provider's understanding and treatment efficacy.

Figure 4B:
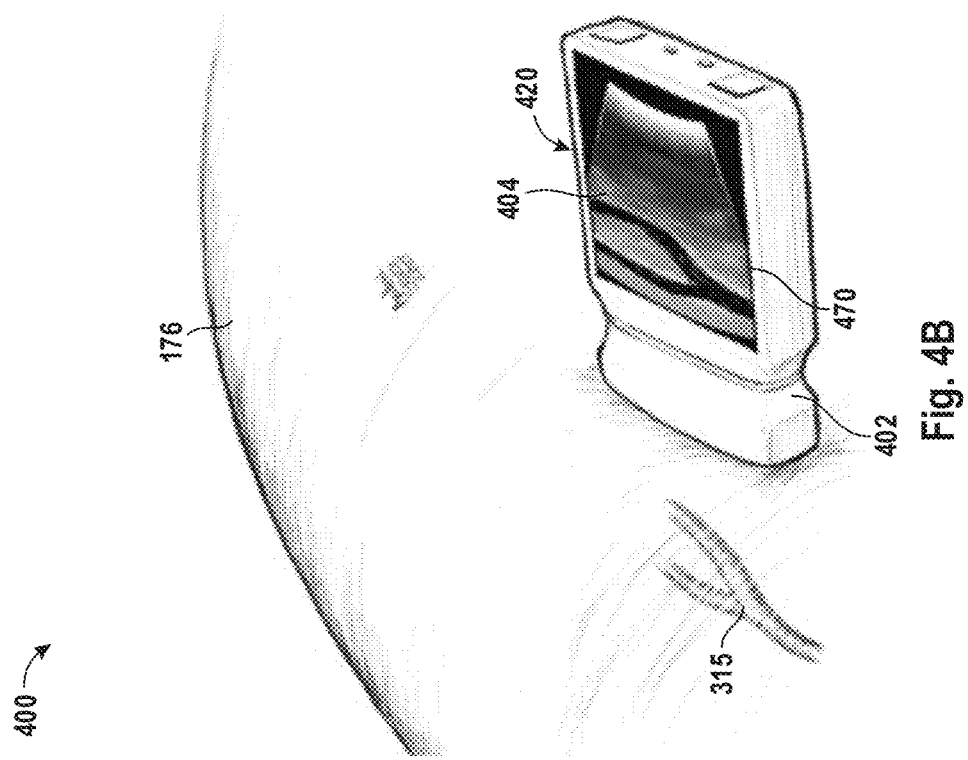
FIGS. 4A and 4B illustrate an example environment for a medical device procedure.
Figure 4A:
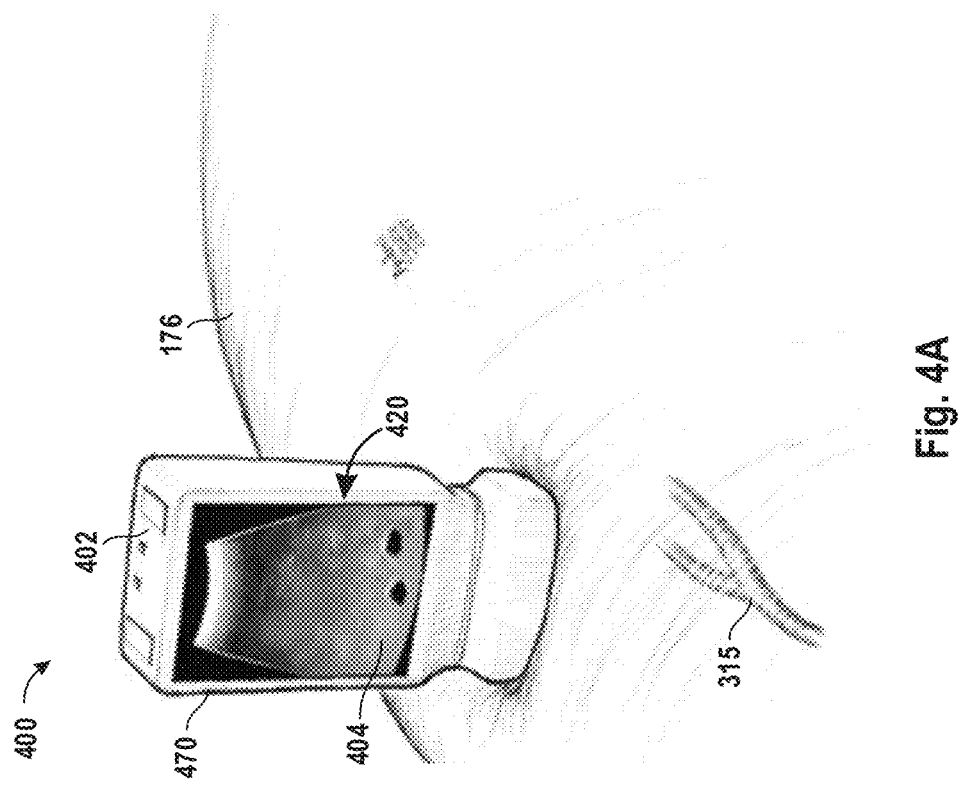

FIGS. 4A and 4B illustrate an example environment 400 for a medical device procedure. The environment 400 includes a medical device 402 with a communicatively coupled display 470. The medical device 402 can be an embodiment of the medical imaging device 302 of FIGS. 3A-3C and the display 470 can be an embodiment of the display 370 of FIGS. 3A-3C.

In the illustrated example, a viewing area of the display 470 (which can be referred to as a viewing screen) can be aligned such that it is parallel to the 2D region (in this case, a tissue cross-section) that is imaged by the medical device 402. As a result of this alignment, the pose of the display 470 (and thus the 2D scene 420, which includes a medical image 404) changes with the pose of the medical device 402. In some cases, this alignment makes clear the spatial relationship between the pose of the medical device 402 and the medical image, which can increase the likelihood of the medical provider intuitively understanding the spatial relationships between the medical image 404 and the medical device 402. For example, the alignment can provide the medical provider with a display 470 that has a pose that is related to her point-of-view, which can limit a need for the medical provider to perform mental manipulations to understand the internal anatomy 315 of the patient 176. In some cases, for example as illustrated in FIGS. 4A and 4B, the display 470 is aligned such that the medical image 404 is parallel to, but offset from the region imaged by the medical device 402. For example, in some cases, a plane of the region imaged by the medical device 402 bisects the medical device 402. In instances such as these, the screen of the display 470 is parallel to the plane of the region imaged by the medical device 402, but is offset by an amount equal to half of a thickness of the medical device 402. In some embodiments, the medical image 404 is coplanar with the region imaged by the medical device 402. For example, the medical device 402 can be designed such that a screen of the display is on the same plane as the plane of the region imaged by the medical device 402.

In some embodiments, a pose of the display 470 or a viewing screen of the display 470 can be adjustable. In some cases, the pose can be manually adjusted, for example, by a medical provider. For example, the display 470 can be mounted to the medical device 402 via an adjustable mount that allows the pose of the display 470 to be adjusted by a user. As another example, in some cases, the pose can be adjusted automatically by the medical device 402. For example, medical device 402 can include a gyroscope or other orientation detector and a processor can cause an adjustment the pose of the display 470 based on the data from the gyroscope. As a result, in some cases, the display is not aligned to be parallel to the 2D region that is imaged by the medical device 404. For example, in some cases, the display 470 can be adjusted to be aligned with the patient's body or to be within the view of the medical provider's eyes.

The display 470 is communicatively coupled to the medical device 402. For example, the display 470 can be integrated into the medical device 402, such as in a housing of the medical device. As another example, the display 470 can be coupled or attached to the medical device 402. For instance, medical device 402 can include a display-less ultrasound transducer coupled to the display 470. In some cases, the medical device 402 can include a display-less ultrasound transducer that is configured to couple to a device with an integrated display such as, but not limited to, a mobile phone, a laptop, a tablet, a phablet, an iPod, or the like. In some cases, the medical device 402 can be configured to wirelessly connect to the device with the integrated display. In some cases, the medical device 402 can be configured to connect to the device with the integrated display or via a standard connector, such as a Lightning or USB-C connection. In some cases, processing can be performed by a processor associated with the ultrasound transducer or a processor associated with the device with the integrated display.

Although, in this example, the medical device 402 is implemented as an imaging device, it will be understood that the medical device 402 can include any type of medical device such as, but not limited to, a medical needle, a scalpel, a catheter, a stent, a laparoscopic camera, or a multi-axis device, such as a stapler, a grasper, a transecting device, a resecting device, or a vessel sealer.

In some embodiments, the medical device 402 can include more than one display, such as a display on each side of the medical device 402 so that the 2D scene 420 can be viewed from either side. In some embodiments, the display 470 includes a see-through display or a single display that can be viewed from both sides. For example, a see-through display may be mounted centrally in the housing of the medical device 402.

2D Scene

In some instances, it can be difficult to discern the content of a 3D scene from a 2D depiction of it. For example, in many cases, a 2D depiction can cause objects to appear flattened onto a 2D plane, which can give an impression that the objects are coplanar when in fact the objects are likely not coplanar. This perceived co-planarity can be confusing, as it can misrepresent a true spatial relationship between the objects in the 3D scene. For at least these reasons, in some cases, it can be advantageous to display a 3D depiction of the 3D scene to provide image guidance that can help the healthcare provider understand the 3D scene and relative emplacements of objects in the scene. For example, as described herein, the 3D scene 110 of FIG. 1A can act as a window into a virtual 3D space where a viewer can see and easily understand the relative emplacements of the objects in the 3D scene 110.

In some circumstances, however, a 2D depiction of the 3D scene may provide improved image guidance over a 3D depiction of the 3D scene. For example, in some cases, displaying a 3D depiction of a 3D scene can demand a relatively large display. Otherwise, the size of the content displayed can be difficult to see or understand. In contrast, a smaller display may not substantially affect a user's ability to discern the content of a 2D depiction of the 3D scene because, for example, the 2D depiction can focus on particular content of the 3D scene, rather than the whole scene. Therefore, various embodiments herein provide an improved 2D scene to be presented on a display for image guidance, which can improve image guidance such that a healthcare provider can easily or intuitively understand spatial relationships between objects within the 2D scene. For example, in some cases, at least a portion of the 2D scene can be produced using one or more projection or mapping techniques.

Orthographic Projection

In some embodiments, a 2D scene, as described herein, can be produced or determined using orthographic projection techniques. For example, based at least in part on projecting lines that are orthogonal to a selected viewplane, the orthographic projections of various image guidance data can be determined. In some cases, a 2D scene can be created by mapping or compositing the orthographic projections onto the selected viewplane, which in many cases can be the 2D plane associated with the medical image.

Figure 5A:
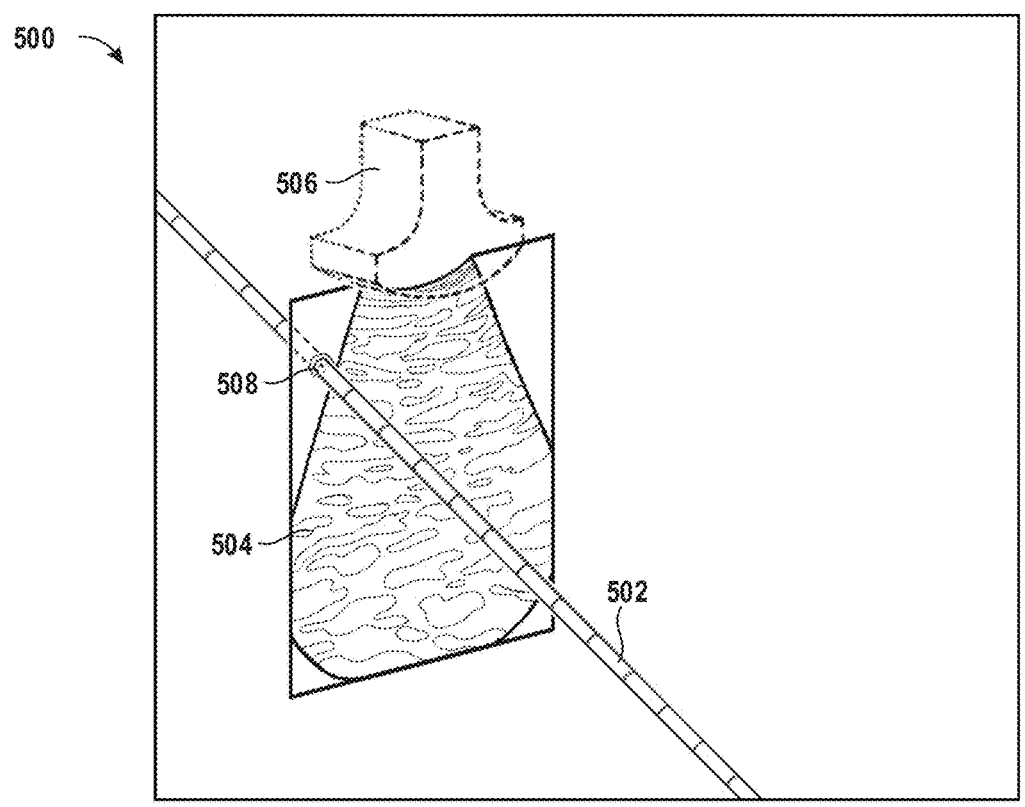
FIG. 5A illustrates an example virtual 3D scene.

FIG. 5A illustrates an example virtual 3D scene 500 that includes various image guidance data such as a virtual ultrasound transducer 506, a medical image 504 positioned at a transducing lens of the virtual ultrasound transducer 506, and a virtual medical needle 502 that traverses the medical image 504 at intersection point 508. The virtual medical needle 502 can be an embodiment of the first medical device 140, the virtual ultrasound transducer 506 can be an embodiment of the second medical device 145, and the medical image 504 can be an embodiment of the medical image 104 of FIGS. 1A-2. As described herein, it will be understood that the virtual 3D scene 500 can correspond to a real 3D environment. For example, some or all of the various image guidance data in the virtual 3D scene 500 can correspond to real-world, physical objects or images produced by those real world, physical objects.

Figure 5B:
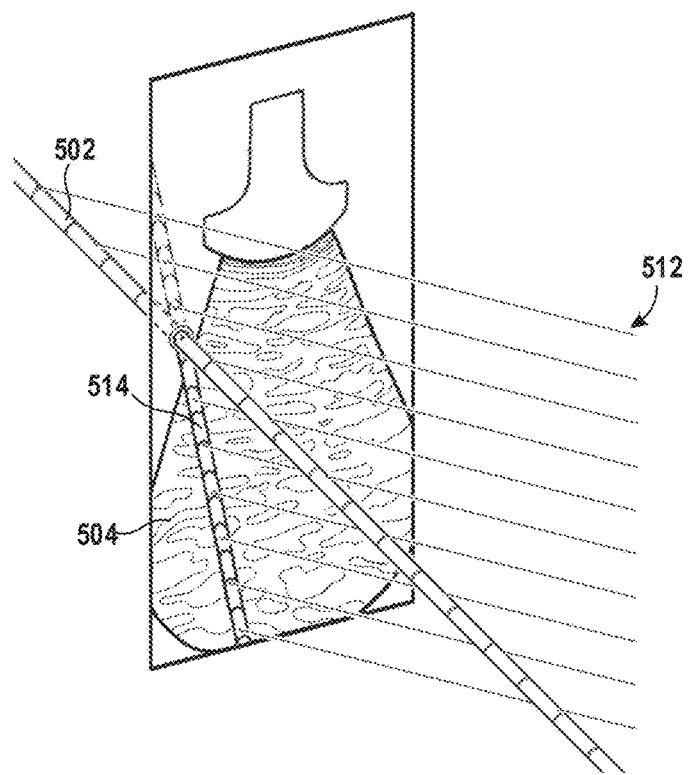
FIG. 5B illustrates a diagram that is useful for explaining a process for determining a projection of a display object onto a 2D plane using orthographic projection techniques.

FIG. 5B illustrates a diagram that is useful for explaining a process for determining a projection of the virtual medical needle 502 onto the medical image 504 using orthographic projection techniques. The diagram includes a plurality of projecting lines 512 that are orthogonal to a 2D plane of the medical image 504 and that intersect or meet both the virtual medical needle 502 and the medical image 504. In some cases, the projection of the virtual medical needle 502 can be identified or formed based at least in part on the intersections of the projecting lines 512 with the medical image 504. For example, the projection of the virtual medical needle 502 can be identified or formed by aggregating some or all of the intersections. An example orthographic projection 514 is illustrated on the medical image 504.

Figure 5C:
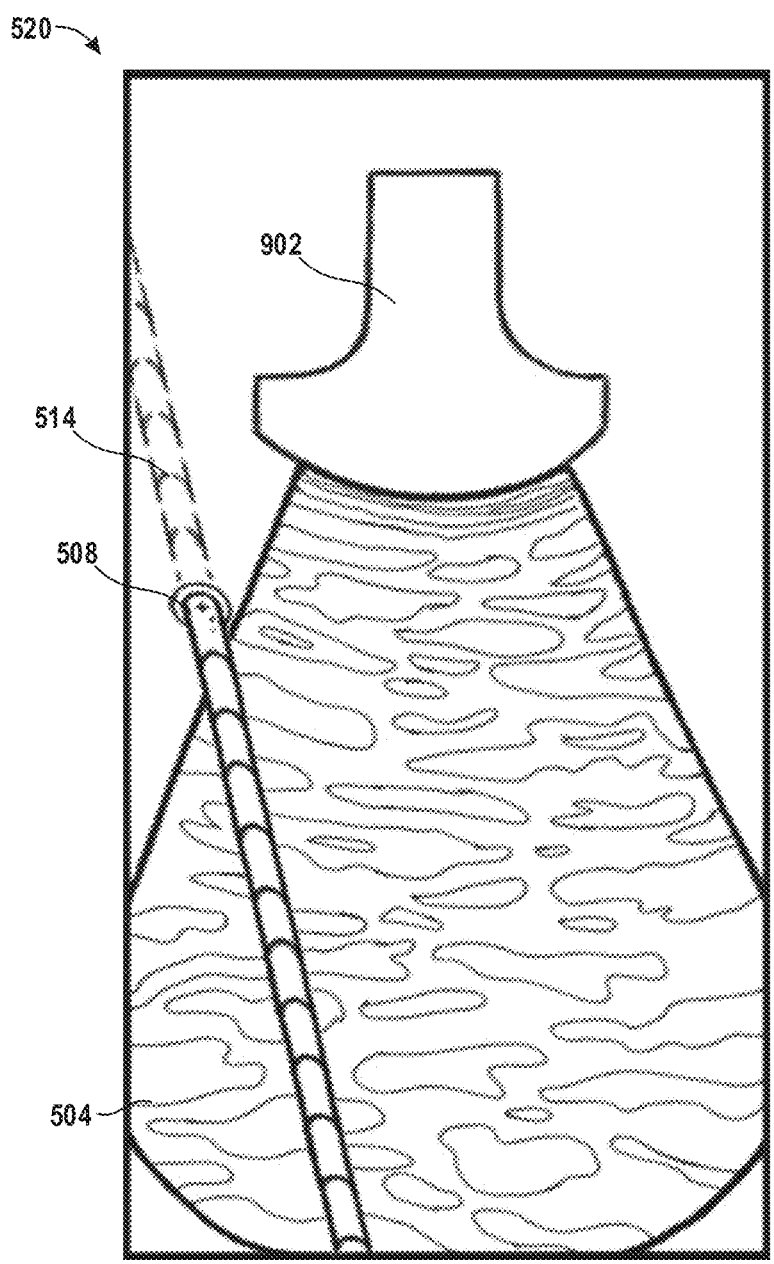
FIG. 5C illustrates an example 2D scene that includes a medical image and an orthographic projection of a display object onto the 2D image slice.

FIG. 5C illustrates an example 2D scene 520 that includes the medical image 504 and an orthographic projection 514 of the virtual medical needle 502 onto the medical image 504. As shown, the result of the orthogonal projection is a flat geometric structure that can be directly mapped onto a display, such as display 170 of FIG. 1A or display 470 of FIG. 4A.

As illustrated from a comparison of FIG. 5A and FIG. 5C, the orthographic projection 514 of the virtual medical needle 502 does not look the same as the virtual medical needle 502. That is also evidenced in the projection geometry illustrated in FIG. 5B, which includes both the virtual medical needle 502 and the orthographic projection 514. However, despite the difference in appearance, the orthographic projection 514 intuitively provides a viewer with information regarding the pose of the virtual medical needle 502. For example, from the 2D scene 520, it can be seen that the needle (e.g., the orthographic projection 514) traverses the medical image 504 at intersection point 508. Furthermore, based at least in part on the 2D scene 520, a viewer can intuitively tell that the needle (e.g., the orthographic projection 514) traverses the medical image 504 at an upward angle.

In some cases, the medical image 504 or the 2D scene 520 can be adjusted to fit the size of the display. For example, the medical image 504 or the 2D scene 520 can be stretched, scaled, or otherwise resized to fit the dimensions of a display. In some cases, the medical image 504 or the 2D scene 520 does not completely fill a viewing area of a display. For example, the medical image 504 or the 2D scene 520 can retain its aspect ratio when presented on the display. In some cases, the medical image 504 or the 2D scene 520 can be adjusted so that the 2D transducer 902 is fully or mostly cropped out of the 2D scene 520.

Figure 6A:
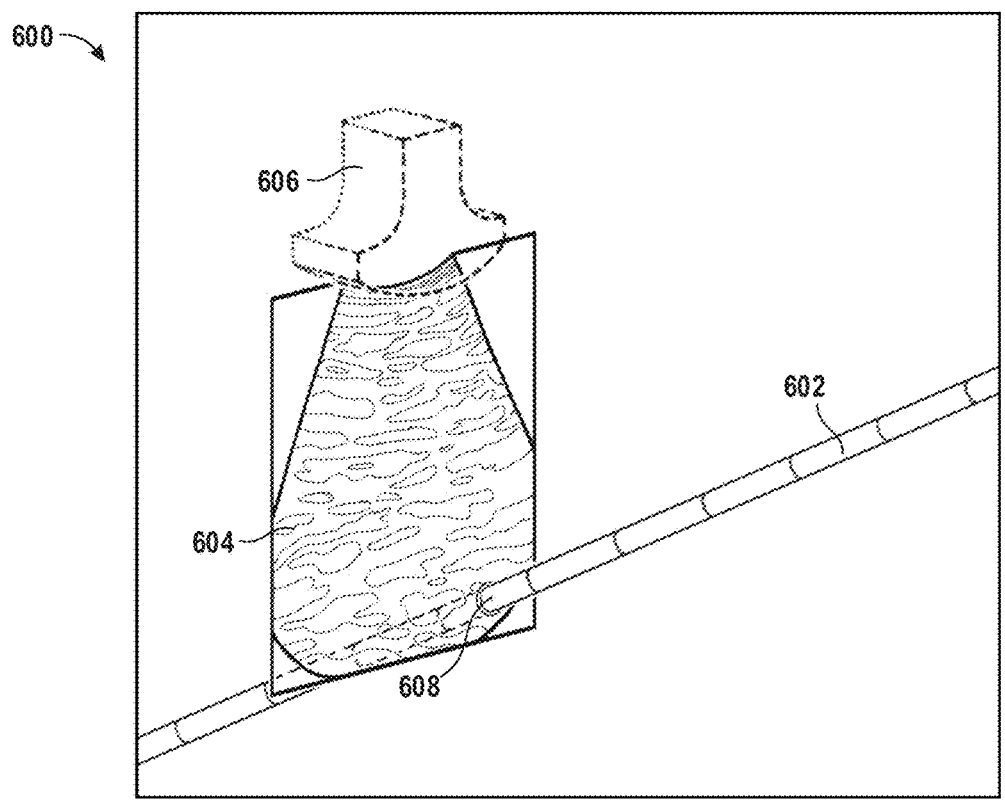
FIG. 6A illustrates an example virtual 3D scene.
Figure 6B:
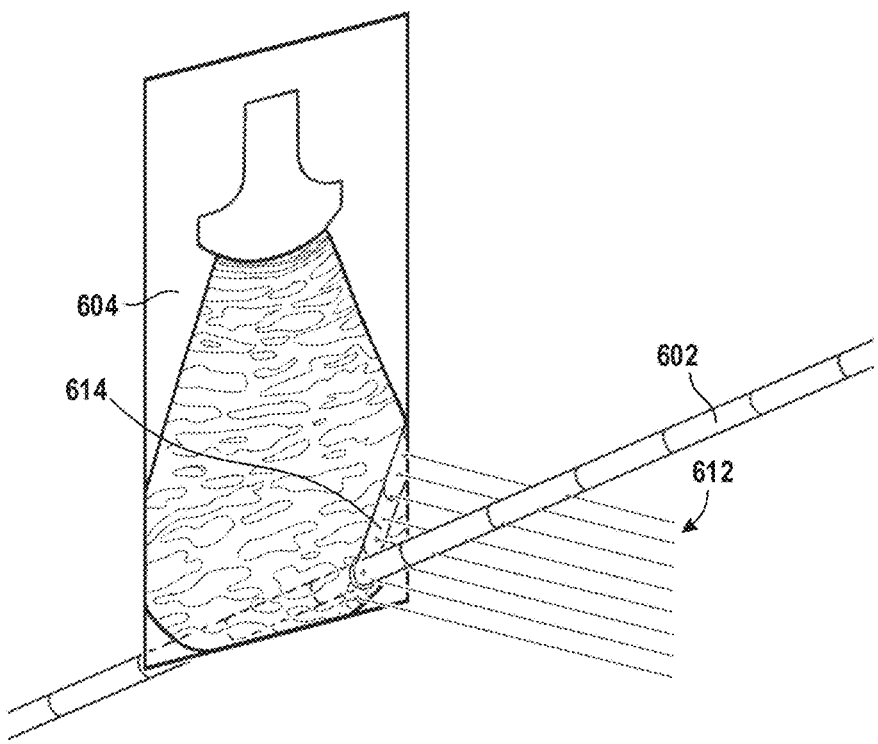
FIG. 6B illustrates a diagram that is useful for explaining a process for determining an example orthographic projection of a display object onto a 2D plane.
Figure 6C:
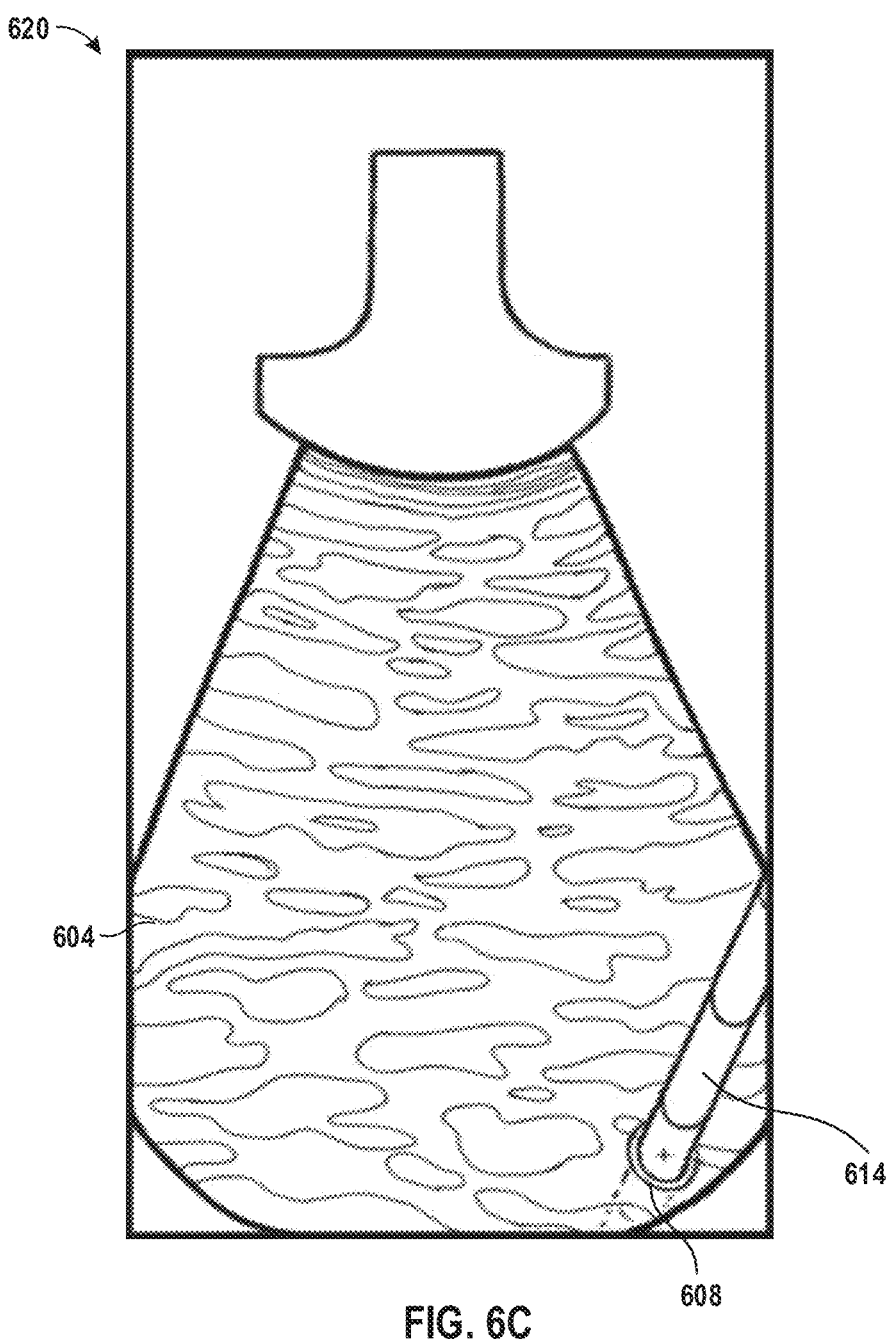
FIG. 6C illustrates an example 2D scene that includes a medical image and an example orthographic projection of a display object onto the medical image.

FIG. 6A-6C illustrates another example of orthographic projection of a display object onto a 2D plane. For example, FIG. 6A illustrates an example virtual 3D scene 600 that includes various image guidance data such as a virtual ultrasound transducer 606, a medical image 604 positioned at a transducing lens of the virtual ultrasound transducer 606, and a virtual medical needle 602 that traverses the medical image 604 at intersection point 608. The virtual medical needle 602 can be an embodiment of the first medical device 140, the virtual ultrasound transducer 606 can be an embodiment of the second medical device 145, and the medical image 604 can be an embodiment of the medical image 104 of FIGS. 1A-2.

FIG. 6B illustrates a diagram that is useful for explaining a process for determining a projection of the virtual medical needle 602 onto the medical image 604 using orthographic projection techniques. The diagram includes a plurality of projecting lines 612 that are orthogonal to a 2D plane of the medical image 604 and that intersect or meet both the virtual medical needle 602 and the medical image 604. In some cases, the projection of the virtual medical needle 602 can be identified or formed based at least in part on the intersections of the projecting lines 612 with the medical image 604. For example, the projection of the virtual medical needle 602 can be identified or formed by aggregating some or all of the intersections. An example orthographic projection 614 is illustrated on the medical image 604.

FIG. 6C illustrates an example 2D scene 620 that includes the medical image 604 and an orthographic projection 614 of the virtual medical needle 602 onto the medical image 604. As shown, the result of the orthogonal projection is a flat geometric structure that can be directly mapped onto a display, such as display 170 of FIG. 1A or display 470 of FIG. 4A.

As illustrated from a comparison of FIG. 6A and FIG. 6C, the orthographic projection 614 of the virtual medical needle 602 does not look identical to the virtual medical needle 602. That is also evidenced in the projection geometry illustrated in FIG. 6B, which includes both the virtual medical needle 602 and the orthographic projection 614. However, despite the difference in appearance, the orthographic projection 614 intuitively provides a viewer with information regarding the pose of the virtual medical needle 602. For example, from the 2D scene 620, it can be seen that the needle (e.g., the orthographic projection 614) traverses the medical image 604 at intersection point 608. Furthermore, based at least in part on the 2D scene 620, a viewer can intuitively tell that the needle (e.g., the orthographic projection 614) traverses the medical image 604 at a downward angle.

Single-Point Projection

In some embodiments, a 2D scene can be produced or determined using single-point projection techniques. For example, based at least in part on projecting lines extending from a point-of-projection location (sometimes referred to as center-of-projection) to particular image guidance data in a 3D virtual space, the single-point projections of the particular image guidance data can be determined. As described herein, a 2D scene generated based at least in part on single-point projection techniques can enable a viewer of the 2D scene to intuitively understand spatial relationships of a 3D virtual space, despite the 2D scene including a 2D image. For example, in some cases, through single-point projection, image guidance data that is more distant from the selected point-of-projection location can appear smaller in the 2D scene than image guidance data that is nearer to the point-of-projection location.

Figure 7A:
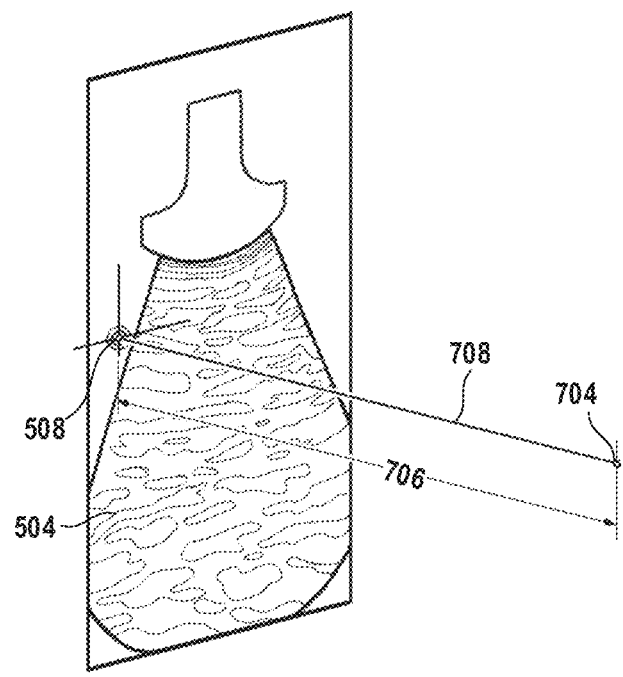
FIGS. 7A and 7B illustrate diagrams that are useful for explaining a process for determining an example single-point projection of a display object onto a 2D plane.
Figure 7B:
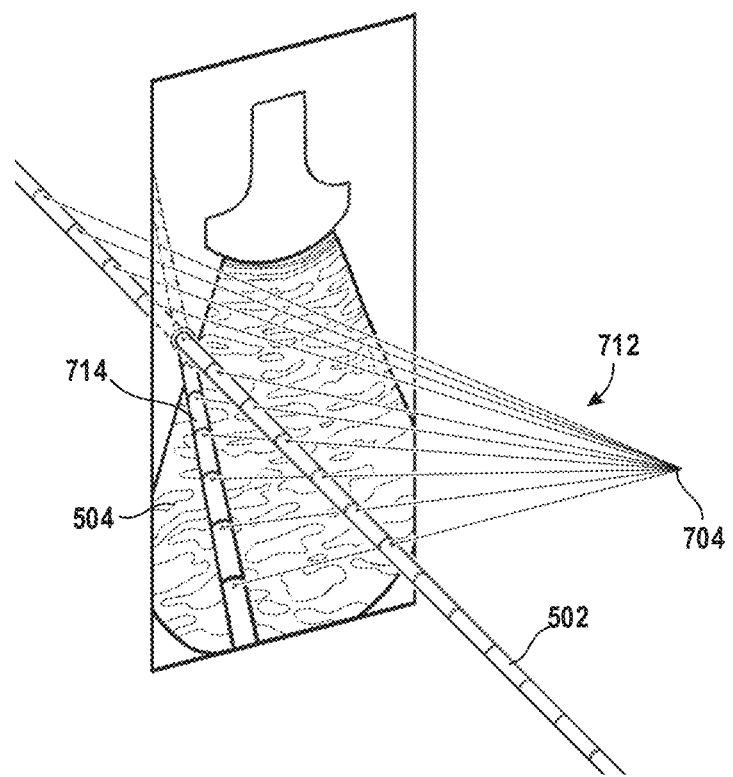

FIGS. 7A and 7B correspond to the 3D scene 500 of FIG. 5A and illustrate diagrams that are useful for explaining a process for determining a projection of the virtual medical needle 502 onto the medical image 504 using single-point projection techniques. In some embodiments, a single-point projection of the virtual medical needle 502 is based at least in part on a point-of-projection location. For example, the point-of-projection location can correspond to a projection reference point for determining the single-point projection of the virtual medical needle 502 onto the medical image 504.

FIG. 7A illustrates an example process for determining the point-of-projection location 704. For example, in some cases, to determine the point-of-projection location 704, the system determines an intersection associated with virtual medical needle 502 and the medical image 504. In this example, the intersection associated with the virtual medical needle 502 and a 2D plane of the medical image 504 includes intersection point 508, which denotes the intersection between the virtual medical needle 502 and the medical image 504 (as seen in FIG. 5A). However, in some cases, such as when the virtual medical needle 502 and the medical image 504 do not intersect, the intersection can include an intersection of a longitudinal axis of the virtual medical needle 502 with the medical image 504 or with the 2D plane of the medical image 504.

As further illustrated in FIG. 7A, a ray 708 is identified that is normal to the medical image 504 and that passes through the previously determined intersection 508, and a point along the ray 708 is selected. The selected point along the identified ray 708 is referred to as the point-of-projection location 704. The point-of-projection location 704 can be some distance 706 in front of or behind the medical image 504. In some cases, the distance 706 can be selected to correspond to an expected distance of a viewer's eye from a display when the viewer is looking at the display. In some cases, this can result in a natural-looking 2D scene that exhibits an amount of perspective distortion that matches an angle of the viewing frustum under which the viewer views the 2D scene. In some cases, the point-of-projection location 704 can be moved closer or further away from the medical image 504 as the angle between the virtual medical needle 502 and medical image 504 decreases (e.g., the virtual medical needle 502 becomes closer to being parallel to a plane of the medical image 504) or increases (e.g., the virtual medical needle 502 becomes closer to being orthogonal to the plane of the medical image 504).

FIG. 7B illustrates a diagram that includes a plurality of projecting lines 712. As shown, each of the projecting lines 712 emanate from the point-of-projection location 704 and intersect, or meet, both the virtual medical needle 502 and the medical image 504. In some cases, the projection of the virtual medical needle 702 can be identified or formed based at least in part on at least some of the intersections of the projecting lines 712 with the medical image 504. For example, the projection of the virtual medical needle 702 can be identified or formed by aggregating some or all of the intersections. An example single-point projection 714 is illustrated on the medical image 504.

Figure 7C:
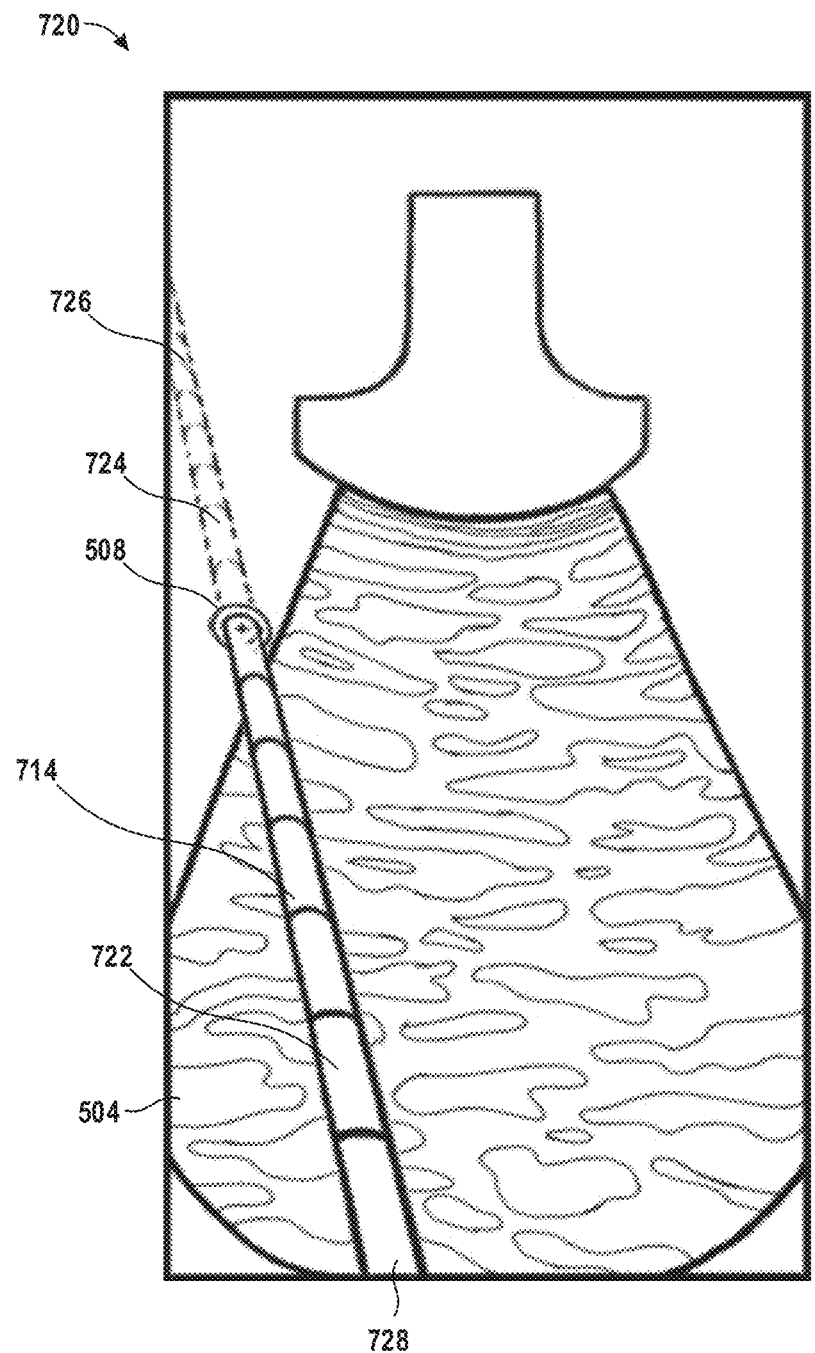
FIG. 7C illustrates an example 2D scene that includes a medical image and an example single-point projection of a display object onto the medical image.

FIG. 7C illustrates an example 2D scene 720 that includes the medical image 504 and a single-point projection 714 of the virtual medical needle 502 onto the medical image 504. As shown, the result of the single-point projection is a flat geometric structure that can be directly mapped onto a display, such as display 170 of FIG. 1A or display 470 of FIG. 4A.

As illustrated from a comparison of FIG. 5A and FIG. 7C, the single-point projection 714 of the virtual medical needle 502 does not look the same as the virtual medical needle 502. That is also evidenced in the projection geometry illustrated in FIG. 7B, which includes both the virtual medical needle 502 and the single-point projection 714. However, despite the difference in appearance, the single-point projection 714 intuitively provides a viewer with information regarding the pose of the virtual medical needle 502. For example, as illustrated in FIG. 5A, the virtual medical needle 502 is generally uniform in size along its longitudinal axis. In contrast, in FIG. 7C, the single-point projection 714 of the needle is not uniform in size. Rather, the single-point projection 714 appears smaller or narrower at a first portion 724 of the projection 714 than it appears at a second portion 722 of the projection 714. This difference in size provides a viewer with an intuitive understanding of the spatial relationship of the virtual medical needle 502 and/or the medical image 504. For example, a viewer can easily recognize that the smaller portion 724 is more distant from the point-of-projection location 704 and the larger portion 722 is nearer to the point-of-projection location 704. In some cases, the single-point projection 714 will appear with uniform thickness. For example, if the virtual medical needle 502 is coplanar or otherwise parallel with the medical image 504, then the single-point projection 714 can appear with uniform thickness.

In some cases, to further emphasize the spatial relationship between the medical image 504 and the virtual medical needle 502 shown by the 2D scene 720, the 2D scene can include image guidance cues such as, but not limited to, a trajectory of the virtual medical needle 502, or other visual elements. In some cases, the appearance of image guidance cues can be modulated by other parameters. For example, a needle shaft of the 2D projection 714 can be made to appear more blurry or more transparent with increased distance (in front or behind) from the medical image 504 or based at least in part on distance from the point-of-projection location 704. For example, in FIG. 7C, the portions 726 and 728 are distant from the intersection point 508 and therefore, in some cases, can appear more blurry or more transparent than other portions of the virtual medical needle 502 that are closer to the intersection point 508. In some cases, a level of blur or transparency can increase as the portions of the virtual medical needle 502 extend further away from the intersection point 508. In some cases, the virtual medical needle 502 can be at least partially transparent or illustrated as an outline, for example, to minimize an area of the medical image 504 that is obscured or covered by the virtual medical needle 502.

It will be understood that, in some embodiments, the point-of-projection location 704 is dynamic. For example, as described, the point-of-projection location 704 can be based at least in part on a relative emplacement of the virtual medical needle 502 and the medical image 504. Accordingly, in some cases, the point-of-projection location 704 can change as the relative emplacement of the virtual medical needle 502 and the medical image 504 changes. For example, the point-of-projection location 704 can change as the emplacement of the virtual medical needle 502 changes. As another example, the point-of-projection location 704 can change as the emplacement of the medical image 504 changes. As another example, the point-of-projection location can change as the angle of the virtual medical needle 502 changes with respect to the medical image 504.

Although FIGS. 7A-7C illustrates an example of single-point projection of the virtual medical needle 502 onto the medical image 504, it will be understood that similar techniques can be utilized to determine a single-point projection of any display object onto any viewplane. For example, in the illustrated examples of FIG. 7A-7C, the plane of the medical image 504 is selected as the viewplane. The viewplane can be understood as the 2D plane onto which the image guidance data from the 3D scene will be projected. Thus, in these examples, the resulting 2D scene 720 includes a single-point projection 714 of the virtual medical needle 502 onto the medical image 504. However, it will be understood that, in some embodiments, the viewplane can be any plane within the 3D scene 500 and is not limited to the plane corresponding to the medical image 504. In examples such as these, rather than determining an intersection associated with the medical image 504, an intersection is determined that is associated with the selected viewplane. Similarly, a ray may be identified that is normal to the selected viewplane, and the point-of-projection location is a point along that ray.

Figure 8A:
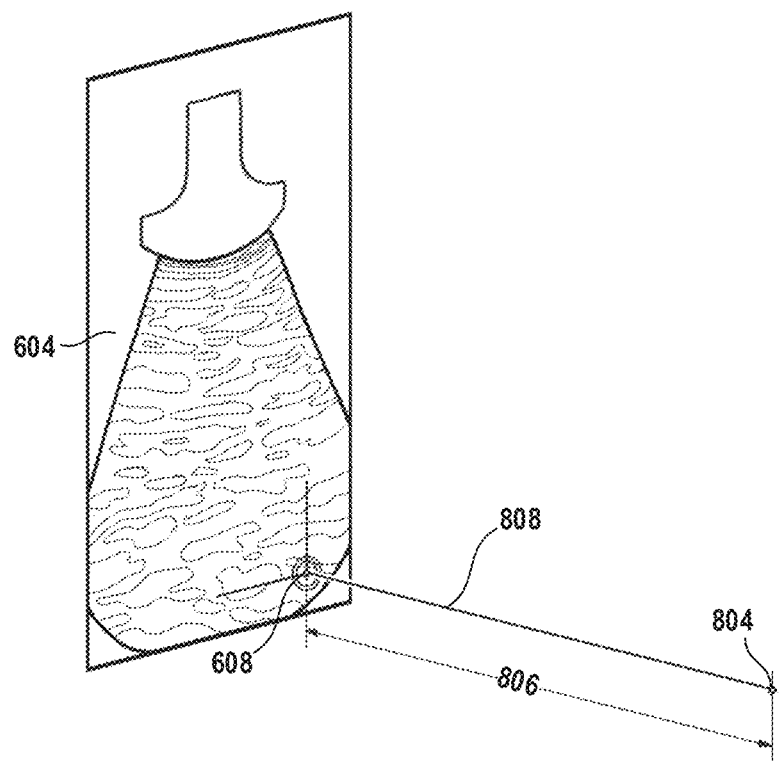
FIGS. 8A and 8B illustrate diagrams that are useful for explaining a process for determining an example single-point projection of a display object onto a 2D plane.
Figure 8B:
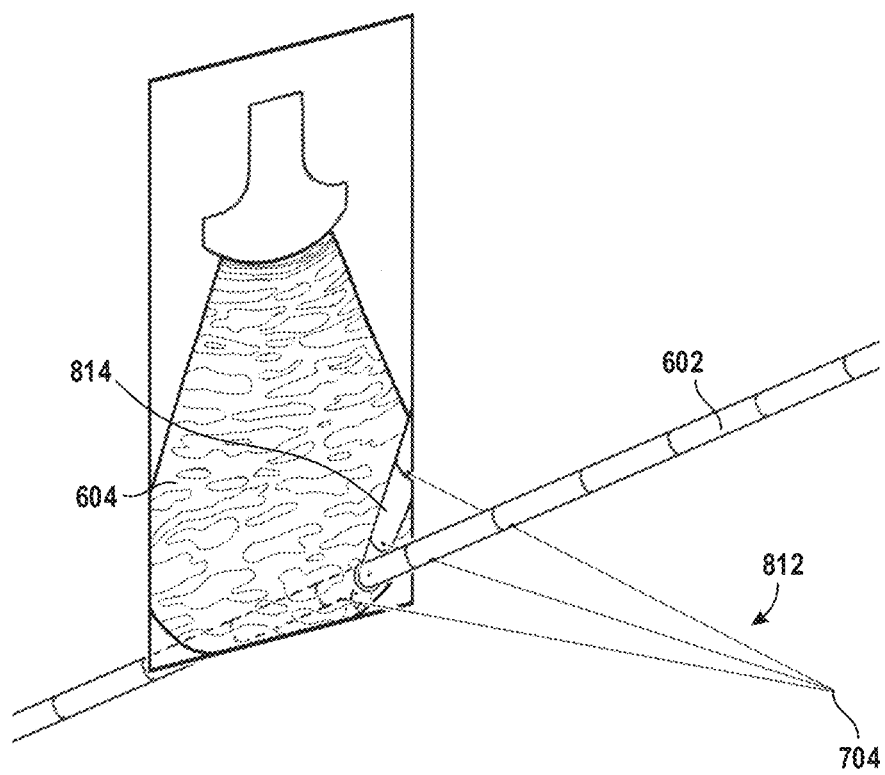
Figure 8C:
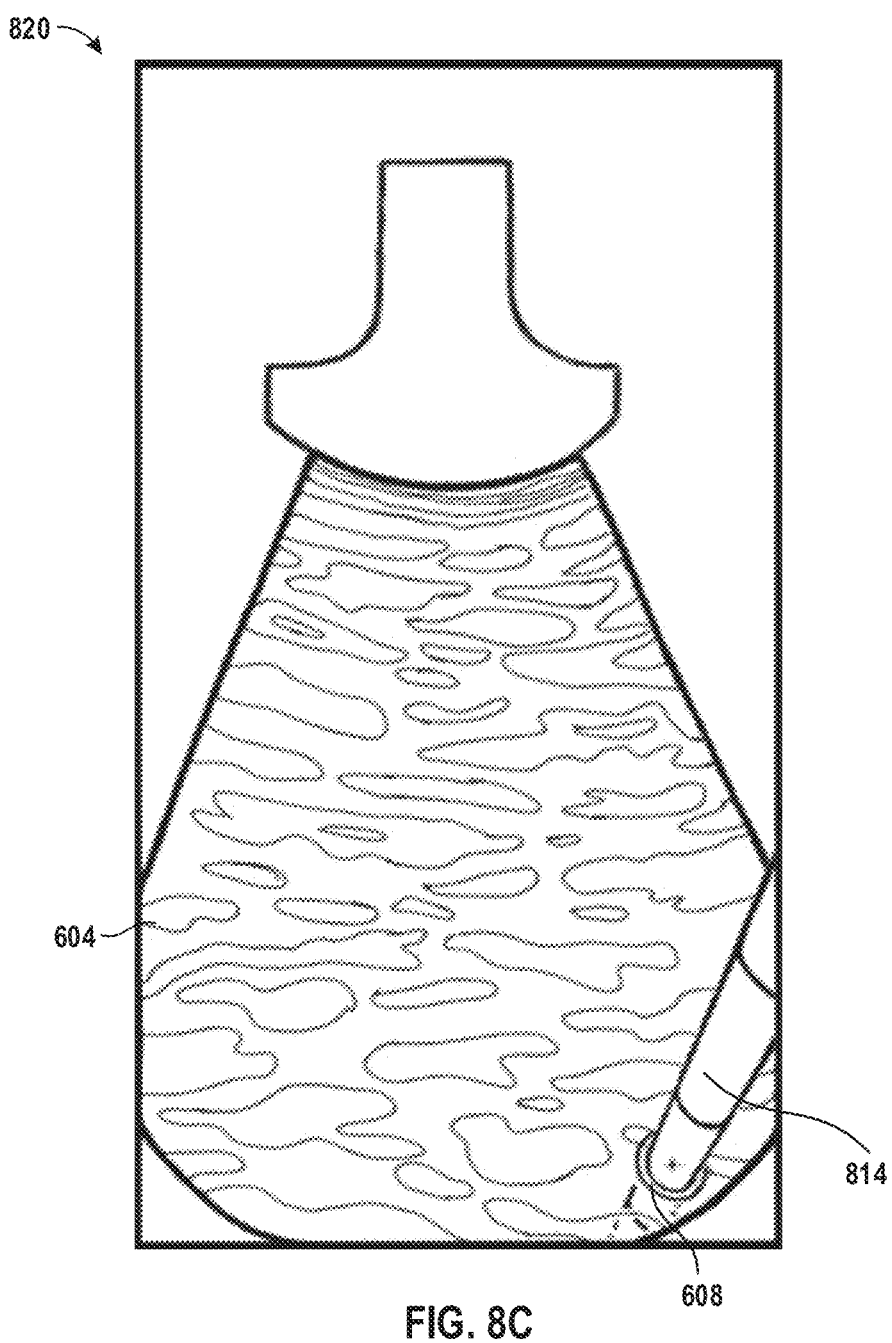
FIG. 8C illustrates an example 2D scene that includes a medical image and an example single-point projection of a display object onto the medical image.

FIGS. 8A-8C correspond to the 3D scene 600 of FIG. 6A and illustrate diagrams that are useful for explaining a process for determining a projection of the virtual medical needle 602 onto the medical image 604 using single-point projection techniques.

FIG. 8A illustrates an example process for determining the point-of-projection location 804. For example, in some cases, to determine the point-of-projection location 804, the system determines an intersection associated with virtual medical needle 602 and the medical image 604. In this example, the intersection associated with the virtual medical needle 602 and a 2D plane of the medical image 604 includes intersection point 608, which denotes the intersection of the virtual medical needle 602 with the medical image 604 or the 2D plane of the medical image 604. However, it will be understood that the intersection associated with the virtual medical needle 602 and the 2D plane of the medical image 604 can include various locations and this example should not be construed as limiting.

For example, in some embodiments, the intersection associated with the virtual medical needle 602 and the 2D plane of the medical image 604 can include an intersection of an axis of the virtual medical needle 602 with the medical image 604 or the 2D plane of the medical image 604. For instance, the intersection can include an intersection of the trajectory of the virtual medical needle 602 with the medical image 604 or 2D plane. As another example, the intersection can include an intersection of a ray that is normal to the medical image 604 (or 2D plane of the medical image 604), where the ray intersects with the medical image 604 (or 2D plane of the medical image 604) and some portion of the virtual medical needle 602. For example, the ray can intersect with portions of the virtual medical needle 602 that include, but are not limited to, a midpoint, an endpoint closest to the medical image 604, or an endpoint that is farthest from the medical image 604, etc.). Similarly, the intersection can correspond to a point on a plane that is normal to the medical image 604 and parallel to a longitudinal axis of the virtual medical needle 602 and/or intersects (and in some cases bisects) the virtual medical needle 602.

As another example, the intersection associated with the virtual medical needle 602 and the 2D plane of the medical image 604 can include an intersection of a ray that is not normal to the medical image 604, where the ray intersects with medical image 604 and the virtual medical needle 602. In some cases, the ray can intersect with a particular location on the medical image 604 (e.g., a center of the medical image 604, a top of the medical image 604, a bottom of the medical image 604, a left portion of the medical image 604, a right portion of the medical image 604, a corner of the medical image 604, etc.) and a particular location on the virtual medical needle 602 (e.g., midpoint of the medical image 604, an endpoint closest to the medical image 604 or an endpoint that is farthest from the medical image 604, etc.). In some cases, the intersection is simply any point on or offset from the virtual medical needle 602.

In this illustrated embodiment, a ray 808 is identified that is normal to the medical image 604 and that passes through the determined intersection 608. Furthermore, a point along the ray 808 is selected. The selected point along the identified ray 808 is referred to as the point-of-projection location 804. As described herein, the point-of-projection location 804 can be some distance 806 in front of or behind the medical image 604. In some instances, the distance 806 can be based at least in part on a size of a display that displays the 2D scene 820 (illustrated in FIG. 8C). For example, in some cases, the distance 806 is approximately equal to one display size (e.g., a length, width, or horizontal distance of the display). In some cases, the distance 806 is between one display size (e.g., a length, width, or horizontal distance of the display) and five display sizes (e.g., fives times a length, width, or horizontal distance of the display). In some cases, the distance 806 is equal to more than five display sizes (e.g., more than fives a length, width, or horizontal distance). As another example, the distance 608 can be less than 10 cm, between 10 and 50 cm, or more than 50 cm. In some cases, the distance 608 is equal to a length of the virtual medical needle 602, two lengths of the virtual medical needle 602, or more than two lengths of the virtual medical needle 602. It will be understood that the perspective effects of the single-point projection techniques are more exaggerated as the distance 806 increases. For example, a relatively small distance 806 can increase the visuals cues of the single-point projection, while a relatively larger distance 806 decreases the visuals cues of the single-point projection. For example, the longer the distance 806 is, the closer the single-point projection 814 will look to the orthographic projection 614 of FIG. 6C.

Moreover, as the intersection 608 changes due to movement of the physical medical device (and corresponding virtual medical device 602) or movement of the medical device that corresponds to the medical image 604 (and corresponding virtual medical device), the point-of-projection location 804 can change as well. In this way, the system can dynamically select the point-of-projection location 804 based on the emplacements (or relative emplacement) of two physical medical devices, two virtual medical devices, or the medical image 604 and the virtual medical device 602.

Although the illustrated example of FIG. 8A identifies a ray 808 that is normal to the medical image 604, in some cases the identified ray is not normal to the medical image 604. For example, in some cases, the identified ray 808 is a ray that passes through the intersection 608 and through a particular location on the virtual medical needle 602 (e.g., midpoint of the medical image 604, an endpoint closest to the medical image 604 or an endpoint that is farthest from the medical image 604, etc.). As another example and as described herein, the ray 808 can pass through a particular location of the medical image 604 (e.g., edge, upper/lower or left/right corner, etc.) and a particular location of the virtual medical device 602 (e.g., midpoint, endpoint closest to the medical image 604 or furthest from the medical image 604) or a particular location of the virtual medical device 606 and the virtual medical device 602, and may or may not pass through the intersection 608.

FIG. 8B illustrates a diagram that includes a plurality of projecting lines 812. As shown, each of the projecting lines 812 emanates from the point-of-projection location 804 and intersects or meet both the virtual medical needle 602 and the medical image 604. In some cases, the projection of the virtual medical needle 802 can be identified or formed based at least in part on at least some of the intersections of the projecting lines 812 with the medical image 604. For example, the projection of the virtual medical needle 802 can be identified or formed by aggregating some or all of the intersections. An example single-point projection 814 is illustrated on the medical image 804.

FIG. 8C illustrates an example 2D scene 820 that includes the medical image 604 and a single-point projection 814 of the virtual medical needle 602 onto the medical image 604. As shown, the result of the single-point projection is a flat geometric structure that can be directly mapped onto a display, such as display 170 of FIG. 1A or display 470 of FIG. 4A.

Advantageously, by rendering the 2D scene 820 in this way, the system can make it easier for a user to recognize that the needle (e.g., the single-point projection 814) traverses the medical image 604 at a downward angle. Furthermore, based at least in part on the difference in thickness of the single-point projection 814, the system can enable the viewer to intuitively understand that the narrower portion of the needle (e.g., the single-point projection 814) that is behind the medical image 604 is further away from the view than the wider portion of the needle that is in front of the medical image 604.

Orthographic Projection and Single-Point Projection

As described herein, a particular display object within a virtual 3D scene can be projected into a 2D scene using single-point projection techniques, and, similarly, a particular display object within a virtual 3D scene can be projected into a 2D scene using orthographic projection techniques. Furthermore, in some embodiments, a first display object within a virtual 3D scene can be projected into a 2D scene using single-point projection techniques and a second display object within the virtual 3D scene can be projected into the 2D scene using orthographic projection techniques. Similarly, in some embodiments, portions of a first display object within a virtual 3D scene can be projected into a 2D scene using single-point projection techniques, while other portions of the first display object can be projected into a 2D scene using orthographic projection techniques.

For example, returning to FIG. 5A, the virtual 3D scene 500 includes a virtual ultrasound transducer 506. As illustrated in FIG. 5A, at least some portions of the virtual ultrasound transducer 506 are perpendicular to the medical image 604. For example, because of the geometry of the virtual ultrasound transducer 506, at least portions of the top, bottom, and sides are perpendicular to the medical image 504. As a result of this geometry, and as illustrated by the 2D transducer 902 in FIG. 5C, an orthographic projection of the virtual ultrasound transducer 506 onto the medical image 504 will result in these edges all collapsing to a single outline. Because of this, in some cases, it may be beneficial to use single-point projection techniques to project at least a portion of these perpendicular portions of the virtual ultrasound transducer 506 onto the medical image 504. In some embodiments, as described herein, the single-point projection of the virtual ultrasound transducer 506 can be based at least in part on a point-of-projection location that is based at least in part on an intersection associated with the virtual ultrasound transducer 506 and the medical image 504. Alternatively, in some embodiments, the single-point projection of the virtual ultrasound transducer 506 can be based at least in part on a point-of-projection location that is based at least in part on an intersection associated with the medical image 504 and a display object other than the virtual ultrasound transducer 506. For example, in some cases, at least a portion of the virtual ultrasound transducer 506 can be projected based at least in part on the point-of-projection location 704 associated with the virtual medical needle 602, as described herein at least with respect to FIGS. 7A and 7B.

Figure 9A:
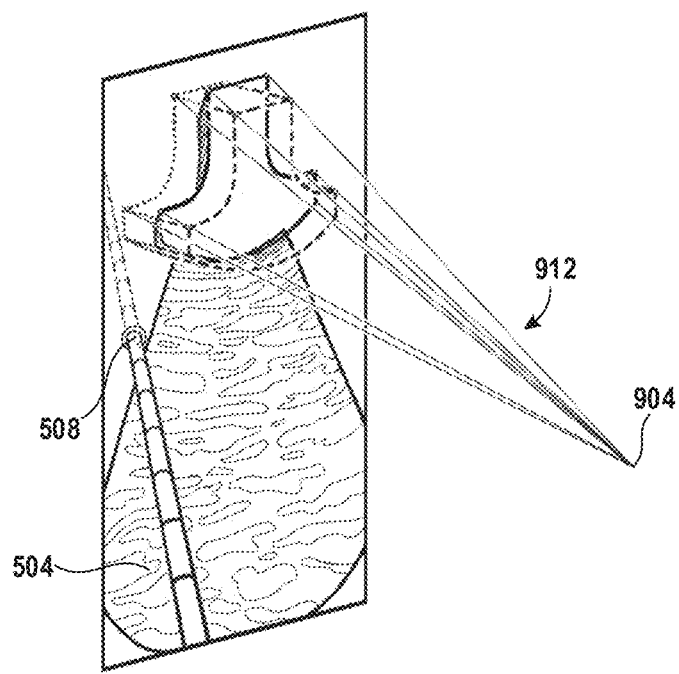
FIGS. 9A-9C illustrates diagrams that are useful for explaining a process for determining a single-point projection of at least a portion of a display object onto a medical image.
Figure 9B:
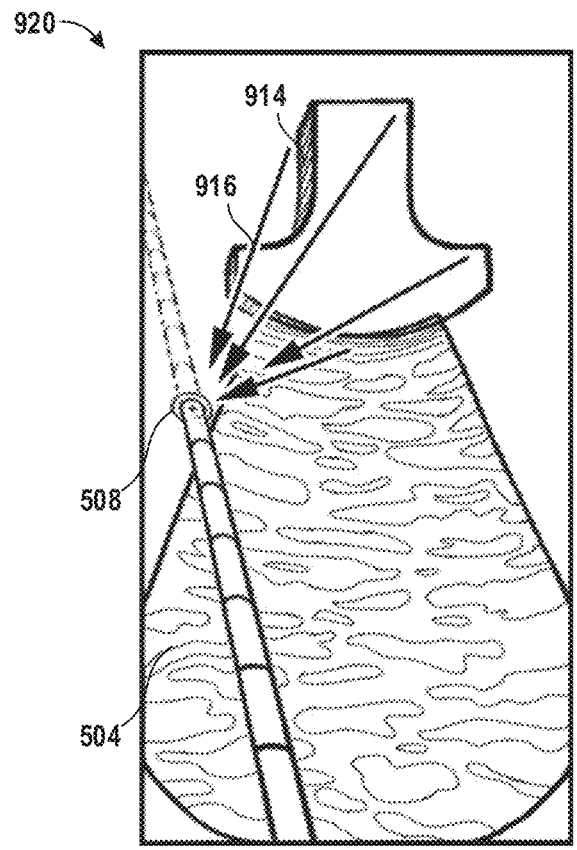
Figure 9C:
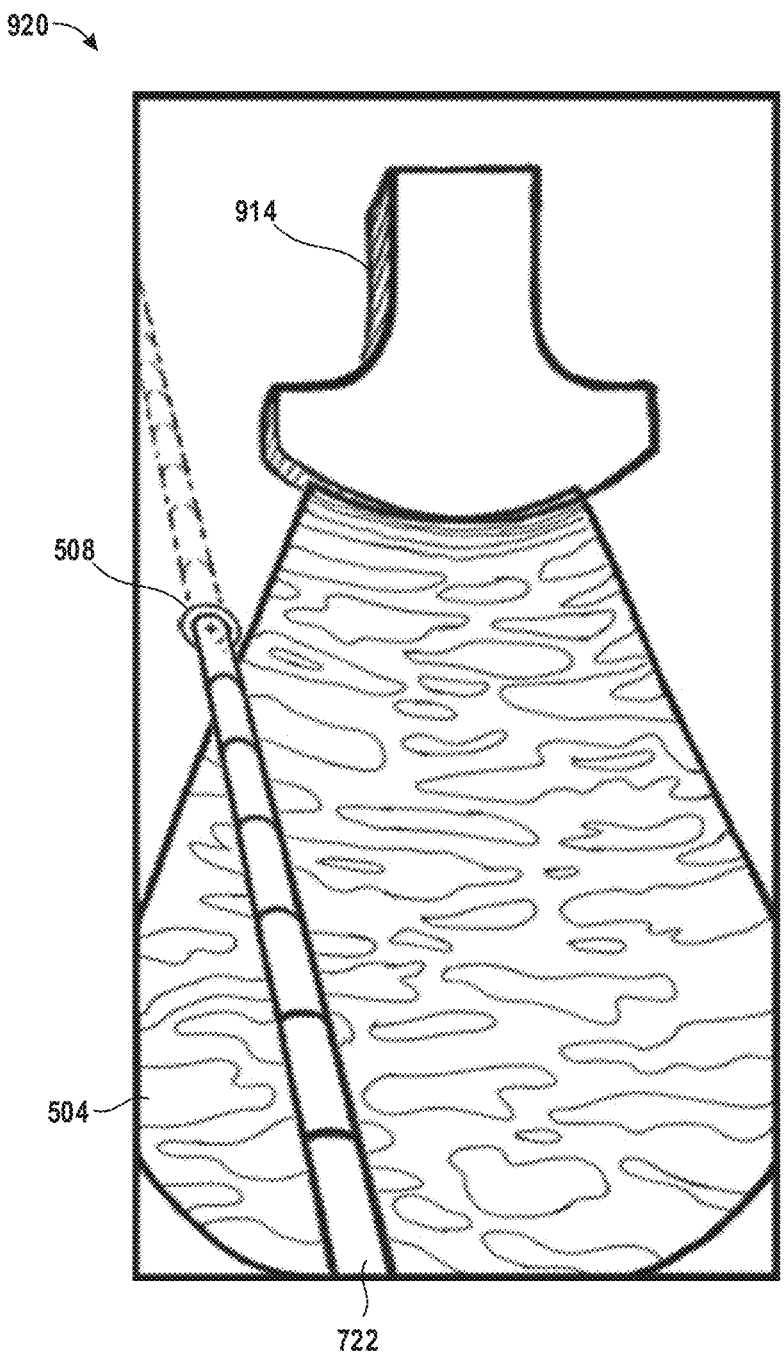

FIGS. 9A-9C correspond to the 3D scene 500 of FIG. 5A and illustrate diagrams that are useful for explaining a process for determining a projection of the virtual ultrasound transducer 506 onto the medical image 504 using single-point projection techniques. Similar to as described herein, in some embodiments, a single-point projection of the virtual ultrasound transducer 506 can be based at least in part on a point-of-projection location 904. In some cases, as illustrated, the point-of-projection location 904 (which corresponds to the virtual ultrasound transducer 506) can match the point-of-projection location 704 of FIG. 7B (which corresponds to the virtual medical needle 502). For example, in some cases, it can be advantageous that each of the display objects in a 3D scene, such as 3D scene 500, are single-point projected from the same point-of-projection location.

However, it will be understood that the point-of-projection location 904 corresponding to the virtual ultrasound transducer 506 can be different from the point-of-projection location 704 corresponding to the virtual medical needle 502. For example, in some cases, similar to as described herein for determining the point-of-projection location 704 for the virtual medical needle 502, the system can determine an intersection associated with virtual ultrasound transducer 506 and the medical image 504. For example, the intersection associated with the virtual ultrasound transducer 506 and a 2D plane of the medical image 504 can include an intersection of an axis of the virtual ultrasound transducer 506 with the medical image 504 or the 2D plane of the medical image 504, an intersection of the trajectory of the virtual ultrasound transducer 506 with the medical image 504 or 2D plane, or an intersection of a ray that is normal to the medical image 504 (or 2D plane of the medical image 504), where the ray intersects with the medical image 504 (or 2D plane of the medical image 504) and some portion of the virtual ultrasound transducer 506, For example, the ray can intersect with portions of the virtual ultrasound transducer 506 that include, but are not limited to, the portions that are perpendicular to the medical image 504, an furthest from the medical image 504, etc.

In some embodiments, as described herein and similar to the point-of-projection location 704, the system can determine an intersection (such as intersection 508 of FIG. 7A) associated with virtual medical needle 502 and the medical image 504. Furthermore, similar to ray 708 of FIG. 7A, a ray can be identified that is normal to the medical image 604 and that passes through the determined intersection 508. A point along the ray can be selected as the point-of-projection location 904. However, it will be understood that the distance of the point-of-projection location 904 from the front of or behind the medical image 504 can be different from the distance 706 of FIG. 7A. Accordingly, in some embodiments, the point-of-projection location 904 of FIG. 9A and the point-of-projection location 704 of FIG. 7A can be located at different positions along the same ray 708.

As shown, each of the projecting lines 912 emanate from the point-of-projection location 904 and intersect, or meet, both the virtual ultrasound transducer 506 and a 2D plane of the medical image 504. In some embodiments, a particular projecting line of the projecting lines 912 is utilized only if it intersects a portion of the virtual ultrasound transducer 506 that is perpendicular to the 2D plane of the medical image 504. In some embodiments, a particular projecting line of the projecting lines 912 is utilized only if it intersects a beginning-surface of the virtual ultrasound transducer 506. The beginning-surface can include only those surfaces, edges, or other portions of the virtual ultrasound transducer 506 that are facing the point-of-projection location 904 and that are not occluded from view (when viewing at the point-of-projection location 904) by the object's shape. In some embodiments, a particular projecting line of the projecting lines 912 is utilized only if it intersects a corner of the virtual ultrasound transducer 506. In some cases, the projection of the virtual ultrasound transducer 506 can be identified or formed based at least in part on at least some of the intersections of the projecting lines 912 with the 2D plane of the medical image 504. For example, the projection of virtual ultrasound transducer 506 can be identified or formed by aggregating some or all of the intersections.

FIGS. 9B and 9C illustrate an example 2D scene 920 that includes the medical image 504 and single-point projected surfaces 914 of the virtual ultrasound transducer 506 onto the medical image 504. As demonstrated by the arrows 916 in FIG. 9B, the single-point projected surfaces 914 and the textured edges included within subtly provide an additional cue for the intersection 508 by being angled towards it.

Figure 10A:
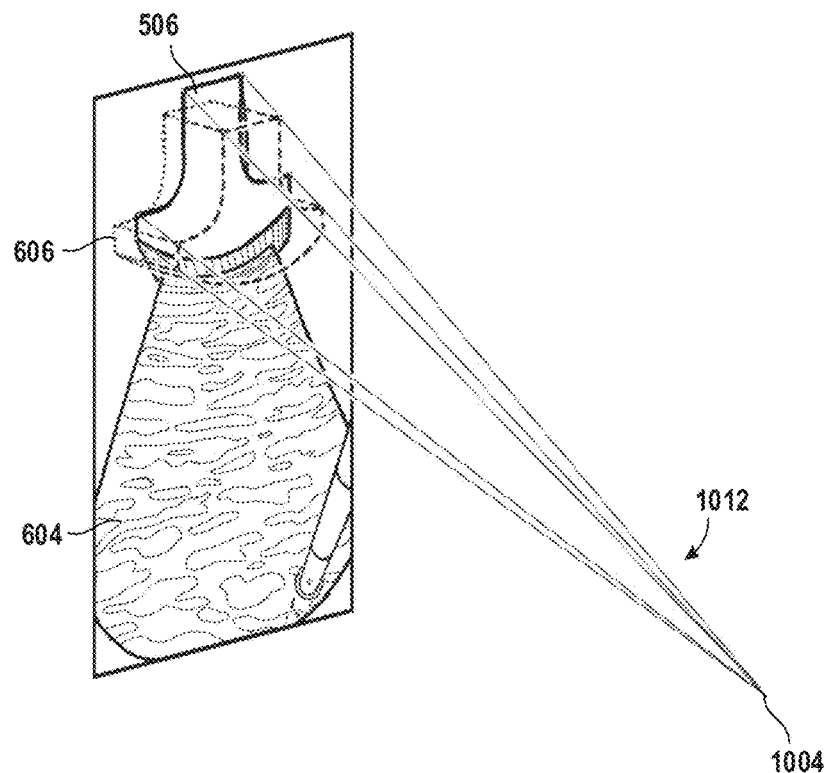
FIGS. 10A-10C illustrates diagrams that are useful for explaining a process for determining a single-point projection of at least a portion of a display object onto a medical image.
Figure 10B:
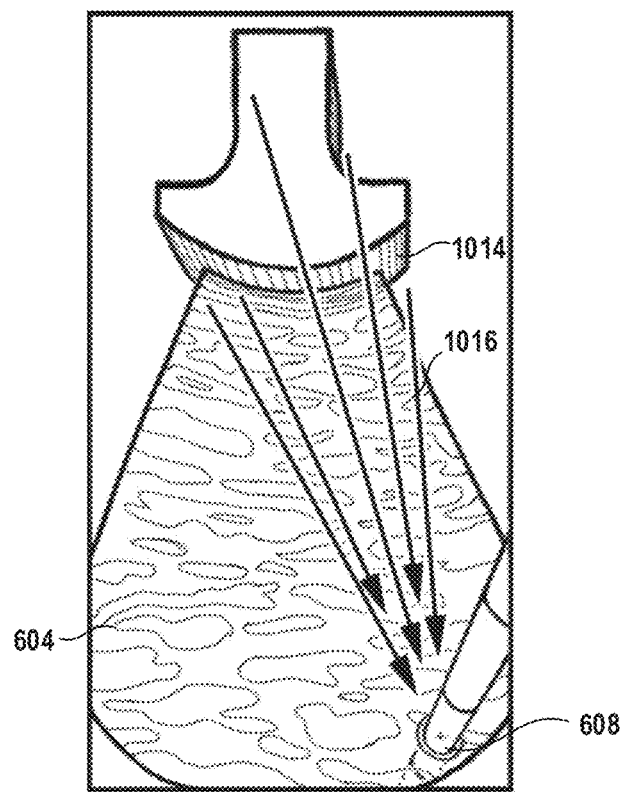
Figure 10C:
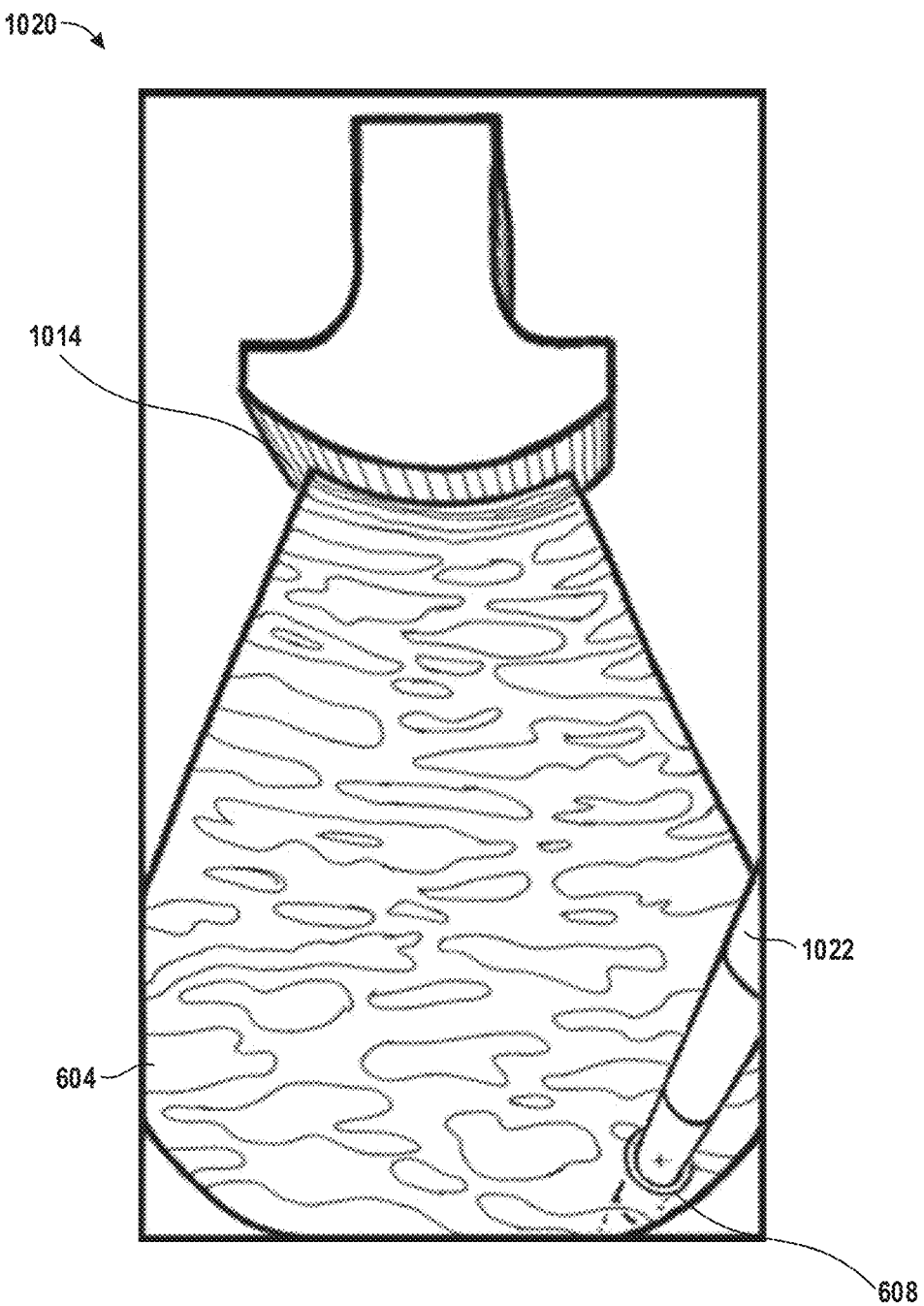

FIGS. 10A-10C correspond to the 3D scene 600 of FIG. 6A and illustrate diagrams that are useful for explaining a process for determining a projection of portions of the virtual ultrasound transducer 606 onto the medical image 604 using single-point projection techniques. As described herein, the single-point projection of the virtual ultrasound transducer can be based at least in part on the point-of-projection location 1004. For example, as shown, each of the projecting lines 1012 emanate from the point-of-projection location 1004 and intersect, or meet, both the virtual ultrasound transducer 606 and the 2D plane of the medical image 604.

In some embodiments, a particular projecting line of the projecting lines 1012 is utilized only if it intersects a portion of the virtual ultrasound transducer 606 that is perpendicular to the 2D plane of the medical image 604. In some embodiments, a particular projecting line of the projecting lines 1012 is utilized only if it intersects a beginning-surface of the virtual ultrasound transducer 606. In some cases, the projection of the virtual ultrasound transducer 606 can be identified or formed based at least in part on at least some of the intersections of the projecting lines 1012 with the 2D plane of the medical image 604. For example, the projection of virtual ultrasound transducer 506 can be identified or formed by aggregating some or all of the intersections.

FIGS. 10B and 10C illustrate an example 2D scene 1020 that includes the medical image 604 and single-point projected surfaces 1014 of the virtual ultrasound transducer 606 onto the medical image 604. As demonstrated by the arrows 1016 in FIG. 10B, the single-point projected surfaces 1014 and the textured edges included within subtly provide an additional cue for the intersection 608 by being angled towards it.

Example Environment

Figure 11:
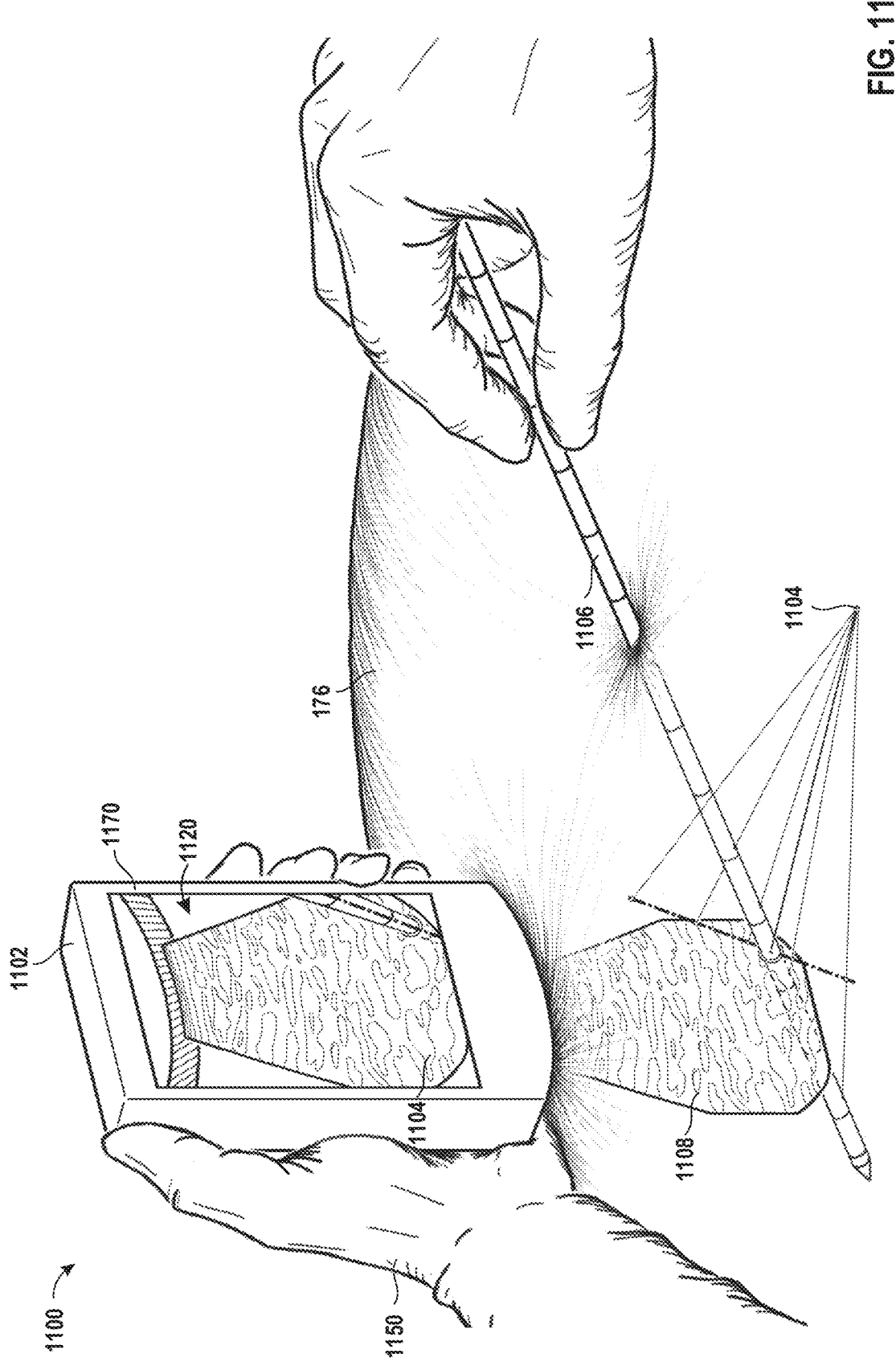
FIG. 11 illustrates an example environment for a medical device procedure.

FIG. 11 illustrates an example environment 1100 for a medical device procedure. The environment 1100 includes a medical device 1102 with a communicatively coupled display 1170. The environment 1100 further includes a medical provider 1150 manually navigating a medical needle 1106 though tissue of a patient 176 while viewing a 2D scene 1120 presented on the display 1170 for image guidance. The medical device 1102 can be an embodiment of the first medical device 140 or the second medical device 145 of FIGS. 1A-2; medical needle 1106 can be an embodiment of the first medical device 140 or the second medical device 145 of FIGS. 1A-2; the 2D scene 1120 can be an embodiment of the 2D scene 120, 520, 620, 720, 820, 920, or 1020 of FIG. 1A-2, 5, 6, 7, 8, 9, or 10, respectively; the medical image 1104 can be an embodiment of the medical image 104, 504, or 604 of FIG. 1A-2, 5, or 6; or the display 1170 can be an embodiment of the display 170 of FIGS. 1A-2.

In the illustrated environment 1100, the medical device 1102 is implemented as an ultrasound transducer. In some implementations, the medical device 1102 can be controlled by a processor (not shown) to image a 2D region of tissue 1108 of the patient 176. For example, a processor in communication with the medical device 1102 can cause the medical device 1102 to emit sounds waves into the 2D region of tissue 1108 and receive image data corresponding to echoes of the sound waves after the sound waves are emitted into the region of tissue 1108. A processor in communication with the medical device 1102 can process the image data to determine the medical image 1104.

The 2D scene 1120 can be an embodiment of any of the 2D scene 120, 520, 620, 720, 820, 920, or 1020 of FIG. 1A-2, 5, 6, 7, 8, 9, or 10, respectively. For example, the 2D scene 1120 can include the medical image 1104 and one or more single-point projection(s) of image guidance data.

As described herein, a viewing area of the display 1170 (which can be referred to as a viewing screen) can be aligned such that it is parallel to a 2D region of tissue 1108 that is imaged by the medical device 1102. As a result of this alignment, the pose of the display 1170 (and thus the 2D scene 1120, which can include medical image 1104) changes with the pose of the medical device 1102.

As described herein, the display 1170 can be communicatively coupled to the medical device 1102. For example, the display 1170 can be integrated into the medical device 1102, such as in a housing of the medical device 1102. As another example, the display 470 can be a coupled or attached to the medical device 1102.

Introducer Needle

As described herein, the disclosed systems and methods can facilitate image-guidance in medical procedures. In some embodiments, the medical procedures can include, but are not limited to, procedures relating to vascular access, venipuncture, central lines, intravenous therapy (IV), catheterization, or other related procedures.

Vascular access workflow can involve inserting and removing devices (e.g. a guidewire) down the central lumen of an introducer needle or catheter, etc. In some embodiments, a tracked device can be configured to go into the lumen of an introducer needle, catheter, or similar device, and attach to an introducer needle. Vascular access devices are generally designed to lock together via the standardized leak-free Luer taper system (commonly known as Luer-lock or Luer-slip connectors), or other standard mechanism for attaching devices together. In some embodiments, a tracked device can be made to conform to such locking standards such as to fit into common vascular access workflow. In some cases, using such standards can improve the likelihood that a tracked device can be consistently inserted into or attached to an introducer needle with a known relationship between the tracked device and the needle/needle tip.

An introducer needles can be used to create an access point in a vessel. As illustrated, an introducer needle can include a central lumen into which blood is drawn and/or through which guidewires, catheters or other devices are routed. In some cases, it can be important to position a tip of the introducer needle into a vessel without nicking the vessel wall, going through its back wall, causing other damage, or missing the vessel entirely. However, it is often challenging to accurately place an introducer needle into a vessel. This can be true even when using medical imaging to guide the introduction.

Systems and methods disclosed herein can be utilized to track an introducer needle and provide guidance visualization that can facilitate accurate needle placement into a vessel. As described herein, introducer needles or other medical devices can be tracked relative to another medical device or relative to a coordinate system.

In some embodiments, an introducer needle can be tracked via an attached tracked device that can be permanently or temporarily attached to or inserted into an introducer needle. FIGS. 12A-12D illustrate various embodiments of introducer needles 1210, 1220, 1230, and 1240 having a tracked device positioned at a location 1202 within the introducer needles 1210, 1220, 1230, and 1240.

If a tracked device is placed into a sheath, such as polyimide or similar material, or inside a strengthening sheath made of steel or other material, the tracked device can be routed into an introducer needle to track the needle's tip. Tracking the tip can be useful, for example in cases where the introducer needle is flexible. In some cases, a distal, central, proximal or other portion of the tracked device can be tracked. For example, if the needle is not flexible, or is sufficiently rigid, the tip location derived from a proximally located sensor can be used for vascular access.

In some cases, a tracked device can be secured onto a lock, such as the Luer lock. For example, the tracked device can be attached inside, outside, or be integral to the offset or angled area off of a main, straight channel. This can enable a stiff Luer lock introducer or longer needle to enter the central channel and seal tightly with a standard Luer lock (with a male version on one end and a female version on the other end of the tracker pod). The central channel (or additional attached channels) can be used to inject or extract fluids or other devices as desired.

In some embodiments, the tracked device can be removed from the introducer needle 1210, 1220, 1230, or 1240 once the introducer needle 1210, 1220, 1230, or 1240 has entered the target vessel. For tracked devices inserted into an introducer needle 1210, 1220, 1230, or 1240, if the introducer needle lumen is wide enough, sufficient space can be left to allow a blood return (sometimes referred to as flashback) through the introducer needle lumen. Alternatively, a tracked device can be designed such that it can be placed around a hollow tube with a lumen, such that a blood return can flow into the tube without being blocked by the tracked device. A tracked device can also be mounted into a tube-like device which has a recess, flat, or other such deformity to allow blood to flow past the sensor tube; this deformed tube can be similar in shape to a half-circle to keep it toward one side of the needle to provide better flow.

Figure 12B:
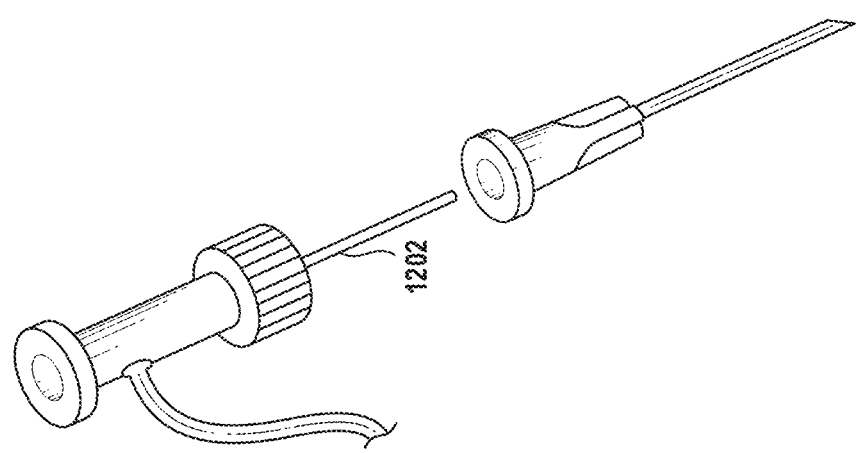
FIGS. 12A-12D illustrate various embodiments of example introducer needles.
Figure 12A:
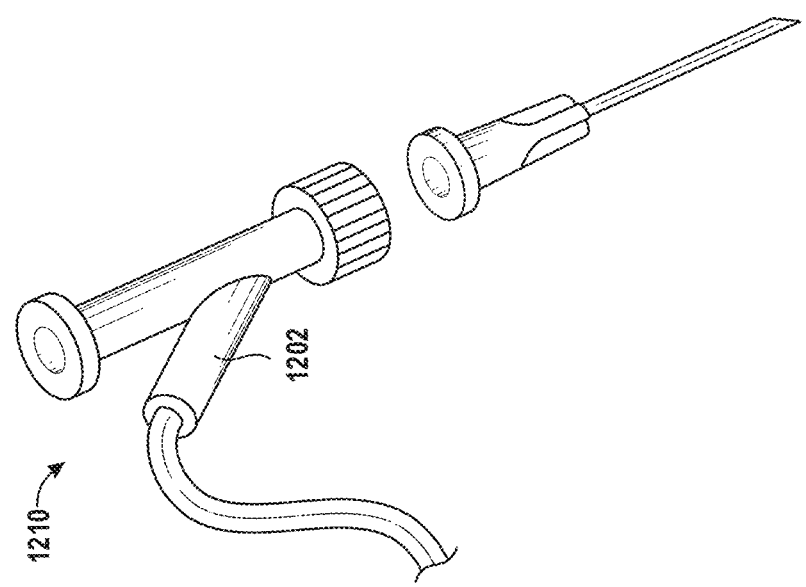
Figure 12C:
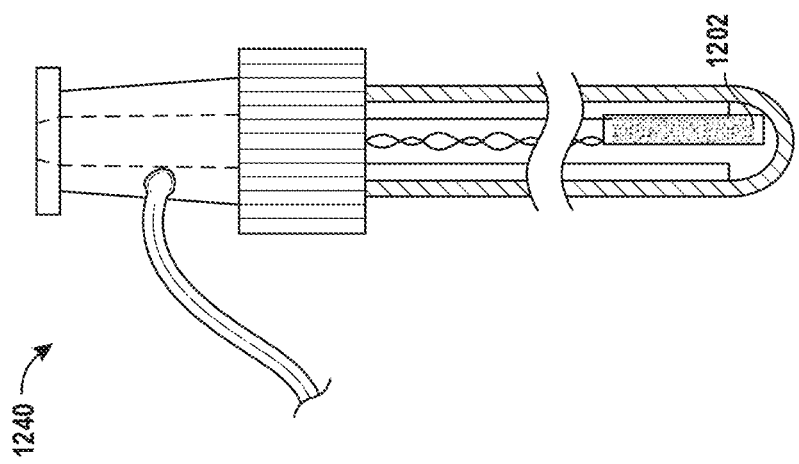
Figure 12D:
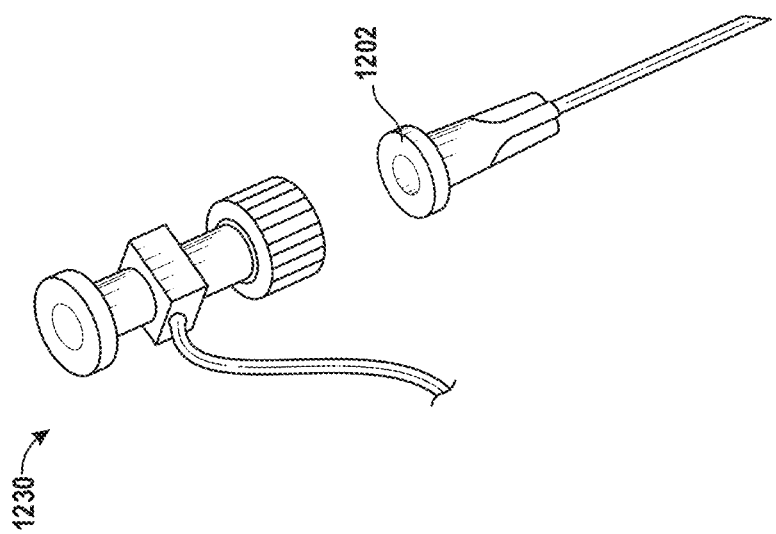
Figure 12F:
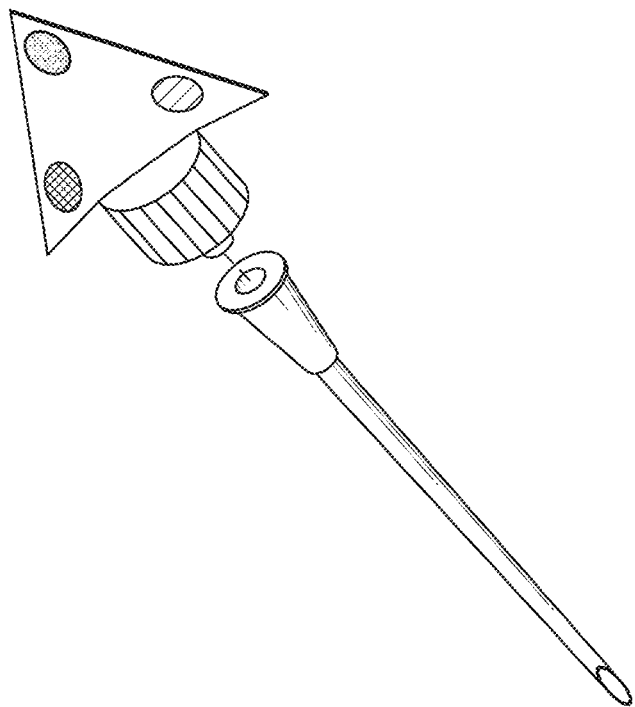
FIGS. 12E-12F illustrate embodiments of example optical markers.
Figure 12E:
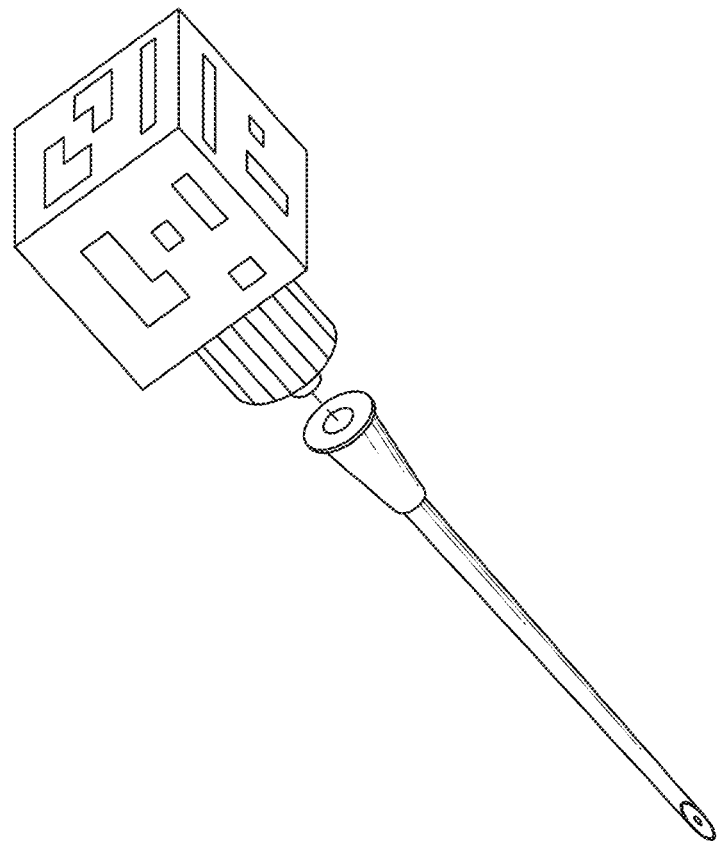

FIGS. 12E and 12F illustrate various embodiments of optical markers attached to Luer lock mechanisms, to attach to and track needles. As described herein, the system can include an optical tracking system using fiducials. One or more visually-detectable fiducials can be coupled to or otherwise associated with one or more medical devices, such as the devices in FIGS. 12E and 12F.

Figure 13A:
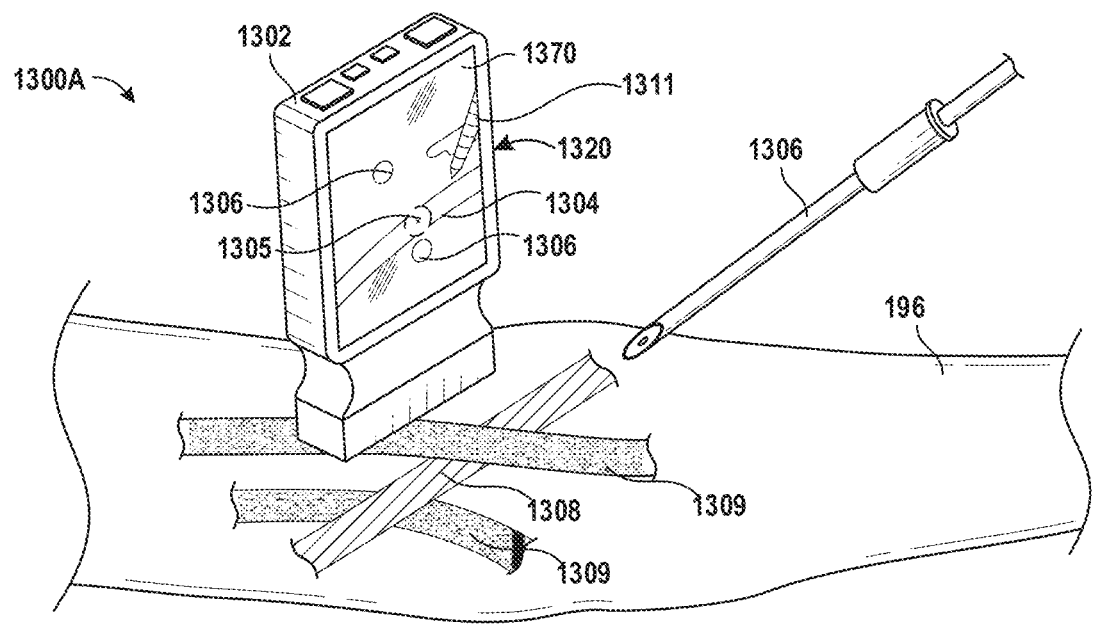
FIGS. 13A-13C illustrate example environments for a medical device procedure.
Figure 13B:
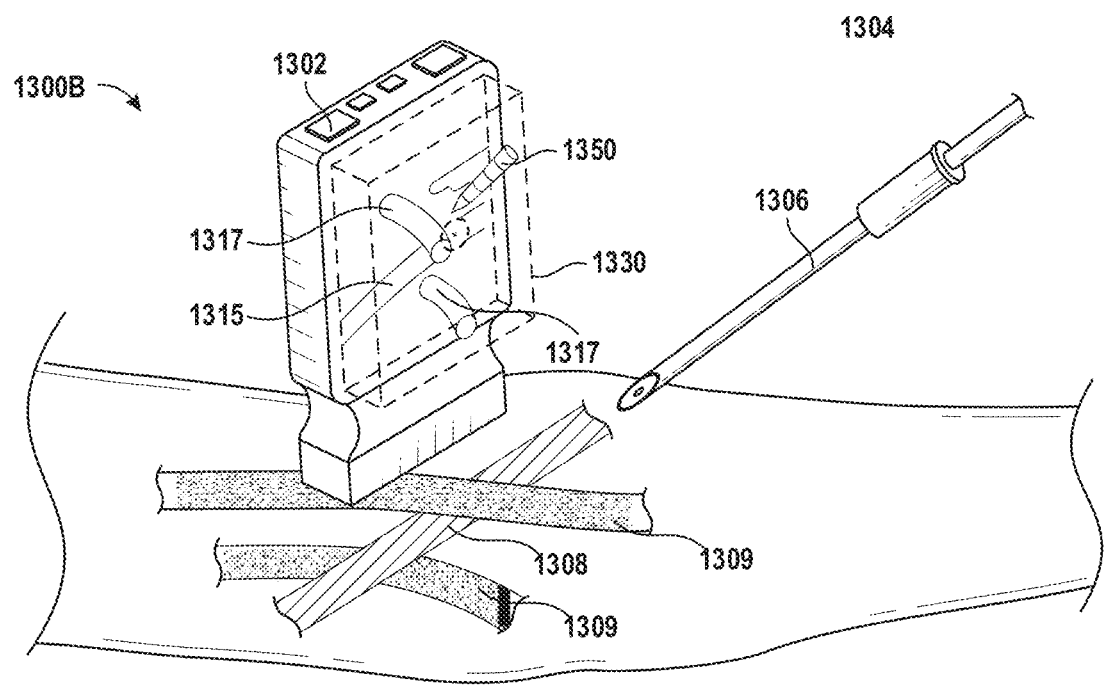

FIGS. 13A-13B illustrate example environments 1300A, 1330B for a medical device procedure. The environment 1300 can include a medical device 1302 with a communicatively coupled display 1370. The environments 1300A, 1330B further include a medical needle 1306 being navigated through tissue of a patient 196. The medical device 1302 can be an embodiment of the first medical device 140 or the second medical device 145 of FIGS. 1A-2; the medical needle 1306 can be an embodiment of the first medical device 140 or the second medical device 145 of FIGS. 1A-2; the 2D scene 1320 can be an embodiment of the 2D scene 120, 520, 620, 720, 820, 920, or 1020 of FIG. 1A-2, 5, 6, 7, 8, 9, or 10, respectively; the medical image 1304 can be an embodiment of the medical image 104 of FIGS. 1A-2; and/or the display 1370 can be an embodiment of the display 170 of FIGS. 1A-2.

As illustrated in FIG. 13A, in some cases, to provide information about the location of a target vessel 1308 location, a 2D scene 1320 can be displayed. In some cases, within the 2D scene 1320, the clinician can see at least some of the geometry 1304 of the target vessel 1308, and, in some cases, the geometry 1306 of other vessels 1309 or structures that may obstruct the planned needle insertion trajectory. Needle trajectory, needle visualization 1311, or intersection indicator 1305 can be shown as the needle traverses the tissue, such that the clinician can see which structures would be affected, and assess how to avoid them.

As illustrated in FIG. 13B, in some cases, to provide information about the location of a target vessel 1308, a volumetric representation 1330 of the target vessel or surrounding tissue can be generated by scanning for the vessel using either a 3D ultrasound probe, or a tracked 2D ultrasound probe that a clinician moves to scan a volume of tissue containing the target vessel. This tracked ultrasound probe can deliver positions and orientations provided by the tracking system for each captured ultrasound image frame, thus enabling construction of the volumetric representation 1330, which can be at least partially displayed on the display 1370, for example as a 2D scene 1320 of FIG. 13A. In some cases, within the volume 1330, the clinician can see the geometry 1315 of the target vessel 1308, and, in some cases, the geometry 1317 of other vessels 1309 or structures that may obstruct the planned needle insertion trajectory. Needle trajectory or needle visualization 1350 can be shown as the needle traverses the tissue, such that the clinician can see which structures would be affected, and assess how to avoid them.

In some embodiments, the patient's skin surface and shape can be captured. For example, skin surface and shape can be captured from ultrasound imagery as the clinician scans over the patient's skin. As another example, skin surface and shape can be captured using cameras and/or depth sensors (using, for example, structured light, time-of-flight lasers, infrared dot patterns, single- or multi-baseline stereo imagery, etc.), such as, but not limited to, the Intel RealSense, Microsoft Kinect, Lightform, Google Tango and/or ARCore, a mobile device such as an Apple iPhone, and/or ARKit, or other devices. In some cases, the skin surface and shape can be visualized around the internal vascular structure (and other structures) (for example, transparently, as a wireframe, or as a point cloud) to provide the clinician with further context about the target vessel's location, such as its depth below the skin surface.

Segmenting vessels from the surrounding structures and/or disambiguating veins from arteries and other structures can help guide a clinician to accurately insert a needle into a vessel. Vessels can be identified using a variety of automatic, semi-automatic, or manual methods (e.g. segmentation via tracing, image analysis, or machine learning).

In some embodiments, after or while a vessel is identified (e.g., through Doppler imaging, ultrasound contrast, manual selection on an ultrasound image, machine learning, near-infrared light, etc.), a 3D or 2D visualization on a display can show which part of the ultrasound scan is the vessel, or use existing standard Doppler colorization to disambiguate veins and arteries, for example. In a volumetric ultrasound scan visualization, such as visualization 1330, vessel flow direction can be indicated in many ways, including but not limited to color, static arrows, moving arrows, animation of fluid flow, or text labels.

In some cases, the ultrasound scan volume, along with needle trajectory, scan intersection, patient skin surface, or other visualizations, can be displayed in a tracked head-mounted display (HMD), which a clinician can wear. Because the HMD is tracked, the clinician can move their head to view the ultrasound scan, scan volume, visualizations, etc. along arbitrary directions and from their own (dynamic) point of view. The visualizations, etc. can be shown either registered to the ultrasound probe, or offset elsewhere to improve image contrast or clinician comfort.

In some embodiments, a volume can be constructed from ultrasound images (or images of another modality) and can include segmented vessels. Representations of the vessels can be mapped onto the skin surface to present the clinician with obstruction-free entry points for the introducer needle to reach the target vessel, given the introducer needle's pose (e.g., an angle relative to the skin). In each of FIGS. 13A and 13B, an artery partially occludes a vein from certain directions.

The visualizations 3D can be displayed in a variety of ways, including but not limited to being shown on an ultrasound scanner display, an external TV or monitor, on a display mounted on the ultrasound probe, projected onto a screen or onto the patient's skin, or in virtual reality (VR) or augmented reality (AR) head-mounted displays (HMDs) or smart-glasses. Example VR HMDs include, but are not limited to, the HTC Vive and Oculus Rift. Example AR HMDs include, but are not limited to, the Microsoft Hololens, ODG R-7, and Magic Leap One. The ultrasound image and associated visualizations can be shown in 2D (monoscopically) or in 3D (stereoscopically).

In some embodiments, as illustrated in FIG. 13B, the visualizations 1330 can be shown on a combination of a display screen and via a HMD or stereoscopic display. For example, in some cases, the display screen can show certain portions of the visualizations 1330 in high contrast, while a HMD or stereoscopic display can show certain portions of the visualizations 1330 in lower contrast.

Figure 13C:
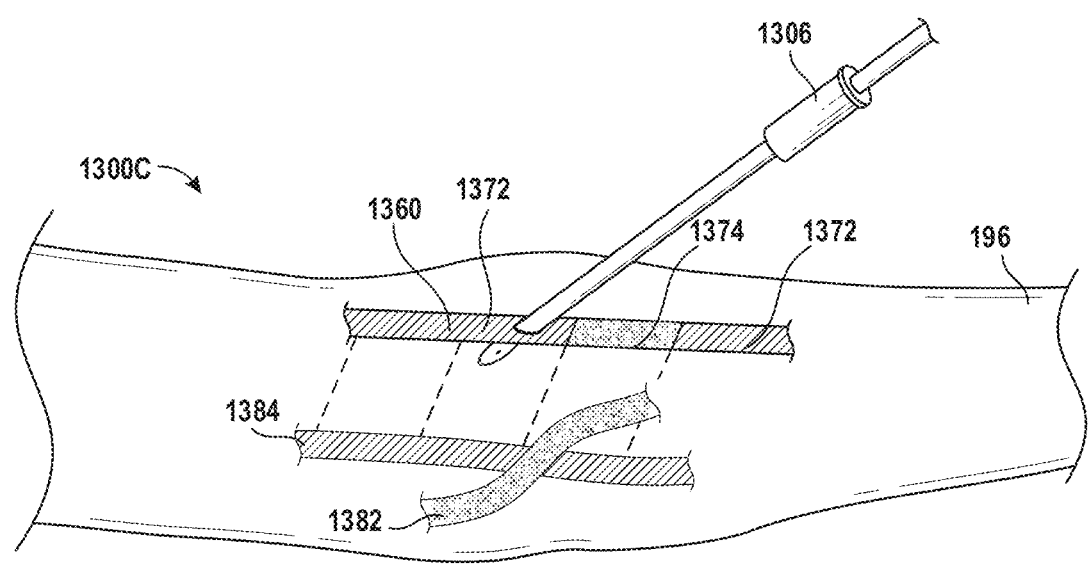

FIG. 13C illustrates an example environment 1300C for a medical device procedure. In the illustrated example, the representations 1360 of the vessels 1362 are mapped and displayed onto the skin surface of the patient 196. As described herein, in some cases, a volume can be constructed from ultrasound images (or images of another modality) and can include segmented vessels. The representations 1360 of the vessels can be mapped onto the skin surface to present the clinician with obstruction-free entry points 1372 for the introducer needle to reach the target vessel, given the introducer needle's pose (e.g., an angle relative to the skin). Similarly, the representations 1360 can present point of obstruction 1374, which the physician should avoid. For example, in FIG. 13C, an artery 1382 partially occludes a vein 1384 from certain directions. Given the needle angle, the point of obstruction 1374 and/or the obstruction-free entry points 1372 can be mapped or projected onto the skin surface to inform the clinician from which regions of the skin they can enter the target vessel at that needle angle.

In some embodiments, the representations 1360 on the skin can be based at least in part on a pose of the needle. Accordingly, based at a change in pose of the needle relative to the skin, the representations 1360 can be updated such that the obstruction-free entry points 1374 would reflect the new angle of approach. The representations 1360 can be projected onto the skin from a projector, such as a projector mounted on the ultrasound probe, somewhere in the room, on a free-standing structure, an articulating arm that points the projector towards the patient's skin, on the clinician's head, or in any other location.

In some embodiments, representations 1360 can be displayed in a variety of ways, including but not limited to being shown on an ultrasound scanner display, an external TV or monitor, on a display mounted on the ultrasound probe, projected onto a screen or onto the patient's skin, or in virtual reality (VR) or augmented reality (AR) head-mounted displays (HMDs) or smart-glasses. Example VR HMDs include, but are not limited to, the HTC Vive and Oculus Rift. Example AR HMDs include, but are not limited to, the Microsoft Hololens, ODG R-7, and Magic Leap One. The ultrasound image and associated visualizations can be shown in 2D (monoscopically) or in 3D (stereoscopically).

Flow Diagrams

Figure 14:
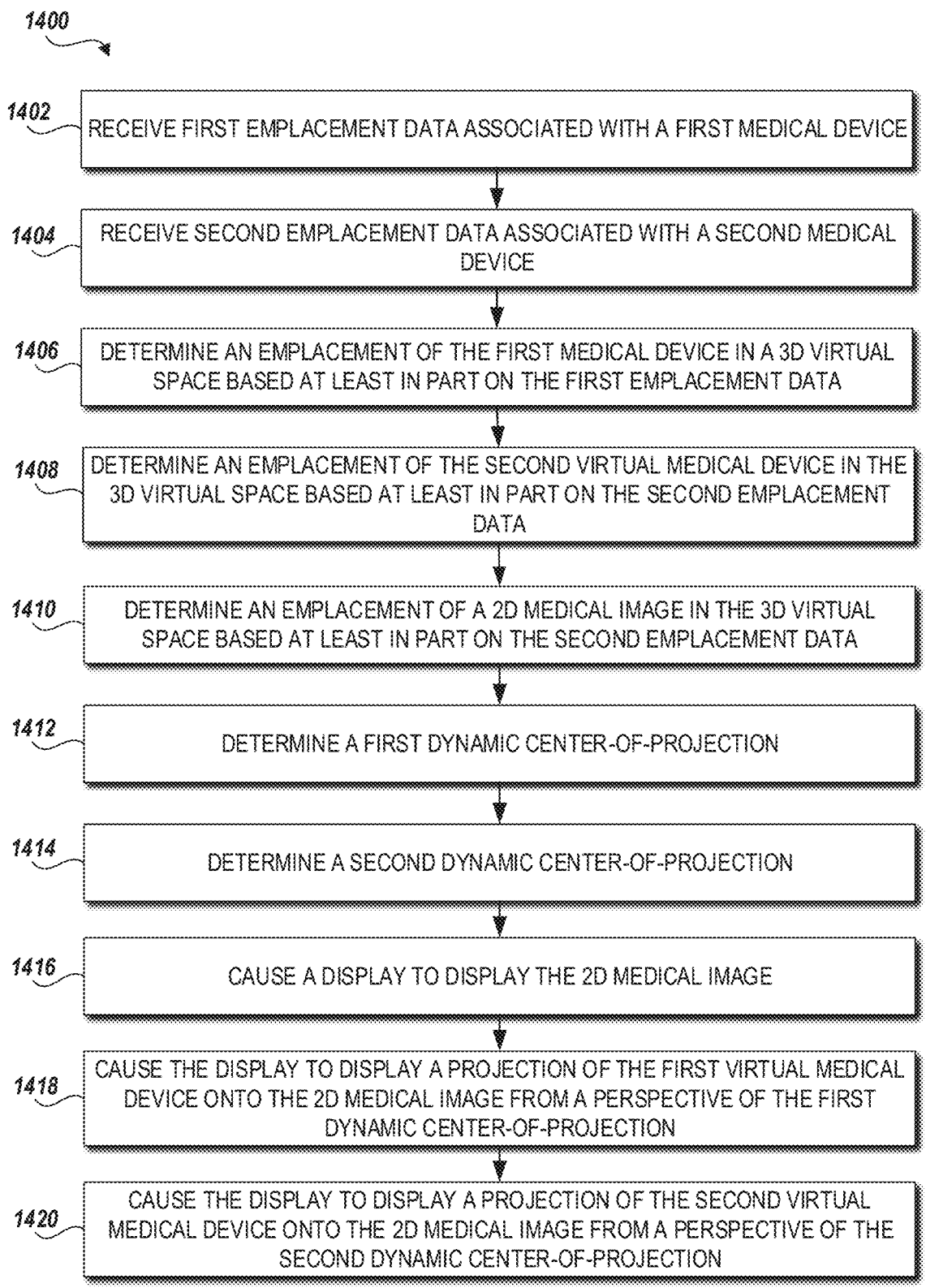
FIG. 14 is a flow diagram illustrative of an embodiment of a routine implemented by a system for providing improved perception of a 2D scene for medical device navigation.

FIG. 14 is a flow diagram illustrative of an embodiment of a routine implemented by the system for providing improved perception of a 2D scene for medical device navigation. In some embodiments, the elements outlined for routine 1400 can be implemented by one or more computing devices/components that are associated with the system 100, such as the position sensing unit 130, the image guidance unit 150, surgical system 140, a head-mounted display, and/or the imaging unit 160. In some embodiments, the elements outlined for routine 1400 can be implemented by one or more computing devices/components that are associated with the medical device 1102 of FIG. 11. Routine 1400 has been logically associated as being generally performed by the system 100. However, the following illustrative embodiment should not be construed as limiting. Furthermore, it will be understood that the various blocks described herein with reference to FIG. 14 can be implemented in a variety of orders. For example, the system 100 can implement some blocks concurrently or change the order as desired. Furthermore, it will be understood that fewer, more, or different blocks can be used as part of the routine 1400. For example, in some embodiments, one or more of blocks 1402, 1404, 1406, 1408, 1410, 1412, or 1414 are not implemented. However, it will be understood that any of the blocks (and more or different blocks) can be implemented as part of routine 1400.

At block 1402, the system 100 receives first emplacement data associated with a first emplacement sensor and/or a first physical medical device. The first emplacement data can be generated by the first emplacement sensor and/or by the position sensing unit 130. In some embodiments, the first emplacement sensor can be associated with the first physical medical device. For example, the first emplacement sensor can be associated with and/or attached to a single-axis device, including, but not limited to, a medical needle, an ablation needle, an introducer needle, a scalpel, a catheter, a stent, or a laparoscopic camera, or a multi-axis device, such as a stapler, a grasper, a transecting device, a resecting device, or a vessel sealer. In some embodiments, the first emplacement sensor can be associated with and/or attached to an imaging device such as an ultrasound transducer.

At block 1404, the system 100 receives second emplacement data associated with a second emplacement sensor and/or a second physical medical device. The second emplacement data can be generated by the second emplacement sensor and/or by the position sensing unit 130. In some embodiments, the second emplacement sensor can be associated with the second physical medical device. For example, the second emplacement sensor can be associated with and/or attached to a single-axis device, including, but not limited to, a medical needle, an ablation needle, an introducer needle, a scalpel, a catheter, a stent, or a laparoscopic camera, or a multi-axis device, such as a stapler, a grasper, a transecting device, a resecting device, or a vessel sealer. In some embodiments, the second emplacement sensor can be associated with and/or attached to an imaging device including, but not limited to, an ultrasound transducer.

At block 1406, the system 100 can determine an emplacement of a first virtual medical device in a 3D virtual space based at least in part on the received first emplacement data. In some cases, the emplacement of a first virtual medical device can correspond to a pose of the first physical medical device. As described herein, the first virtual medical device can correspond to one or more of various physical medical devices. In some embodiments, the system 100 can use the first emplacement data or one or more characteristics of the associated first physical medical device (or a corresponding virtual medical device) to determine the emplacement of at least a portion of the first virtual medical device. For example, characteristics such as shape, size, model, or the like or the first physical medical device may aid in the determination of an emplacement of the first virtual medical device.

In certain embodiments, the system 100 can determine the emplacement of the first virtual medical device in one or more coordinate systems by mapping the first emplacement data from one coordinate system to a second coordinate system. For example, the first emplacement data may be received with respect to a first coordinate system, such as a position sensing coordinate system, and then mapped to a second coordinate system, such as a 3D scene coordinate system and/or a screen coordinate system. The emplacement of the first virtual medical device can be determined with respect to one or more of the coordinate systems. For example, the emplacement of the first virtual medical device can be determined after the first emplacement data has been mapped to the second coordinate system, such as the 3D scene coordinate system and/or the screen coordinate system, or the emplacement of the first virtual medical device can be determined for the first coordinate system, such as the position sensing coordinate system, and then mapped to the 3D scene coordinate system and/or the screen coordinate system.

At block 1408, similar to as described above with respect to block 1406, the system 100 can determine an emplacement of a second virtual medical device in the 3D virtual space based at least in part on the received second emplacement data. In some cases, the emplacement of a first virtual medical device can correspond to a pose of the second physical medical device. As described above, the second virtual medical device can correspond to an imaging device, such as an ultrasound transducer.

At block 1410, the system 100 can determine an emplacement of a 2D medical image in the 3D virtual space based at least in part on received second emplacement data. The 2D medical image can be associated with the second physical medical device. For example, the 2D medical image can be an intra-operative and/or real-time medical image, such as a live ultrasound or intra-operative CT scan, or can be a pre-operative image, such as a pre-operative CT or MRI scan image. A real-time medical image (or real-time medical imaging stream) can refer to a medical image (or real-time medical imaging stream) received in real-time. The 2D medical image can correspond to a live image, such as a live medical image generated by an ultrasound scanner. The 2D medical image can correspond to a pre-operative or intra-operative CT image or MRI image that is communicated in real-time.

In some embodiments, the system 100 can use the second emplacement data and one or more characteristics of the second emplacement sensor or associated second physical medical device (or a corresponding second virtual medical device) to determine the emplacement of the 2D medical image. For example, the characteristics may indicate an emplacement of the 2D medical image relative to the second emplacement sensor, the second physical medical device, or the second virtual medical device.

The system 100 can determine the emplacement of the 2D medical image relative to the second emplacement sensor, the second physical medical device, or the second virtual medical device. For example, the system 100 can use a known relationship between the second emplacement data and the emplacement of the 2D medical image (non-limiting example: the medical image begins 2 cm away from the of the second emplacement data location in a particular direction and ends 5 cm away) and/or use a known relationship between the emplacement of the second emplacement sensor and/or second physical medical device (or second virtual medical device) and the emplacement of the 2D medical image (non-limiting examples: the medical image begins 4 cm from the tip of the second physical medical device (or second virtual medical device) and ends at the tip of the second physical medical device (or second virtual medical device), or the 2D medical image extends 2 cm in either direction from the ends of the second emplacement sensor).

In certain embodiments, the system 100 can determine the emplacement of the 2D medical image in one or more coordinate systems by mapping the second emplacement data from one coordinate system to a second coordinate system. For example, the second emplacement data may be received with respect to a first coordinate system, such as a position sensing coordinate system, and then mapped to a second coordinate system, such as a 3D scene coordinate system and/or a screen coordinate system. The emplacement of the 2D medical image can be determined with respect to one or more of the coordinate systems. For example, the emplacement of the 2D medical image can be determined after the second emplacement data has been mapped to the second coordinate system, such as the 3D scene coordinate system and/or the screen coordinate system, or the emplacement of the 2D medical image can be determined for the first coordinate system, such as the position sensing coordinate system, and then mapped to the 3D scene coordinate system and/or the screen coordinate system.

At block 1412, the system 100 can determine a first point-of-projection location. In some embodiments, the first point-of-projection location corresponds to a projection reference point for determining a single-point projection of the first virtual medical device onto a 2D plane of the 2D medical image.

As described herein, the system 100 can determine an intersection associated with first virtual medical device and the 2D medical image. In some cases, the intersection associated with the first virtual medical device and the 2D plane of the 2D medical image can include, but is not limited to, an intersection of the first medical device with the 2D medical image or the 2D plane of the 2D medical image, an intersection of an axis of the first medical device with the 2D medical image or the 2D plane of the 2D medical image (e.g., the intersection of the trajectory of the first medical device with the 2D medical image or 2D plane), an intersection of a ray that is normal to the 2D medical image, where the ray intersects with the 2D medical image (or 2D plane of the 2D medical image) and some portion of the first medical device (e.g., midpoint, an endpoint closest to the 2D medical image, or an endpoint that is farthest from the 2D medical image, etc.), an intersection of a ray that is not normal to the 2D medical image, where the ray intersects with 2D medical image and the first medical device. In some cases, the ray can intersect with a particular location on the 2D medical image (e.g., center of the 2D medical image, top/bottom, left/right corner, etc.) and a particular location on the first medical device (e.g., midpoint, an endpoint closest to the 2D medical image or an endpoint that is farthest from the 2D medical image, etc.).

Furthermore, as described herein, the system 100 can identify a ray that is normal to the 2D medical image and that passes through the determined intersection, and can select a point along the identified ray. The selected point along the identified ray is the point-of-projection location. As described herein, the point-of-projection location can be at some distance in front of or behind the 2D medical image.

As described herein, the system 100 can determine one or more intersections of projecting lines with a 2D medical image. For example, each of the projecting lines can emanate from the point-of-projection location and can intersect, or meet, both the first virtual medical device and the 2D medical image. In some cases, the projection of the first virtual medical device can be identified or formed based at least in part on at least some of the intersections of the projecting lines with the 2D medical image. For example, the projection of the first virtual medical device can be identified or formed by aggregating some or all of the intersections.

In some embodiments, the first point-of-projection location is dynamic. For example, the first point-of-projection location can be based at least in part on a relative emplacement of the first virtual medical device and the 2D medical image. Accordingly, in some cases, the first point-of-projection location can change as the relative emplacement of the 2D medical image to the first medical device changes, either by movement of the first medical device or movement of the second medical device. As another example, the first point-of-projection location can change as an emplacement of the first virtual medical device changes. Furthermore, the first point-of-projection location can be based at least in part on an angle of the first virtual medical device relative to the 2D medical image. Thus, the first point-of-projection location can change as the angle of the first virtual medical device changes with respect to the 2D medical image.

At block 1414, the system 100 can determine a second point-of-projection location. In some embodiments, the first point-of-projection location is the same as the first point-of-projection location. In some embodiments, the second point-of-projection location can be along a ray that is normal to the 2D medical image and passes through the first point-of-projection location. In some embodiments, the second point-of-projection location can be closer to or further away from the 2D medical image than the first point-of-projection location.

At block 1416, the system 100 causes a display to display the 2D medical image. In some cases, the 2D medical image can be adjusted to fit the size of the display. For example, the 2D medical image can be stretched, scaled, or otherwise resized to fit the dimensions of the display. In some cases, the 2D medical image does not completely fill a viewing area of a display. For example, the 2D medical image can retain its aspect ratio when presented on the display.

At block 1418, the system 100 causes the display to display a projection of the first virtual medical device onto, or composited with, the 2D medical image based at least in part on the first dynamic point-of-projection location determined at block 1412. For example, as described herein, a plurality of first projecting lines can extend from the first point-of-projection location and pass through, or meet, both the first virtual medical device and the plane of the 2D medical image. In some cases, the projection of the first virtual medical device can be identified or formed based at least in part on the intersections of the first projecting lines with the plane of the 2D medical image. For example, in some cases, the projection of the first virtual medical device can be identified or formed by aggregating some or all of the intersections. In some cases, the projection of the first virtual medical device is a flat geometric structure that can be directly mapped onto the display.

At block 1420, the system 100 causes the display to display a projection of the second virtual medical device onto, or composited with, the 2D medical image based at least in part on the second dynamic point-of-projection location determined at block 1414. For example, as described herein, a plurality of second projecting lines can extend from the second point-of-projection location and pass through, or meet, both the second virtual medical device and the plane of the 2D medical image. In some cases, the projection of the first virtual medical device can be identified or formed based at least in part on the intersections of the second projecting lines with the plane of the 2D medical image. For example, in some cases, the projection of the second virtual medical device can be identified or formed by aggregating some or all of the intersections. In some cases, the projection of the second virtual medical device is a flat geometric structure that can be directly mapped onto the display.

It will be understood that the various blocks described herein can be implemented in a variety of orders, and that the system 100 can implement one or more of the blocks concurrently and/or change the order, as desired. For example, the system 100 can concurrently display the 2D medical image, the projection of the first virtual medical device onto the 2D medical image, and the projection of the second virtual medical device onto the 2D medical image. As another example, the system 100 can receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1400. For example, the routine 1400 can include blocks for receiving emplacement data associated with additional emplacement sensors or medical devices, determining emplacements of one or more medical devices, corresponding virtual medical devices, other display objects, displays, and/or users. In some embodiments, the routine 1400 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, intersection indicators, or medical devices in different states or configurations.

In certain embodiments, the system 100 can determine multiple emplacements for the first virtual medical device, the second medical device, or medical image. Similarly, the system 100 can determine multiple single-point projections for the first virtual medical device or the second medical device. For example, the system 100 can determine the single-point projections for a right-eye view and a left-eye view of a stereoscopic display, such as a HMD. In this way, each display in the HMD can display the single-point projections from a slightly different perspective corresponding to a right-eye view and a left-eye view, etc.

In addition, in some cases, the routine 1400 can omit certain blocks, such as, but not limited to, blocks 1402, 1404, 1406, 1410, 1414, 1416, and/or 1420. For example, in some embodiments, the system may not determine emplacement of and/or may not display a portion of the second virtual medical device or a portion of the medical image.

Figure 15:
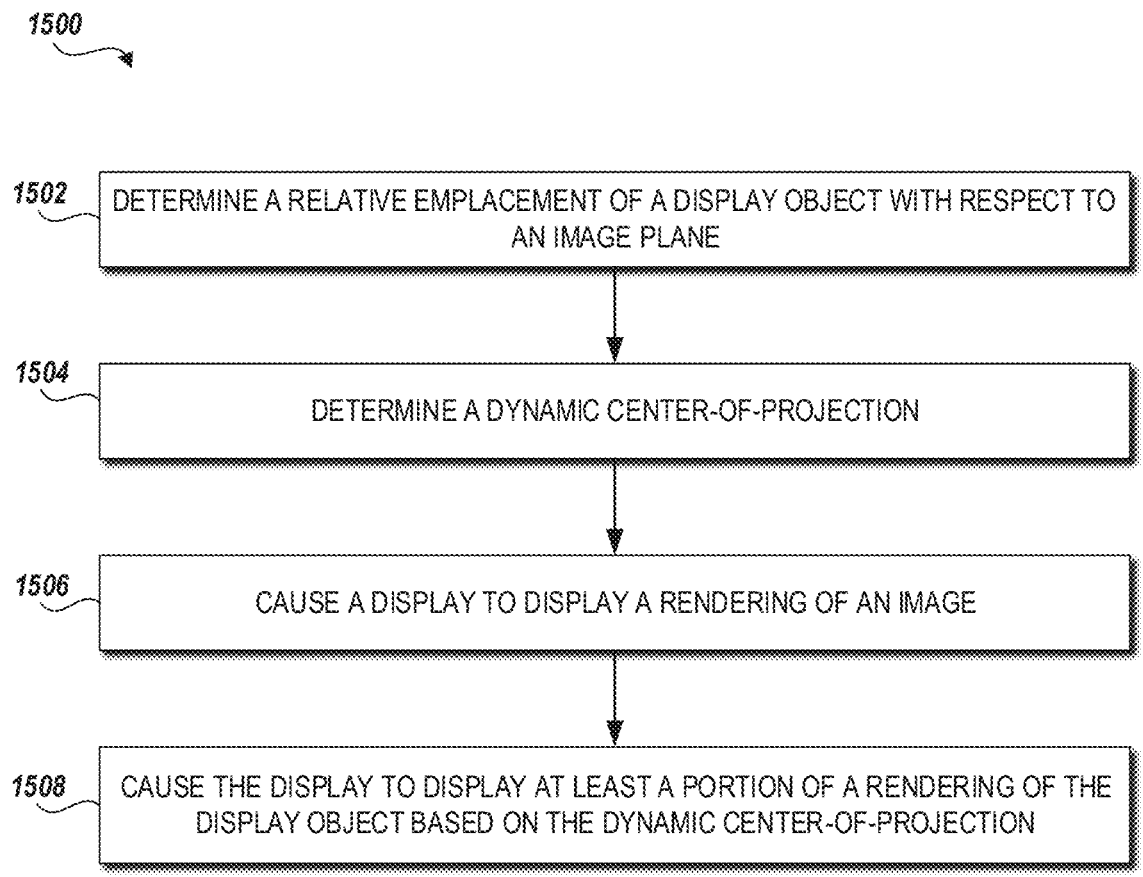
FIG. 15 is a flow diagram illustrative of an embodiment of a routine implemented by a system for providing improved perception of a 2D scene for medical device navigation.

FIG. 15 is a flow diagram illustrative of an embodiment of a routine 1500 implemented by the system for providing improved perception of a 2D scene for medical device navigation. In some embodiments, the elements outlined for routine 1500 can be implemented by one or more computing devices/components that are associated with the system 100, such as the position sensing unit 130, the image guidance unit 150, surgical system 150, a head-mounted display, and/or the imaging unit 160. In some embodiments, the elements outlined for routine 1500 can be implemented by one or more computing devices/components that are associated with the medical device 1102. Routine 1500 has been logically associated as being generally performed by the system 100. However, the following illustrative embodiment should not be construed as limiting. Furthermore, it will be understood that the various blocks described herein with reference to FIG. 15 can be implemented in a variety of orders. For example, the system 100 can implement some blocks concurrently or change the order as desired. Furthermore, it will be understood that fewer, more, or different blocks can be used as part of the routine 1500. For example, in some embodiments, one or more of blocks 1502, 1504, 1506, or 1508 are not implemented. However, it will be understood that any of the blocks (and more or different blocks) can be implemented as part of routine 1500.

At block 1502, the system 100 determines a relative emplacement of a display object with respect to an image plane. For example, similar to blocks 1402, 1404, 1406, and/or 1408 of FIG. 14, the system can receive emplacement data corresponding to one or more of a physical medical device, a display object, and/or a medical image. Based at least in part on the emplacement data and/or a known relationship between the display object and the image plane, the system can determine the relative emplacement of the display object with respect to the image plane.

At block 1504, similar to block 1412 of FIG. 14, the system 100 determines a dynamic point-of-projection location. For example, as described herein, the dynamic point-of-projection location can be based at least in part on an intersection that is based at least in part on the relative emplacement of the virtual medical device and the 2D medical image determined at block 1502.

At block 1506, similar to block 1416 of FIG. 14, the system 100 causes a display to display a rendering of a medical image.

At block 1508, similar to blocks 1418 or 1420 of FIG. 14, the system 100 causes the display to display at least a portion of a rendering of the display object based at least in part on the dynamic point-of-projection location.

It will be understood that the various blocks described herein can be implemented in a variety of orders, and that the system 100 can implement one or more of the blocks concurrently and/or change the order, as desired. For example, the system 100 can concurrently receive the emplacement data from different sources, concurrently receive the medical image, or receive the data in any order. Similarly, the system 100 can concurrently determine the emplacement of the medical image and/or one or more virtual medical devices, etc.

Furthermore, it will be understood that fewer, more, or different blocks can be used as part of the routine 1500. For example, the routine 1500 can include blocks for receiving emplacement data associated with additional emplacement sensors or medical devices, determining emplacements of one or more medical devices, corresponding virtual medical devices, other display objects, displays, and/or users. In some embodiments, the routine 1500 can include determining an emplacement of a medical device associated with the medical image and determining the emplacement of the medical image based at least in part on the determined emplacement of the medical device (or corresponding virtual medical device), and display the virtual medical device concurrently with the medical image. Furthermore, the system 100 can determine and display a variety of image guidance cues, such as trajectory indicators, affected region indicators, intersection indicators, or medical devices in different states or configurations.

In certain embodiments, the system 100 can determine multiple emplacements for the first virtual medical device or medical image. Similarly, the system 100 can determine multiple single-point projections for the first virtual medical device. For example, the system 100 can determine the single-point projections for a right-eye view and a left-eye view of a stereoscopic display, such as a HMD. In this way, each display for the HMD can display the single-point projections from a slightly different perspective corresponding to a right-eye view and a left-eye view, etc.

Other Techniques

In some embodiments, the single-point projections, such as those shown in FIGS. 7C, 8C, 9C, 10C, as well as the imagery shown mapped onto the displays in FIGS. 11 and 13A, can be generated or determined using techniques other than single-origin projection, whereby rays are cast through the geometry of the display objects and intersect with a viewplane (which may or may not coincide with the plane of a medical image) to form the single-point projection. As an example, one may employ simple parallel projection but scale certain portions of the instruments geometry to give the appearance of perspective. For instance, portions of the geometry that are distant from an assumed viewing location, or along a viewing direction, may be dynamically reduced in size. Analogously, geometry elements that are closer to an assumed viewing location, or proximal along a viewing direction, may be dynamically enlarged. Alternatively or additionally, various portions of these geometries may be selectively dynamically translated (for example, laterally or parallel to the medical image plane) based on their distance from an assumed viewing location, or based on their distance from the intersection point of needle axis and medical image plane. The purpose of such distance-proportional scaling and/or lateral translation can be to simulate the characteristic "opening" of near perspective space and the compression and foreshortening of distant perspective space.

As another example, dynamic geometry deformations such as scaling and translations may be applied based on rules other than single-point projection, e.g. with the goal of emphasizing aspects of the viewed treatment geometry other than pure spatial depth. This includes but is not limited to aspects such as momentary importance of a specific instrument or instrument portion for the medical procedure in progress, emphasizing specific geometric relationships such as angles, distances, dimensions, or highlighting electric, chemical, mechanical, etc. effects related to the ongoing treatment.

Stereoscopy for Parallel Projection Imagery

Showing a perspective view for a medical device, such as a virtual medical needle, can be confusing to a viewer when the medical device appears to be in-plane with the medical image due to the necessary projection onto a 2D display. Stereoscopy is a common method for adding perceived depth to such imagery. It is possible to show stereoscopy even without perspective. For example, in some cases, the system can use parallel or orthographic projection techniques and then rotate the 3D data instead of laterally translating it. However, in some cases, this creates vertical disparity (sometimes referred to as "dipvergence"), which can thus induce eyestrain. Horizontal skew could preserve the projective relationships perpendicular to the slice yet still convey stereoscopic depth.

Figures 16A, 16B:
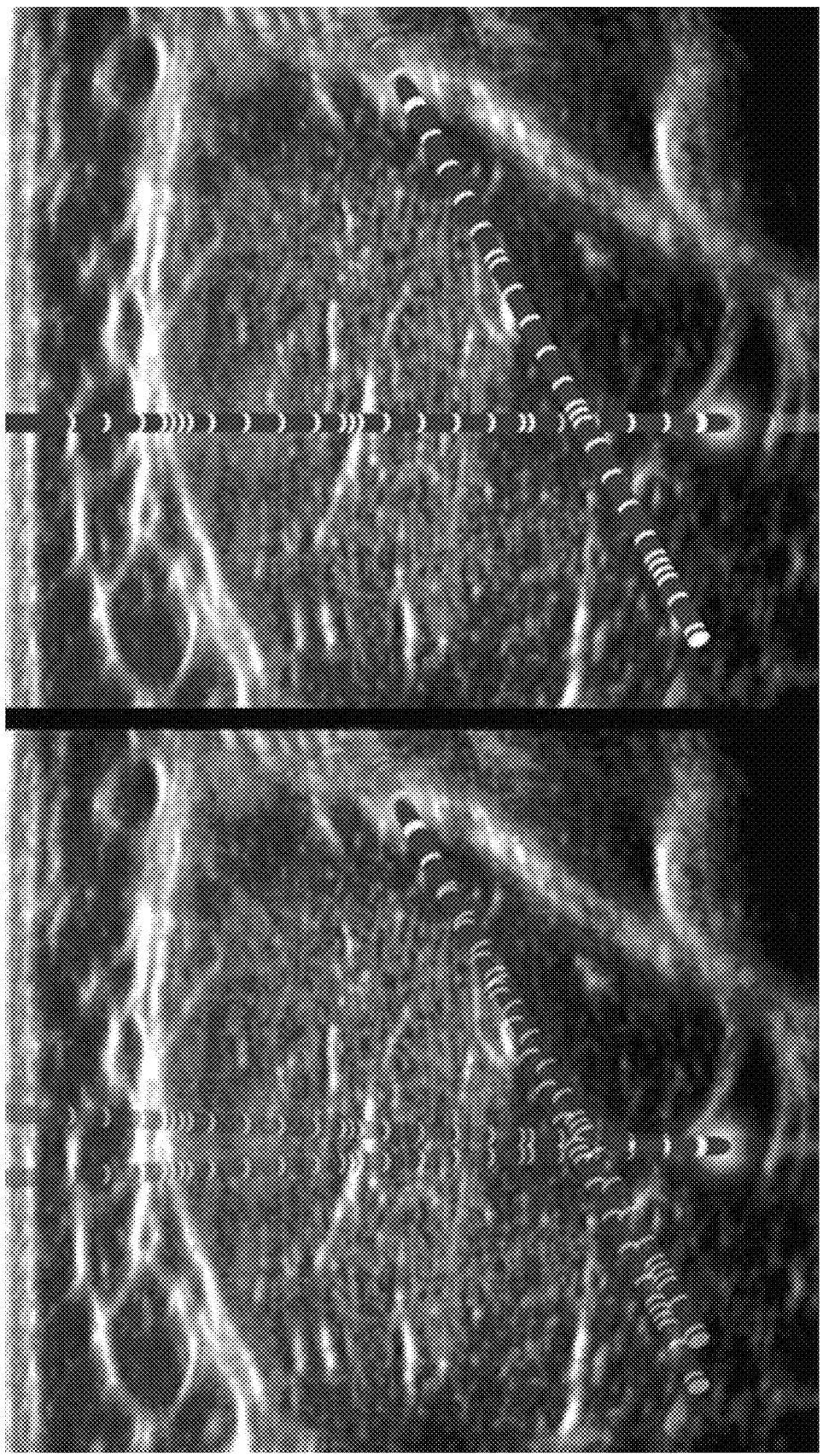
FIG. 16A illustrates an example of a non-perspective parallel-projection stereoscopic image pair with left and right eye images superimposed.
FIG. 16B illustrates an example of a non-perspective parallel-projection non-stereoscopic image pair.

FIG. 16A illustrates an example of a non-perspective parallel-projection stereoscopic image pair (left and right eye images superimposed). FIG. 16B illustrates the corresponding non-stereoscopic parallel-projection image. The image pair in FIG. 16A was created by laterally translating portions of the two needles shown based on the portions' distances from the needle-medical-image intersection point. That is, to create the left eye imagery, needle portions were translated to the right with increasing distance away from the medical image plane and towards the viewer; they were translated to the left with increasing distance from the medical image beyond it, away from the viewer. To create the right eye imagery, the translations were applied in the opposite directions. The result is an easy-to-fuse (when displayed on an appropriate device) parallel projection image with horizontal stereoscopic disparity and no vertical disparity, as well as, unusually, no perspective foreshortening due to parallel projection.

Alternatively to the selective, distance-dependent lateral translation method described here, this kind of imagery can also be created by applying lateral skew transforms to the displayed geometry, globally, first to one side, then to the other, which yields the same kind of stereoscopic image pair. Yet another way of generating such imagery is to use non-orthogonal parallel projection. These methods are can be mathematically equivalent.

Example Embodiments

Various example embodiments of methods, systems and non-transitory computer-readable medium relating to medical device navigation:

Clause 1. A method for medical device navigation, the method comprising:
determining a relative emplacement of a display object with respect to an image plane;
determining a dynamic point-of-projection location based at least in part on the relative emplacement of the display object with respect to the image plane; and
causing a display to concurrently display:
a rendering of a 2D medical image, and
at least a portion of a projection of the display object based at least in part on the dynamic point-of-projection location.

Clause 2. The method of Clause 1, further comprising:
determining an emplacement of a 2D medical image in a 3D virtual space, wherein the an image plane is a plane of the 2D medical image; and
determining an emplacement of the display object in the 3D virtual space,
wherein the relative emplacement of the display object with respect to the image plane is based at least in part on the emplacement of a 2D medical image in the 3D virtual space and the emplacement of the display object in the 3D virtual space.

Clause 3. The method of Clause 2, further comprising:
receiving first emplacement data, wherein said determining the emplacement of the 2D medical image in the 3D virtual space is based at least in part on the first emplacement data; and
receiving second emplacement data, wherein said determining the emplacement of the display object in the 3D virtual space is based at least in part on the second emplacement data.

Clause 4. The method of Clause 1, further comprising determining an intersection based at least in part on the relative emplacement of the display object with respect to the image plane.

Clause 5. The method of Clause 4, wherein the intersection comprises an intersection associated with the display object and the image plane.

Clause 6. The method of Clause 4, wherein the intersection comprises an intersection of the display object with the image plane.

Clause 7. The method of Clause 4, wherein the intersection comprises an intersection of an axis of the display object with the image plane.

Clause 8. The method of Clause 4, wherein the intersection comprises an intersection of a trajectory of the display object with the image plane.

Clause 9. The method of Clause 4, wherein the intersection comprises an intersection of a ray that is normal to the image plane, wherein the ray passes through the image plane and the display object.

Clause 10. The method of Clause 4, wherein the intersection comprises an intersection of a ray that is not normal to the 2D medical image, wherein the ray passes through the display object.

Clause 11. The method of Clause 4, wherein the dynamic point-of-projection location is a point along a ray that is normal to the image plane and that passes through the intersection.

Clause 12. The method of Clause 4, wherein the dynamic point-of-projection location is a point along a ray that is not normal to the image plane and that passes through the intersection.

Clause 13. The method of Clause 1, further comprising mapping points onto the image plane that correspond a plurality of projecting lines, wherein each of the plurality of projecting lines emanate from the dynamic point-of-projection location and intersect both the display object and the image plane.

Clause 14. The method of Clause 1, wherein the at least a portion of the projection of the display object comprises a graphical approximation of at least a portion of the display object from a perspective of the dynamic point-of-projection location in the 3D virtual space.

Clause 15. The method of Clause 1, wherein the at least a portion of the projection of the display object varies in size, wherein the size of the at least a portion of the projection of the display object is based at least in part on a distance of the display object from the dynamic point-of-projection location.

Clause 16. The method of Clause 16, wherein the display object comprises at least one of a virtual medical device or a medical image.

Clause 17. The method of Clause 1, wherein the display object corresponds to a physical medical device.

Clause 18. The method of Clause 17, wherein the physical medical device comprises at least one of an ultrasound transducer, a medical needle, a grasper, a stapler, a vessel sealer, an electrocautery device, a resecting device, a transecting device, a scalpel, a catheter, a stent, or a laparoscopic camera.

Clause 19. The method of Clause 1, wherein the 2D medical image corresponds to an image obtained from an ultrasound transducer.

Clause 20. The method of Clause 1, wherein the 2D medical image resides on the image plane.

Clause 21. A method for medical device navigation, the method comprising:

determining an emplacement of a 2D medical image in a 3D virtual space;

determining an emplacement of a virtual medical device in the 3D virtual space, the virtual medical device corresponding to a physical medical device;

determining an intersection based on the emplacement of the virtual medical device and the emplacement of the 2D medical image;

determining a dynamic point-of-projection location for the virtual medical device based at least in part on the determined intersection;

causing a display to concurrently display:

the 2D medical image, and a projection of the virtual medical device onto the 2D medical image from a perspective of the dynamic point-of-projection location.

Clause 22. The method of Clause 21, wherein the intersection comprises at least one of an intersection of the virtual medical device with a 2D plane of the 2D medical image, an intersection of an axis of the virtual medical device with the 2D medical image, an intersection of a trajectory of the virtual medical device with the 2D medical image, or an intersection of a ray that is normal to the 2D medical image, wherein the ray passes through the 2D medical image and the virtual medical device.

Clause 23. The method of Clause 1, wherein the dynamic point-of-projection location is a point along a ray that is normal to a 2D plane corresponding to the 2D medical image and that passes through the intersection.

Clause 24. The method of Clause 1, wherein said causing the display to concurrently display comprises the projection of the virtual medical device onto the 2D medical image comprises mapping points onto the 2D medical image that correspond a plurality of projecting lines, wherein each of the plurality of projecting lines emanate from the dynamic point-of-projection location and intersect both the virtual medical device and the 2D medical image, wherein the points are mapped at the intersection of a particular set of projecting lines from the plurality of projecting lines with the 2D medical image.

Clause 25. The method of Clause 1, wherein the projection of the virtual medical device comprises a graphical approximation of at least a portion of the physical medical device from a perspective of the point-of-projection location in the 3D virtual space.

Clause 26. The method of Clause 1, wherein the projection of the virtual medical device varies in size, wherein the size of the projection of the virtual medical device is based at least in part on a distance of the virtual medical device from the dynamic point-of-projection location.

Clause 27. The method of Clause 1, wherein the physical medical device is a medical needle and the 2D medical image corresponds to an image obtained from an ultrasound transducer.

Clause 28. The method of Clause 1, wherein the virtual medical device is a first virtual medical device, wherein the physical medical device is a first physical medical device, the method further comprising:

determining an emplacement of a second virtual medical device in the 3D virtual space, the virtual medical device corresponding to a second physical medical device that is different from the first physical medical device; and causing a display to further concurrently display:

a projection of the second virtual medical device onto the 2D medical image from a perspective of the dynamic point-of-projection location.

Clause 29. The method of Clause 1, wherein the virtual medical device is a first virtual medical device, wherein the physical medical device is a first physical medical device, wherein the dynamic point-of-projection location is a first dynamic point-of-projection location, the method further comprising:

determining an emplacement of a second virtual medical device in the 3D virtual space, the virtual medical device corresponding to a second physical medical device that is different from the first physical medical device;

determining a second dynamic point-of-projection location for the second virtual medical device; and causing a display to further concurrently display:

a projection of at least a portion of the second virtual medical device onto the 2D medical image from a perspective of the second dynamic point-of-projection location.

Clause 30. The method of Clause 1, wherein said causing the display to concurrently display the medical images comprises causing the display to display an orthographic projection of the medical image onto the plane of the 2D medical image.

Clause 31. A method for medical device navigation, the method comprising:

determining a relative emplacement of a virtual medical device with respect to a 2D medical image, the virtual medical device corresponding to a physical medical device;

determining an intersection based on the relative emplacement of the virtual medical device and the 2D medical image;

determining a dynamic point-of-projection location of the virtual medical device based at least in part on the determined intersection;

causing a display to concurrently display:

the 2D medical image, and a rendering of the virtual medical device from a perspective of the dynamic point-of-projection location.

Clause 32. A method for medical device navigation, the method comprising:

determining a relative emplacement of a display object with respect to an image plane;

determining a dynamic point-of-projection location based at least in part on the relative emplacement of the display object with respect to the image plane; and causing a display to concurrently display:

a rendering of an image, and at least a portion of a 3D rendering of the display object based at least in part on the dynamic point-of-projection location.

Clause 33. An ultrasound device comprising:

an ultrasound transducer configured to image a region of tissue of a patient;

a display screen coupled to the ultrasound transducer, wherein a viewing area of the display screen is parallel to the region of tissue imaged by the ultrasound transducer; and a processor configured to:

cause the ultrasound transducer to image the region of tissue;

obtain image data corresponding to the ultrasound image slice from the ultrasound transducer;

determine a relative emplacement of a virtual medical device with respect to an ultrasound image plane of the ultrasound image slice, wherein the virtual medical device corresponds to a medical device;

determine a dynamic point-of-projection location based at least in part on the relative emplacement of the virtual medical device with respect to the ultrasound image plane, and cause the display screen to concurrently display:

at least a portion of a 2D rendering of the ultrasound image slice, and at least a portion of a 3D rendering of the virtual medical device based at least in part on the dynamic point-of-projection location.

Clause 34. An ultrasound device comprising:

an ultrasound transducer; and a display screen coupled to the ultrasound transducer, wherein a viewing area of the display screen is parallel to a region imaged by the ultrasound transducer.

Various example embodiments of methods, systems and non-transitory computer-readable medium relating to medical device navigation:

Clause 1. A system for medical device navigation, the system comprising one or more processors configured to:

determine a relative emplacement of a display object with respect to an image plane;

determine a dynamic point-of-projection location based at least in part on the relative emplacement of the display object with respect to the image plane; and cause a display to concurrently display:

a rendering of a 2D medical image, and at least a portion of a projection of the display object based at least in part on the dynamic point-of-projection location.

Clause 2. The system of Clause 1, wherein the one or more processors are further configured to:

determine an emplacement of a 2D medical image in a 3D virtual space, wherein the an image plane is a plane of the 2D medical image; and determine an emplacement of the display object in the 3D virtual space, wherein the relative emplacement of the display object with respect to the image plane is based at least in part on the emplacement of a 2D medical image in the 3D virtual space and the emplacement of the display object in the 3D virtual space.

Clause 3. The system of Clause 2, wherein the one or more processors are further configured to:

receive first emplacement data, wherein to determine the emplacement of the 2D medical image in the 3D virtual space is based at least in part on the first emplacement data; and receive second emplacement data, wherein to determine the emplacement of the display object in the 3D virtual space is based at least in part on the second emplacement data.

Clause 4. The system of Clause 1, wherein the one or more processors are further configured to determine an intersection based at least in part on the relative emplacement of the display object with respect to the image plane.

Clause 5. The system of Clause 4, wherein the intersection comprises an intersection associated with the display object and the image plane.

Clause 6. The system of Clause 4, wherein the intersection comprises an intersection of the display object with the image plane.

Clause 7. The system of Clause 4, wherein the intersection comprises an intersection of an axis of the display object with the image plane.

Clause 8. The system of Clause 4, wherein the intersection comprises an intersection of a trajectory of the display object with the image plane.

Clause 9. The system of Clause 4, wherein the intersection comprises an intersection of a ray that is normal to the image plane, wherein the ray passes through the image plane and the display object.

Clause 10. The system of Clause 4, wherein the intersection comprises an intersection of a ray that is not normal to the 2D medical image, wherein the ray passes through the display object.

Clause 11. The system of Clause 4, wherein the dynamic point-of-projection location is a point along a ray that is normal to the image plane and that passes through the intersection.

Clause 12. The system of Clause 4, wherein the dynamic point-of-projection location is a point along a ray that is not normal to the image plane and that passes through the intersection.

Clause 13. The system of Clause 1, wherein the one or more processors are further configured to map points onto the image plane that correspond a plurality of projecting lines, wherein each of the plurality of projecting lines emanate from the dynamic point-of-projection location and intersect both the display object and the image plane.

Clause 14. The system of Clause 1, wherein the at least a portion of the projection of the display object comprises a graphical approximation of at least a portion of the display object from a perspective of the dynamic point-of-projection location in the 3D virtual space.

Clause 15. The system of Clause 1, wherein the at least a portion of the projection of the display object varies in size, wherein the size of the at least a portion of the projection of the display object is based at least in part on a distance of the display object from the dynamic point-of-projection location.

Clause 16. The system of Clause 16, wherein the display object comprises at least one of a virtual medical device or a medical image.

Clause 17. The system of Clause 1, wherein the display object corresponds to a physical medical device.

Clause 18. The system of Clause 17, wherein the physical medical device comprises at least one of an ultrasound transducer, a medical needle, a grasper, a stapler, a vessel sealer, an electrocautery device, a resecting device, a transecting device, a scalpel, a catheter, a stent, or a laparoscopic camera.

Clause 19. The system of Clause 1, wherein the 2D medical image corresponds to an image obtained from an ultrasound transducer.

Clause 20. The system of Clause 1, wherein the 2D medical image resides on the image plane.

Clause 21. A system for medical device navigation, the system comprising or more processors configured to:

determine an emplacement of a 2D medical image in a 3D virtual space;

determine an emplacement of a virtual medical device in the 3D virtual space, the virtual medical device corresponding to a physical medical device;

determine an intersection based on the emplacement of the virtual medical device and the emplacement of the 2D medical image;

determine a dynamic point-of-projection location for the virtual medical device based at least in part on the determined intersection;

cause a display to concurrently display:

the 2D medical image, and a projection of the virtual medical device onto the 2D medical image from a perspective of the dynamic point-of-projection location.

Clause 22. The system of Clause 21, wherein the intersection comprises at least one of an intersection of the virtual medical device with a 2D plane of the 2D medical image, an intersection of an axis of the virtual medical device with the 2D medical image, an intersection of a trajectory of the virtual medical device with the 2D medical image, or an intersection of a ray that is normal to the 2D medical image, wherein the ray passes through the 2D medical image and the virtual medical device.

Clause 23. The system of Clause 1, wherein the dynamic point-of-projection location is a point along a ray that is normal to a 2D plane corresponding to the 2D medical image and that passes through the intersection.

Clause 24. The system of Clause 1, wherein to cause the display to concurrently display comprises the projection of the virtual medical device onto the 2D medical image comprises mapping points onto the 2D medical image that correspond a plurality of projecting lines, wherein each of the plurality of projecting lines emanate from the dynamic point-of-projection location and intersect both the virtual medical device and the 2D medical image, wherein the points are mapped at the intersection of a particular set of projecting lines from the plurality of projecting lines with the 2D medical image.

Clause 25. The system of Clause 1, wherein the projection of the virtual medical device comprises a graphical approximation of at least a portion of the physical medical device from a perspective of the point-of-projection location in the 3D virtual space.

Clause 26. The system of Clause 1, wherein the projection of the virtual medical device varies in size, wherein the size of the projection of the virtual medical device is based at least in part on a distance of the virtual medical device from the dynamic point-of-projection location.

Clause 27. The system of Clause 1, wherein the physical medical device is a medical needle and the 2D medical image corresponds to an image obtained from an ultrasound transducer.

Clause 28. The system of Clause 1, wherein the virtual medical device is a first virtual medical device, wherein the physical medical device is a first physical medical device, the method wherein the one or more processors are further configured to:

determine an emplacement of a second virtual medical device in the 3D virtual space, the virtual medical device corresponding to a second physical medical device that is different from the first physical medical device; and cause a display to further concurrently display:

a projection of the second virtual medical device onto the 2D medical image from a perspective of the dynamic point-of-projection location.

Clause 29. The system of Clause 1, wherein the virtual medical device is a first virtual medical device, wherein the physical medical device is a first physical medical device, wherein the dynamic point-of-projection location is a first dynamic point-of-projection location, the method wherein the one or more processors are further configured to:

determine an emplacement of a second virtual medical device in the 3D virtual space, the virtual medical device corresponding to a second physical medical device that is different from the first physical medical device;

determine a second dynamic point-of-projection location for the second virtual medical device; and cause a display to further concurrently display:

a projection of at least a portion of the second virtual medical device onto the 2D medical image from a perspective of the second dynamic point-of-projection location.

Clause 30. The system of Clause 1, wherein to cause the display to concurrently display the medical images comprises displaying an orthographic projection of the medical image onto the plane of the 2D medical image.

Clause 31. A system for medical device navigation, the system comprising one or more processors configured to:

determine a relative emplacement of a virtual medical device with respect to a 2D medical image, the virtual medical device corresponding to a physical medical device;

determine an intersection based on the relative emplacement of the virtual medical device and the 2D medical image;

determine a dynamic point-of-projection location of the virtual medical device based at least in part on the determined intersection;

cause a display to concurrently display:

the 2D medical image, and a rendering of the virtual medical device from a perspective of the dynamic point-of-projection location.

Clause 32. A system for medical device navigation, the system comprising one or more processors configured to:

determine a relative emplacement of a display object with respect to an image plane;

determine a dynamic point-of-projection location based at least in part on the relative emplacement of the display object with respect to the image plane; and cause a display to concurrently display:

a rendering of an image, and at least a portion of a 3D rendering of the display object based at least in part on the dynamic point-of-projection location.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list. Depending on the embodiment, certain operations, acts, events, or functions of any of the algorithms described herein can be performed in a different sequence, can be added, merged, or left out altogether (non-limiting example: not all are necessary for the practice of the algorithms). Moreover, in certain embodiments, operations, acts, functions, or events can be performed concurrently, non-limiting examples: through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system 100. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, non-limiting examples: a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Further, the processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices.

Virtualization technologies allow a single physical computing device to host one or more instances of a virtual machine, which virtual machine instance appears to a user as an independent computing device. With virtualization, the host computing device can create, maintain, delete, or otherwise manage virtual machines instances in a dynamic manner. In turn, users can request computing resources, including single computing devices or a configuration of networked computing devices, and be provided with virtual machine instances that provide the requested computing resources.

An instance of a virtual machine may be configured to provide specific functionality. For example, a virtual machine instance may be associated with different combinations of software applications and operating systems or operating system configurations to enable a virtual machine to provide different desired functionalities, or to provide similar functionalities more efficiently.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates the various aspects of the invention in any number of claim forms. For example, while only one aspect of the invention may be recited as a means-plus-function claim under 35 U.S.C sec. 108(f) (AIA), other aspects may likewise be embodied as a means-plus-function claim, or in other forms, such as being embodied in a computer-readable medium. Any claims intended to be treated under 35 U.S.C. § 108(f) will begin with the words "means for", but use of the term "for" in any other context is not intended to invoke treatment under 35 U.S.C. § 108(f). Accordingly, the applicant reserves the right to pursue additional claims after filing this application, in either this application or in a continuing application.

Disjunctive language such as the phrase "at least one of X, Y, or Z," unless specifically stated otherwise, is otherwise understood with the context as used in general to present that an item, term, etc., may be either X, Y, or Z, or any combination thereof (non-limiting examples: X, Y, and/or Z). Thus, such disjunctive language is not generally intended to, and should not, imply that certain embodiments require at least one of X, at least one of Y, or at least one of Z to each be present.

Unless otherwise explicitly stated, articles such an "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

The previous description of the disclosed implementations is provided to enable a person skilled in the art to make or use the present invention. Various modifications to these implementations will be readily apparent to those skilled in the art, and the generic principles defined herein can be applied to other implementations without departing from the spirit or scope of the invention. Furthermore, although described above with reference to medical devices and procedures, it will be understood that the embodiments described herein can be applied to other systems in which non-medical objects are tracked and non-medical image streams are received, and virtual representations are displayed on a display and/or systems in which multiple objects are displayed on a display within a virtual space, such as within a virtual 3D space. Thus, the present invention is not intended to be limited to the implementations shown herein but is to be accorded the widest scope consistent with the principles and novel features disclosed herein.

We claim:

1. A method for medical device navigation, the method comprising:
   determining an emplacement of a 2D medical image in a 3D virtual space;
   determining an emplacement of a virtual medical device in the 3D virtual space, the virtual medical device corresponding to a physical medical device;
   determining an intersection of a trajectory of the virtual medical device and the 2D medical image based on the emplacement of the virtual medical device and the emplacement of the 2D medical image;
   determining a dynamic point-of-projection location for the virtual medical device based at least in part on the determined intersection,
   wherein the dynamic point-of-projection location is a point along a ray that is normal to a 2D plane corresponding to the 2D medical image and that passes through the intersection,
   wherein the dynamic point-of-projection location changes as a relative emplacement between the virtual medical device and the 2D medical image changes; and
   causing a display to concurrently display a 2D scene comprising:
      the 2D medical image, and
      a 2D projection of the virtual medical device onto the 2D medical image from a perspective of the dynamic point-of-projection location, wherein portions of the 2D projection that correspond to portions of the virtual medical device that are more distant from the dynamic point-of-projection location appear smaller in the 2D scene than portions of the 2D projection that correspond to portions of the virtual medical device that are nearer to the dynamic point-of-projection location, and wherein the 2D projection of the virtual medical device changes as the relative emplacement between the virtual medical device and the 2D medical image changes.

2. The method of claim 1, wherein said causing the display to concurrently display comprises the projection of the virtual medical device onto the 2D medical image comprising mapping points onto the 2D medical image that correspond a plurality of projecting lines, wherein each of the plurality of projecting lines emanate from the dynamic point-of-projection location and intersect both the virtual medical device and the 2D medical image, wherein the points are mapped at the intersection of a particular set of projecting lines from the plurality of projecting lines with the 2D medical image.

3. The method of claim 1, wherein the projection of the virtual medical device comprises a graphical approximation of at least a portion of the physical medical device from a perspective of the point-of-projection location in the 3D virtual space.

4. The method of claim 1, wherein the physical medical device is a medical needle and the 2D medical image corresponds to an image obtained from an ultrasound transducer.

5. The method of claim 1, wherein the virtual medical device is a first virtual medical device, wherein the physical medical device is a first physical medical device, the method further comprising:
- determining an emplacement of a second virtual medical device in the 3D virtual space, the second virtual medical device corresponding to a second physical medical device that is different from the first physical medical device; and
- causing the display to further concurrently display on the 2D scene:
  - a projection of the second virtual medical device onto the 2D medical image from the perspective of the dynamic point-of-projection location.

6. The method of claim 1, wherein the virtual medical device is a first virtual medical device, wherein the physical medical device is a first physical medical device, wherein the dynamic point-of-projection location is a first dynamic point-of-projection location, the method further comprising:
- determining an emplacement of a second virtual medical device in the 3D virtual space, the virtual medical device corresponding to a second physical medical device that is different from the first physical medical device;
- determining a second dynamic point-of-projection location for the second virtual medical device; and
- causing the display to further concurrently display on the 2D scene:
  - a projection of at least a portion of the second virtual medical device onto the 2D medical image from a perspective of the second dynamic point-of-projection location, wherein the second dynamic point-of-projection location is different from the first dynamic point-of-projection location.

7. The method of claim 1, wherein said causing the display to concurrently display the 2D scene comprises causing the display to display an orthographic projection of the virtual medical device onto the plane of the 2D medical image.

8. A method for medical device navigation, the method comprising:
- determining a relative emplacement of a virtual medical device with respect to an image plane of a 2D medical image;
- determining a dynamic center-of-projection based at least in part on the relative emplacement of the virtual medical device with respect to the image plane, wherein the dynamic center-of-projection changes as the relative emplacement of the virtual medical device and the 2D medical image changes;
- determining a first intersection based at least in part on the relative emplacement of the display object with respect to the image plane, wherein the first intersection comprises a second intersection of an axis of the display object with the image plane, and wherein the dynamic center-of-projection is a point along a ray that is normal to the image plane and that passes through the first intersection; and
- causing a display to concurrently display a 2D scene comprising:
  - a rendering of the 2D medical image, and
  - a projection of the virtual medical device based at least in part on the dynamic center-of-projection, wherein portions of the projection that correspond to portions of the virtual medical device that are more distant from the dynamic center-of-projection appear smaller in the 2D scene than portions of the projection that correspond to portions of the virtual medical device that are nearer to the dynamic center-of-projection.

9. The method of claim 8, further comprising:
- determining an emplacement of the 2D medical image in a 3D virtual space; and
- determining an emplacement of the virtual medical device in the 3D virtual space,
- wherein the relative emplacement of the virtual medical device with respect to the image plane is based at least in part on the emplacement of the 2D medical image in the 3D virtual space and the emplacement of the virtual medical device in the 3D virtual space.

10. The method of claim 9, further comprising:
- receiving first emplacement data, wherein said determining the emplacement of the 2D medical image in the 3D virtual space is based at least in part on the first emplacement data; and
- receiving second emplacement data, wherein said determining the emplacement of the virtual medical device in the 3D virtual space is based at least in part on the second emplacement data.

11. The method of claim 8, further comprises mapping points onto the image plane that correspond a plurality of projecting lines, wherein each of the plurality of projecting lines emanate from the dynamic center-of-projection and intersect both the virtual medical device and the image plane.

12. The method of claim 8, wherein at least a portion of the projection of the virtual medical device comprises a graphical approximation of at least a portion of the virtual medical device from a perspective of the dynamic center-of-projection.

13. A system for medical device navigation comprising one or more processors configured to:
- determine an emplacement of a 2D medical image in a 3D virtual space;
- determine an emplacement of a virtual medical device in the 3D virtual space, the virtual medical device corresponding to a physical medical device;
- determine an intersection of a trajectory of the virtual medical device and the 2D medical image based on the emplacement of the virtual medical device and the emplacement of the 2D medical image;
- determine a dynamic point-of-projection location for the virtual medical device based at least in part on the determined intersection,
- wherein the dynamic point-of-projection location is a point along a ray that is normal to a 2D plane corresponding to the 2D medical image and that passes through the intersection,
- wherein the dynamic point-of-projection location changes as a relative emplacement between the virtual medical device and the 2D medical image changes; and
- cause a display to concurrently display a 2D scene comprising:
  - the 2D medical image, and
  - a 2D projection of the virtual medical device onto the 2D medical image from a perspective of the dynamic point-of-projection location, wherein portions of the 2D projection that correspond to portions of the virtual medical device that are more distant from the dynamic point-of-projection location appear smaller in the 2D scene than portions of the 2D projection that correspond to portions of the virtual medical device that are nearer to the dynamic point-of-projection location, and wherein the 2D projection of the virtual medical device changes as the relative emplacement between the virtual medical device and the 2D medical image changes.

14. The system of claim 13, wherein to cause the display to concurrently display the 2D scene, the one or more processors is configured to map the projection of the virtual medical device onto the 2D medical image at least in part by mapping points onto the 2D medical image that correspond a plurality of projecting lines, wherein each of the plurality of projecting lines emanate from the dynamic point-of-projection location and intersect both the virtual medical device and the 2D medical image, wherein the points are mapped at the intersection of a particular set of projecting lines from the plurality of projecting lines with the 2D medical image.

15. The system of claim 13, wherein the projection of the virtual medical device comprises a graphical approximation of at least a portion of the physical medical device from a perspective of the point-of-projection location in the 3D virtual space.

16. The system of claim 13, wherein the physical medical device is a medical needle and the 2D medical image corresponds to an image obtained from an ultrasound transducer.

* * * * *